(12) United States Patent
Kato et al.

(10) Patent No.: US 6,326,369 B1
(45) Date of Patent: Dec. 4, 2001

(54) BICYCLIC QUINONE COMPOUNDS, THEIR PRODUCTION AND USE

(75) Inventors: Kaneyoshi Kato, Kawanishi; Taiichi Ohra, Izumi; Masaomi Miyamoto, Takarazuka, all of (JP)

(73) Assignee: Takeda Chemicals Industries, Ltd., Osaka (JP)

(*) Notice: Subject to any disclaimer, the term of this patent is extended or adjusted under 35 U.S.C. 154(b) by 0 days.

(21) Appl. No.: 09/341,198
(22) PCT Filed: Feb. 2, 1998
(86) PCT No.: PCT/JP98/00422
  § 371 Date: Jul. 6, 1999
  § 102(e) Date: Jul. 6, 1999
(87) PCT Pub. No.: WO98/33758
  PCT Pub. Date: Aug. 6, 1998

(30) Foreign Application Priority Data

Feb. 3, 1997 (JP) .................................................... 9-020763

(51) Int. Cl.$^7$ .................................................... C07C 50/32
(52) U.S. Cl. .................... 514/237.5; 546/157; 546/158; 546/189; 546/191; 546/301; 548/260; 548/310.1; 548/478; 549/437; 552/298; 560/28; 560/53; 560/56; 560/119; 560/121; 560/160; 560/256; 562/466; 562/501; 562/503; 564/158; 564/172; 564/217; 564/360; 568/33; 568/327; 568/379; 568/441; 568/633
(58) Field of Search .............................. 514/237.5, 238.8, 514/239.2, 255, 311, 312, 316, 319, 340, 345, 359, 394, 415, 464, 529, 530, 546, 569, 573, 616, 623, 629, 659, 715, 719, 729, 730; 552/298; 544/174, 360, 398; 546/157, 158, 189, 191, 301; 548/260, 310.1, 478; 549/437; 560/28, 53, 56, 119, 121, 160, 256; 562/466, 501, 503; 564/158, 172, 217, 360; 568/33, 327, 379, 441, 633

(56) References Cited

U.S. PATENT DOCUMENTS 5,059,627 10/1991 Goto et al. .

FOREIGN PATENT DOCUMENTS

A 515917 12/1992 (EP) .

A 59-128348 7/1984 (JP) .

OTHER PUBLICATIONS

S. Perri and H. Moore, "Rearrangements of Cyclobutenones. Synthesis of . . . " J. Am. Chem. Soc., 1990, 112, pp. 1897–1905.

P. Brown et al., "Studies of Chromenes. Part 9. Syntheses of Chromenequinones" J. Chem. Soc. Perkin Trans. 1, pp. 2979–2988.

L. Briggs et al., "Chemistry of Fungi. XI Corticins A, B, and C, Benzobibenzofurans from . . ." Aust. J. Chem., 1976, 29, 179–90.

Database CAPLUS on STN, Acc. No. 1990:179709, Kato et al., 'Esters of ascorbic acid 2–phosphates as antioxidant drugs,' EP 339486 (abstract), 1990.*

Database CAPLUS on STN, Acc. No. 1992:447972, Xia et al., 'Rearrangements of 4–alkynylcyclobutenones. Annelated spiroepoxycyclohexadienones and quinones form 4–(1,5–alkadiynyl)–4–methoxy– or– hydroxyclobutenones.' J. Org. Chem., (1992), 57(14), p. 3765–6 (abstract), 1992.*

Protective Groups in Organic Synthesis 2nd ed., Green and Wuts, John Wiley & Sons, Inc., NY, 1991.*

* cited by examiner

Primary Examiner—Johann Richter
Assistant Examiner—Brian J. Davis
(74) Attorney, Agent, or Firm—Mark Chao; Elaine M. Ramesh

(57) ABSTRACT

A compound of the formula:

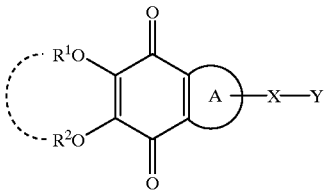

wherein $R^1$ and $R^2$ each represents a lower alkyl, or $R^1$ and $R^2$ may be bonded together to form a ring; X represents a spacer of which the number of atoms constituting the principal chain is 1 to 15; Y represents an acyl, or a hydroxy, an amino or an aromatic group, each of which may be substituted; and ring A represents a 5- to 8-membered ring which may be further substituted apart from —X—Y, or a salt thereof is useful as a pharmaceutical composition for preventing or treating disease related to mitochondrial dysfunction.

20 Claims, No Drawings

BICYCLIC QUINONE COMPOUNDS, THEIR PRODUCTION AND USE

TECHNICAL FIELD

The present invention relates to a bicyclic or tricyclic quinone compound having an excellent mitochondrial function activating effect, to a production thereof and to a use thereof, for example, a pharmaceutical composition effective in treating Alzheimer's disease, etc.

BACKGROUND ART

Neurodegenerative diseases such as Alzheimer's disease and Parkinson's disease are becoming popular with the recent increase in the old-age population, and there is an increasing demand for medicines for preventing and/or treating such neurodegenerative diseases.

Recently, it is said that one factor causing those diseases is the hypofunction of mitochondrial complexes. Mitochondria exist in all animal cells, while participating in the production of energy necessary for cell activities via electron-transfer system. However, mitochondria and mitochondrial genes are easily damaged by oxidative stress deriving from dysfunction of the electron-transport system (for example, radical attack of reactive oxygen species, etc.), resulting in energetic hypometabolism and cell degeneration. In particular, brain cells require high energy consumption, in which, therefore, mitochondria existing are more easily degenerated, thereby resulting in so-called brain electron-transport mitochondrial disorders to be caused by anomalous mitochondrial transmission with aging [e.g., Proceeding of National Academy of Sciences, USA, 91, 8731–8738 (1994), etc.].

Ubiquinone, which is a particular quinone compound, is indispensable as the coenzyme for oxidation-reduction in electron-transport systems. Derivatives having the quinone skeleton of ubiquinone have been produced.

As a compound having a mitochondrial function activating effect and a nerve growth factor production enhancing effect, known is idebenone; 6-(10-hydroxydecyl)-2,3-dimethoxy-5-methyl-1,4-benzoquinone [e.g., JP-A-56-97223, U.S. Pat. No. 4,436,753, JP-A-3-81218, U.S. Pat. No. 5,059,627, Biochemical and Biophysical Research Communications, 125, 1046–1052 (1984), etc.].

On the other hand, the following bicyclic or tricyclic quinone compounds are known.

1) JP-A-59-128348 discloses a compound of the formula:

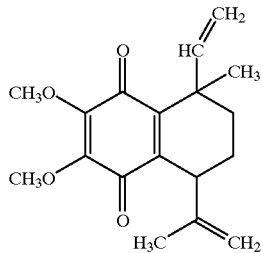

which has a prostaglandin biosynthesis inhibiting effect and is useful as a non-steroidal, anti-inflammatory analgesic.

2) Journal of the American Chemical Society, 112, 1987–1905 (1990) discloses a compound of the formula:

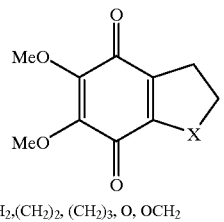

X: $CH_2(CH_2)_2$, $(CH_2)_3$, O, $OCH_2$

3) Chemical Society Perkin Transactions, 1, 2979–2988 (1990) discloses compounds of formulae:

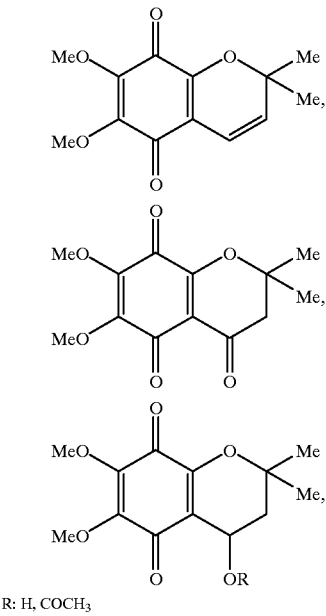

R: H, $COCH_3$ which have an anti-tumoral activity.

4) Australian Journal of Chemistry, 29, 179–190 (1976) discloses a compound of the formula:

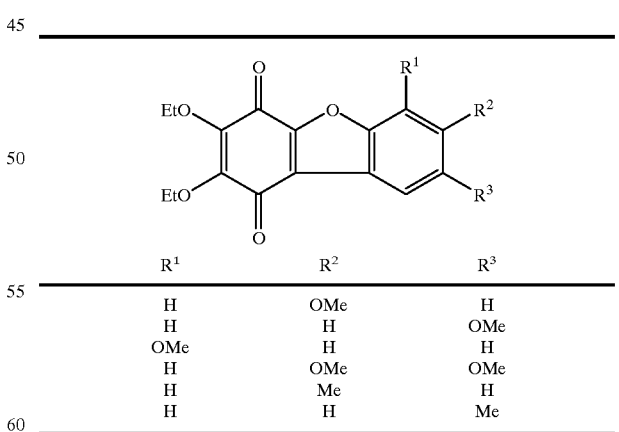

| $R^1$ | $R^2$ | $R^3$ |
|---|---|---|
| H | OMe | H |
| H | H | OMe |
| OMe | H | H |
| H | OMe | OMe |
| H | Me | H |
| H | H | Me |

Studies of medicines for inhibiting mitochondrial dysfunctions, which are for treatment of Alzheimer's disease, etc., are being made, while being essentially directed to antioxidants. It is now desired to develop compounds which are different from the above-mentioned known compounds in their chemical structures but which have an excellent mitochondrial function activating effect and are satisfactory as active ingredients in medicines.

DISCLOSURE OF INVENTION

We, the inventors of the present invention have studied various compounds having a mitochondrial function activating effect, a result, have synthesized, for the first time, a compound being characterized by its chemical structure in that the ring A of the bi- or tri-cyclic quinone skeleton of the formula:

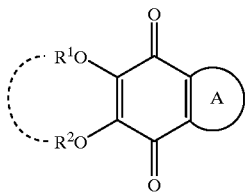

wherein each symbol is as defined below, is substituted by the group of the formula: —X—Y wherein each symbol is as defined below, which is represented by the formula:

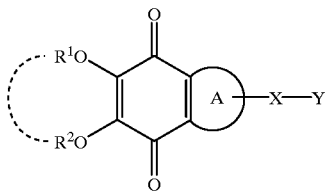
(I)

wherein $R^1$ and $R^2$ each represents a lower alkyl, or $R^1$ and $R^2$ may be bonded together to form a ring;

X represents a spacer of which the number of atoms constituting the principal chain is 1 to 15;

Y represents an acyl, a hydroxy which may be substituted, an amino which may be substituted or an aromatic group which may be substituted; and ring A represents a 5- to 8-membered ring which may be further substituted apart from the group of the formula: —X—Y wherein each symbol is as defined above, or a salt thereof [hereinafter referred to as compound (I)].

We have further found for the first time that the compound (I), being based on its specific chemical structure, has an unexpected, excellent mitochondrial function activating effect along with good metabolism resistance, and is satisfactory as active ingredients in medicines. On the basis of these findings, the inventors have completed the present invention.

Specifically, the invention relates to:
1) Compound (I);
2) a compound of the above 1), wherein $R^1$ and $R^2$ each is a $C_{1-6}$ alkyl, or $R^1$ and $R^2$ form a 5- to 7-membered ring of the formula:

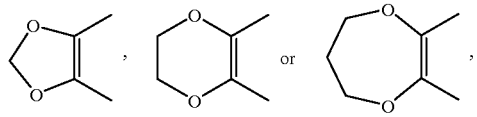

X is (1) a $C_{1-15}$ alkylene, $C_{2-15}$ alkenylene or $C_{2-15}$ alkynylene group, each of which group may be substituted by 1 to 3 substituents selected from the group consisting of oxo and optionally halogenated $C_{1-6}$ alkyl, or (2) a group of the formula: 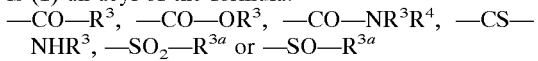
wherein $X^1$ is a (i) divalent $C_{1-8}$ monocyclic non-aromatic hydrocarbon group, (ii) divalent $C_{1-14}$ aromatic hydrocarbon group or (iii) divalent 5- to 14-membered heterocyclic group containing 1 to 4 hetero atoms selected from the group consisting of nitrogen, sulfur and oxygen atoms in addition to carbon atoms, each of which group may be substituted by 1 to 3 substituents selected from the group consisting of oxo and optionally halogenated $C_{1-6}$ alkyl; $X^2$ is O, S, SO or $SO_2$; m and n each is an integer of 0 to 10; and m+n is an integer of 1 to 13;

Y is (1) an acyl of the formula:
—CO—$R^3$, —CO—$OR^3$, —CO—$NR^3R^4$, —CS— $NHR^3$, —$SO_2$—$R^{3a}$ or —SO—$R^{3a}$ wherein $R^3$ is
(a) hydrogen,
(b) a $C_{1-6}$ alkyl, $C_{2-6}$ alkenyl, $C_{2-6}$ alkynyl, $C_{3-6}$ cycloalkyl, $C_{1-14}$ aryl or $C_{7-16}$ aralkyl group, each of which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkylcarbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo, or (c) a 5- to 14-membered heterocyclic group containing 1 to 4 hetero atoms selected from the group consisting of nitrogen, sulfur and oxygen atoms in addition to carbon atoms, which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted by 1 or 2 substituents selected from the group consisting of (xiii-1) a $C_{1-6}$ alkyl, (xiii-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xiii-3) a $C_{6-10}$ aryl-carbonyl, (xiv) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xvi) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvii) sulfo, (xviii) $C_{6-10}$ aryl, (xix) $C_{6-10}$ aryloxy and (xx) oxo, $R^{3a}$ is (a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo, or (b) a 5- to 14-membered heterocyclic group containing 1 to 4 hetero atoms selected from the group consisting of nitrogen, sulfur and oxygen atoms in addition to carbon atoms, which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted by 1 or 2 substituents selected from the group consisting of (xiii-1) a $C_{1-6}$ alkyl, (xiii-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-16}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xiii-3) a $C_{6-10}$ aryl-carbonyl, (xiv) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xvi) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvii) sulfo, (xviii) $C_{6-10}$ aryl, (xix) $C_{6-10}$ aryloxy and (xx) oxo, $R^4$ is hydrogen or a $C_{1-6}$ alkyl; or $R^3$ and $R^4$ may, together with the adjacent nitrogen atom, form a 5- to 7-memebred nitrogen-containing heterocyclic ring which may be substituted by 1 to 3 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted by 1 or 2 substituents selected from the group consisting of (xiii-1) a $C_{1-6}$ alkyl, (xiii-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xiii-3) a $C_{6-10}$ aryl-carbonyl, (xiv) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xvi) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvii) sulfo, (xviii) $C_{6-10}$ aryl, (xix) $C_{6-10}$ aryloxy and (xx) oxo, (2) a hydroxy which may be substituted by (a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo, (b) an acyl of the formula: —CO—$R^3$, —CO—$OR^3$, —CO—$NR^3R^4$, —CS—$NHR^3$, —$SO_2$—$R^{3a}$ or —SO—$R^{3a}$ wherein each symbol is as defined above, or (c) a 5- to 10-membered aromatic heterocyclic group, (3) an amino which may be substituted by 1 or 2 substituents selected from the group consisting of (a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii)

optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- t6 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo, and (b) an acyl of the formula: —CO—$R^3$, —CO—O$R^3$, —CO—N$R^3R^4$, —CS—NH$R^3$, —SO$_2$—$R^{3a}$ or —SO—$R^{3a}$ wherein each symbol is as defined above, (4) a 5- to 7-membered saturated cyclic amino which may be substituted by 1 or 2 substituents selected from the group consisting of (i) a $C_{1-6}$ alkyl, (ii) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (iii) a $C_{6-10}$ aryl-carbonyl, or (5) an aromatic group selected among a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (i) halogen, (ii)$C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted by 1 or 2 substituents selected from the group consisting of (xiii-1) a $C_{1-6}$ alkyl, (xiii-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xiii-3) a $C_{6-10}$ aryl-carbonyl, (xiv) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xvi) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvii) sulfo, (xviii) $C_{6-10}$ aryl, (xix) $C_{6-10}$ aryloxy and (xx) oxo; and ring A is a 5- to 8-membered carbocyclic or heterocyclic ring optionally containing 1 to 3 hetero atoms selected from the group consisting of nitrogen, sulfur and oxygen atoms in addition to carbon atoms, which ring may contain a double bond apart from the double bond condensed with a quinone ring, and may be further substituted by 1 to 3 substituents selected from the group consisting of (1) carboxy,
(2) $C_{1-6}$ alkoxy-carbonyl,
(3) carbamoyl,
(4) mono- or di-$C_{1-6}$ alkylamino-carbonyl,
(5) optionally hydroxylated $C_{1-6}$ alkyl,
(6) oxo and
(7) $C_{6-14}$ aryl which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5-to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amnino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo;

3) a compound of the above 1), wherein $R^1$ and $R^2$ each is $C_{1-6}$ alkyl;

4) a compound of the above 1), wherein X is a spacer of which the number of atoms constituting the principal chain is 2 to 15;

5) a compound of the above 1), wherein X is (1) a $C_{1-15}$ alkylene which may be substituted by 1 to 3 substituents selected from the group consisting of an oxo and an optionally halogenated $C_{1-6}$ alkyl or (2) a group of the formula: —$(CH_2)m$—$X^1$—, —$(CH_2)m$—$X^2$—$X^1$—, —$X^1$—$X^2$—$(CH_2)n$-, —$X^2$—$X^1$—$(CH_2)n$-, —$(CH_2)m$—$X^1$—$(CH_2)n$-, —$(CH_2)m$—$X^2$—$(CH_2)n$-, —$(CH_2)m$—$X^1$—$X^2$—$(CH_2)n$-, —$(CH_2)m$—$X^2$—$X^1$—$(CH_2)n$- or —$X^2$—$X^1$—$X^2$—$(CH_2)n$- wherein $X^1$is (i) a divalent $C_{5-8}$ monocyclic non-aromatic hydrocarbon group, (ii) a divalent $C_{6-14}$ aromatic hydrocarbon group or (iii) a divalent 5- to 14-membered heterocyclic group containing 1 to 4 hetero atoms selected from the group consisting of nitrogen, sulfur and oxygen atoms in addition to carbon atoms, each of which group may be substituted by 1 to 3 substituents selected from the group consisting of an oxo and an optionally halogenated $C_{1-6}$ alkyl; $X^2$ is O, S, SO or $SO_2$; m and n each is an integer of 0 to 10; and m+n is an integer of 1 to 13, each of which group may be substituted by 1 to 3 substituents selected from the group consisting of oxo and optionally halogenated $C_{1-6}$ alkyl;

6) a compound of the above 5), wherein $X^1$ is a divalent $C_{6-14}$ aromatic hydrocarbon group, $X^2$ is O, m is an integer of 0 to 10, n is an integer of 1 to 5, and m+n is an integer of 2 to 10;

7) a compound of the above 1), wherein Y is a hydroxy which may be substituted;

8) a compound of the above 1), wherein ring A is a ring of the formula:

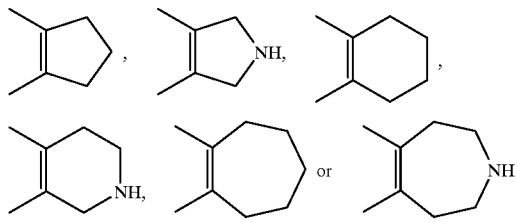

which may be further substituted apart from the group of the formula: —X—Y;

9) a compound of the above 1), wherein $R^1$ and $R^2$ each is $C_{1-6}$ alkyl;

X is (1) a $C_{2-8}$ alkylene or (2) a group of the formula: —$(CH_2)m$—$X^1$—, —$(CH_2)m$—$X^2$—$X^1$—, —$X^1$—$X^2$—$(CH_2)n$-, —$X^2$—$X^1$—$(CH_2)n$-, —$(CH_2)m$—$X^1$—$(CH_2)n$-, —$(CH_2)m$—$X^2$—$(CH_2)n$-, —$(CH_2)m$—$X^1$—$X^2$—$(CH_2)n$-, —$(CH_2)m$—$X^2$—$X^1$—$(CH_2)n$- or —$X^2$—$X^1$—$X^2$—$(CH_2)n$- wherein $X^1$ is a divalent $C_{6-14}$ aromatic hydrocarbon group, $X^2$is O, m is integer of 0 to 10, n is integer of 1 to 5, and m+n is an integer of 2 to 10;

Y is a hydroxy which may be substituted; and ring A is a ring of the formula:

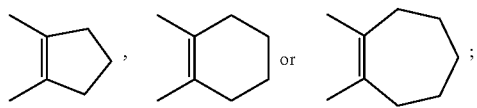

10) a compound of the above 9), wherein Y is a hydroxy substituted by a phenyl which may be substituted by 1 to 3 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (91) hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo;

11) a compound of the above 1), wherein $R^1$ and $R^2$ each is $C_{1-6}$ alkyl;

X is (1) $C_{1-8}$ alkylene or (2) a group of the formula: —(CH$_2$)m'—X$^{2'}$—X$^{1'}$—, —X$^{1'}$—X$^{2'}$—(CH$_2$)m'— or —(CH$_2$)m'—X$^{2'}$—X$^{1'}$—(CH$_2$)n'— wherein X$^{1'}$ is a 1,4-phenylene, X$^{2'}$ is O, m' is an integer of 1 to 4, and n' is 1 or 2;

Y is (1) a carboxy, (2) a carbonyl substituted by (i) a $C_{1-6}$ alkoxy, (ii) an amino, (iii) a mono- or di-$C_{1-6}$ alkylamino or (iv) a 6-membered saturated cyclic amino which may be substituted by a $C_{1-6}$ alkyl, a phenyl or a piperidino, (3) a hydroxy which may be substituted by (i) a phenyl which may be substituted by 1 to 3 substituents selected from the group consisting of halogen, $C_{1-3}$ alkylenedioxy, cyano, $C_{1-6}$ alkyl, $C_{1-6}$ alkoxy and mono-$C_{1-6}$ alkyl-carbamoyl, (ii) a $C_{1-6}$ alkyl-carbonyl, (iii) a mono- or di-$C_{1-6}$ alkyl-carbamoyl, (iv) a pyridyl or (v) quinolyl, (4) an amino substituted by 1 or 2 substituents selected from the group consisting of $C_{1-6}$ alkyl and $C_{1-6}$ alkyl-carbonyl, (5) a 6-membered saturated cyclic amino which may be substituted by (i) a phenyl, (ii) a benzyl which may be substituted by a phenyl, (iii) a piperidino or (iv) a pyridyl, (6) a phenyl, (7) a $C_{6-10}$ quinonyl substituted by 1 or 2 $C_{1-6}$ alkoxy, (8) a phthalimido, (9) a pyridyl which may be substituted by an oxo, (10) a quinolyl which may be substituted by an oxo, (11) benzotriazolyl or (12) a benzimidazolyl; and ring A is a ring of the formula:

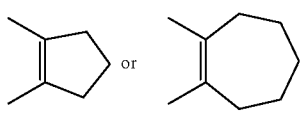

which may be further substituted by a carboxy, $C_{1-6}$ alkoxy-carbonyl, carbamoyl, mono- or di-$C_{1-6}$ alkyl-carbamoyl, hydroxy-$C_{1-6}$ alkyl or phenyl;

12) a compound of the above 1), which is a compound of the formula:

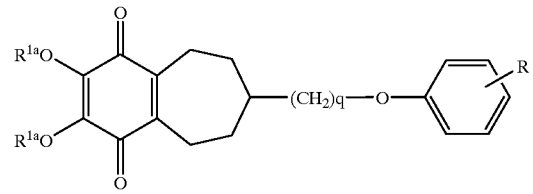

wherein $R^{1a}$ and $R^{2a}$ each is $C_{1-3}$ alkyl; q is an integer of 1 to 4; and R is 1 to 3 substituents selected from the group consisting of halogen, $C_{1-3}$ alkylenedioxy, cyano, optionally halogenated $C_{1-6}$ alkyl, optionally halogenated $C_{1-6}$ alkoxy, $C_{1-6}$ alkoxy-carbonyl, formylamino, $C_{1-6}$ alkyl-carboxamido, $C_{6-10}$ aryl-carboxamido, $C_{1-6}$ alkoxy-carboxamido and $C_{1-6}$ alkylsulfonylamino, or a salt thereof;

13) a compound of the above 1), which is 2-[8-(4-chlorophenoxy)octyl]-5,6-dimethoxyindan-4,7-dione, ethyl 4-[2-(2,3-dimethoxy-1,4-dioxo-4,5,6,7,8,9-hexahydro-1H-benzo[a]cyclohepten-7-yl)ethoxy] benzoate, or 7-[2-(4-chlorophenoxy)ethyl]-2,3-dimethoxy-4,5,6,7,8,9-hexahydro-1H-benzo[a] cycloheptene-1,4-dione;

14) a process for producing compound (I) which comprises subjecting a compound of the formula:

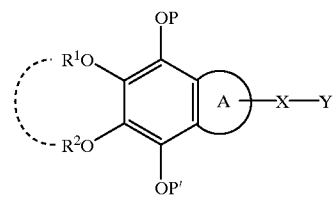

wherein P and P' each represents a protective group and the other symbols are as defined above, or a salt thereof, to quinone production reaction:

15) a pharmaceutical composition which comprises a compound (I), if necessary together with a pharmaceutically acceptable carrier;

16) a composition of the above 15) which is for activating a mitochondrial function;

17) a composition of the above 15) which is for preventing or treating disease related to mitochondrial dysfunction; and 18) a composition of the above 17), wherein the disease is Parkinson's disease, Alzheimer's disease, amyotrophic lateral sclerosis or Huntington's disease, and so forth.

In the above-mentioned formulae, the "lower alkyl" for $R^1$ or $R^2$ includes, for example, $C_{1-6}$ alkyl (e.g., methyl, ethyl, propyl, isopropyl, butyl, isobutyl, sec-butyl, tert-butyl, pentyl, hexyl, etc.), etc. Preferred is a methyl.

The "ring" to be formed by $R^1$ and $R^2$ bonding together includes, for example, a 5- to 7-membered ring in which $R^1$ and $R^2$ form a lower alkylene, a lower alkenylene, etc. Preferred is a 5- to 7-membered ring comprising methylene chains. More preferred is a 5- or 6-membered ring comprising methylene chains.

The "spacer of which the number of atoms constituting the principal chain is 1 to 15" for X is meant to indicate the space between the ring A and Y in which the principle chain is comprised of from 1 to 15 chain atoms.

The "number of atoms constituting the principal chain" as referred to herein shall be counted in such a manner that the number of the atoms existing between the ring A and Y is to be the smallest one irrespective of the presence or absence of hetero atom(s) therebetween. For example, for 1,2-cyclopentylene, the number of atoms in question is counted to be 2; for 1,3-cyclopentylene, it is 3; for 1,4-phenylene, it is 4; for 2,5-naphthylene, it is 5; for 2,6-naphthylene, it is 6; and for 2,6-pyridindiyl, it is 3.

The "spacer of which the number of atoms constituting the principal chain is 1 to 15" includes, for example, a divalent group of which the number of atoms constituting the principal chain is 1 to 15, and which is selected from the group consisting of —O—, —S—, —SO—, —SO$_2$—, a divalent acyclic hydrocarbon group which may be substituted, a divalent cyclic hydrocarbon group which may be substituted, and a divalent heterocyclic group which may be substituted.

One of those divalent groups may form X, or two to four of the same one or different two to four types of such divalent groups may be bonded together to form X. Where two or more those divalent groups are bonded together to form X, they may be the same or different.

The "divalent acyclic hydrocarbon group" for the "divalent acyclic hydrocarbon group which may be substituted" includes, for example, an alkylene, an alkenylene, an alkynylene, etc. Preferred is a straight-chain hydrocarbon group having 1 to 15 carbon atoms.

The "substituent" for the "divalent acyclic hydrocarbon group which may be substituted" includes, for example, an oxo, an optionally halogenated $C_{1-6}$ alkyl, etc.

The above-mentioned "optionally halogenated $C_{1-6}$ alkyl" includes, for example, $C_{1-6}$ alkyl (e.g., methyl, ethyl, propyl, isopropyl, butyl, isobutyl, sec-butyl, tert-butyl, pentyl, hexyl, etc.) optionally having 1 to 5, preferably 1 to 3 halogen atoms (e.g., fluoro, chloro, bromo, iodo, etc.). Thus, for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. can be mentioned.

One to five of those substituents may be substituted at the substitutable positions. When the number of the substituents is two or more, those substituents may be the same as or different from one another.

Preferred Examples of the "divalent acyclic hydrocarbon group which may be substituted" includes, for example, $C_{1-15}$ alkylene, $C_{2-15}$ alkynylene or $C_{2-15}$ alkynylene group, each of which group may be substituted by 1 to 3 substituents selected from the group consisting of an oxo and an optionally halogenated $C_{1-6}$ alkyl, etc.

The "$C_{1-15}$ alkylene which may be substituted by 1 to 3 substituents selected from the group consisting of oxo and optionally halogenated $C_{1-6}$ alkyl" includes, for example, —CH$_2$—, —(CH$_2$)$_2$—, —CH$_2$—CO—, —CH$_2$—CH(CH$_3$)—, —CH$_2$—C(CH$_3$)$_2$—, —(CH$_2$)$_3$—, —CH$_2$—CO—CH$_2$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, etc.

The "$C_{2-15}$ alkenylene which may be substituted by 1 to 3 substituents selected from the group consisting of oxo and optionally halogenated $C_{1-6}$ alkyl" includes, for example, —CH=CH—, —CH$_2$—CH=CH—, —CH=CH—CH(CH$_3$)—, —CH$_2$—CH=CH—CH$_2$—, —CH$_2$—CH$_2$—CH=CH—, —CH=CH—CH=CH—, —CH=CH—CH$_2$—CH$_2$—CH$_2$—, —CH$_2$—CH$_2$—CH$_2$—CH$_2$—CH=CH—, etc.

The "$C_{2-15}$ alkynylene which may be substituted by 1 to 3 substituents selected from the group consisting of oxo and optionally halogenated $C_{1-6}$ alkyl" includes, for example, —C≡C—, —CH$_2$—C≡C—, —CH$_2$—C≡C—CH$_2$—CH$_2$—, etc.

Preferably, the "divalent acyclic hydrocarbon group which may be substituted" is a $C_{1-15}$ alkylene, etc.

The "divalent cyclic hydrocarbon group" for the "divalent cyclic hydrocarbon group which may be substituted" includes, for example, a divalent monocyclic non-aromatic hydrocarbon group, a divalent aromatic hydrocarbon group, etc.

The "divalent monocyclic non-aromatic hydrocarbon group" includes, for example, a divalent monocyclic non-aromatic hydrocarbon group having 5 to 8 carbon atoms. For example, mentioned are a divalent group formed by removing optional two hydrogen atoms from a $C_{5-8}$ cycloalkane or a $C_{5-8}$ cycloalkene. Concretely mentioned are 1,2-cyclopentylene, 1,3-cyclopentylene, 1,2-cyclohexylene, 1,3-cyclohexylene, 1,4-cyclohexylene, 1,2-cycloheptylene, 1,3-cycloheptylene, 1,4-cycloheptylene, 3-cyclohexen-1,4-ylene, 3-cyclohexen-1,2-ylene, 2,5-cyclohexadien-1,4-ylene, etc. Among others, preferred is a $C_{5-8}$ cycloalkylene.

The "divalent aromatic hydrocarbon group" includes, for example, a divalent aromatic hydrocarbon group having 6 to 14 carbon atoms. For example, mentioned is a divalent group formed by removing optional two hydrogen atoms from a 6- to 14-membered, preferably 6- to 10-membered cyclic (mono-, bi- or tri-cyclic) aromatic hydrocarbon, such as benzene, naphthalene, indene, anthracene, etc. Concretely mentioned are 1,2-phenylene, 1,3-phenylene, 1,4-phenylene, 1,4-naphthylene, 1,6-naphthylene, 2,6-naphthylene, 2,7-naphthylene, 1,5-indenylene, 2,5-indenylene, etc.

The "divalent cyclic hydrocarbon group" is preferably a divalent $C_{6-10}$ aromatic hydrocarbon group, more preferably is 1,2-phenylene, 1,3-phenylene and 1,4-phenylene, especially preferably is 1,4-phenylene.

The "substituent" for the "divalent cyclic hydrocarbon group which may be substituted" includes, for example, an oxo, an optionally halogenated $C_{1-6}$ alkyl, etc. The "optionally halogenated $C_{1-6}$ alkyl" is same as the above "optionally halogenated $C_{1-6}$ alkyl".

One to three of those substituents may be substituted at the substitutable positions. When the number of the substituents is two or more, those substituents may be the same as or different from one another.

The "divalent heterocyclic group" for the "divalent heterocyclic group which may be substituted" includes, for example, a divalent group formed by removing optional two hydrogen atoms from (i) a 5- to 14-membered, preferably 5- to 10-membered aromatic heterocyclic ring, (ii) a 6- to 10-membered non-aromatic heterocyclic ring or (iii) a 7- to 10-membered bridged heterocyclic ring, each of which ring contains 1 to 4 hetero atoms of 1 or 2 species selected from the group consisting of nitrogen, sulfur and oxygen atoms in addition to carbon atoms.

The above-mentioned "5- to 14-membered, preferably 5- to 10-membered aromatic heterocyclic ring" includes, for example, an aromatic heterocyclic ring such as thiophene, benzo[b]thiophene, benzo[b]furan, benzimidazole, benzotriazole, benzoxazole, benzothiazole, benzisothiazole, naphtho[2,3-b]thiophene, furan, phenoxathine, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc.; and a ring as formed through condensation of those rings, preferably a monocyclic ring, with one or more, preferably one or two aromatic rings (e.g., benzene ring, etc.), etc.

The above-mentioned "6- to 10-membered non-aromatic heterocyclic ring" includes, for example, pyrrolidine, imidazoline, pyrazolidine, pyrazoline, piperidine, piperazine, morpholine, thiomorpholine, etc.

The above-mentioned "7- to 10-membered bridged heterocyclic ring" includes, for example, quinuclidine, 7-azabicyclo[2,2,1]heptane, etc.

The "divalent heterocyclic group" preferably includes a divalent group formed by removing optional two hydrogen atoms from a 5- to 10-membered aromatic heterocyclic ring (e.g., thiophene, pyridine, indole, quinoline, isoquinoline, phthalazine, etc.) or a 6- to 10-membered non-aromatic heterocyclic ring (e.g., pyrrolidine, piperidine, piperazine, morpholine, thiomorpholine, etc.). Concretely mentioned is 2,5-thiophenediyl, 2,6-pyridinediyl, 1,2-indolediyl, 1,3-indolediyl, 2,4-quinolinediyl, 1,4-isoquinolinediyl, 1,4-phthalazinediyl, 1,3-pyrrolidinediyl, 1,4-piperidinediyl, 1,4-piperazinediyl, etc.

The "substituent" for the "divalent heterocyclic group which may be substituted" includes, for example, an oxo, an optionally halogenated $C_{1-6}$ alkyl, etc. The "optionally halogenated $C_{1-6}$ alkyl" is same as the above "optionally halogenated $C_{1-6}$ alkyl".

One to five, preferably one to three, of those substituents may be substituted at the substitutable positions. When the number of the substituents is two or more, those substituents may be the same as or different from one another.

As specific examples of the "spacer of which the number of atoms constituting the principal chain is 1 to 15", mentioned are (1) a $C_{1-15}$ alkylene, $C_{2-15}$ alkenylene or $C_{2-15}$ alkynylene group, each of which group may be substituted by 1 to 3 substituents selected from the group consisting of oxo and optionally halogenated $C_{1-6}$ alkyl; and (2) a group of the formula: —$(CH_2)_m$—$X^1$—, —$(CH_2)_m$—$X^2$—$X^1$—, —$X^1$—$X^2$—$(CH_2)$n-, —$X^2$—$X^1$—$(CH_2)$n-, —$(CH_2)_m$—$X^1$—$(CH_2)_n$—, —$(CH_2)_m$—$X^2$—$(CH_2)_n$—, —$(CH_2)_m$—$X^1$—$X^2$—$(CH_2)_n$—, —$(CH_2)_m$—$X^2$—$X^1$—$(CH_2)_n$— or —$X^2$—$X^1$—$X^2$—$(CH_2)$n- wherein $X^1$ represents a divalent cyclic hydrocarbon group which may be substituted or a divalent heterocyclic group which may be substituted; $X^2$ represents O, S, SO or $SO_2$; m and n each represent an integer of 0 to 10; and m+n is an integer of 1 to 13; etc.

The "divalent cyclic hydrocarbon group which may be substituted" and the "divalent heterocyclic group which may be substituted" for $X^1$ include those described in detail in the foregoing referring to X, respectively.

X is preferably (1) a $C_{1-15}$ alkylene which may be substituted by 1 to 3 substituents selected from the group consisting of an oxo and an optionally halogenated $C_{1-6}$ alkyl, or (2) a group of the formula: —$(CH_2)$m—$X^1$—, —$(CH_2)$m—$X^2$—$X^1$—, —$X^1$—$X^2$—$(CH_2)$n-, —$X^2$—$X^1$—$(CH_2)$n-, —$X^2$—$(CH_2)$n-, —$(CH_2)$m—$X^1$—$(CH_2)$n-, —$(CH_2)$m—$X^2$—$(CH_2)$n-, —$(CH_2)$m—$X^1$—$X^2$—$(CH_2)$n-, —$(CH_2)$m—$X^2$—$X^1$—$(CH_2)$n- or —$X^2$—$X^1$—$X^2$—$(CH_2)$n- wherein $X^1$ is (i) a divalent $C_{5-8}$ monocyclic non-aromatic hydrocarbon group, (ii) a divalent $C_{6-14}$ aromatic hydrocarbon group or (iii) a divalent 5- to 14-membered heterocyclic group containing 1 to 4 hetero atoms selected from the group consisting of nitrogen, sulfur and oxygen atoms in addition to carbon atoms, each of which group may be substituted by 1 to 3 substituents selected from the group consisting of an oxo and an optionally halogenated $C_{1-6}$ alkyl; $X^2$ is O, S, SO or $SO_2$; m and n each is an integer of 0 to 10; and m+n is an integer of 1 to 13, each of which group may be substituted by 1 to 3 substituents selected from the group consisting of oxo and optionally halogenated $C_{1-6}$ alkyl.

Among others, $X^1$ is preferably a divalent $C_{6-14}$ aromatic hydrocarbon group. Preferably $X^2$ is O. Preferably m is an integer of 0 to 10. Preferably n is an integer of 1 to 5. Preferably m+n is an integer of 2 to 10. Especially preferably, $X^1$ is phenylene, and $X^2$ is O.

The "acyl" for Y includes, for example, an acyl represented by the formula: —(C=O)—$R^3$, —(C=O)—$OR^3$, —(C=O)—$NR^3R^4$, —(C=S)—$NHR^3$, $SO_2$—$R^{3a}$ or —SO—$R^{3a}$ wherein $R^3$ represents hydrogen, a hydrocarbon group which may be substituted or a heterocyclic group which may be substituted, $R^{3a}$ represents a hydrocarbon group which may be substituted or a heterocyclic group which may be substituted, $R^4$ represents hydrogen or $C_{1-6}$ alkyl, or $R^3$ and $R^4$ may, together with the adjacent nitrogen atom, form a nitrogen-containing heterocyclic ring which may be substituted.

The "hydrocarbon group" for the "hydrocarbon group which may be substituted" for $R^3$ or $R^{3a}$ means a group formed by removing an optional hydrogen atom from a hydrocarbon compound, as exemplified by acyclic or cyclic hydrocarbon group such as alkyl, alkenyl, alkynyl, cycloalkyl, aryl and aralkyl. Among them, the following $C_{1-16}$ acyclic or cyclic hydrocarbon group is preferable:

a) $C_{1-6}$ alkyl (e.g., methyl, ethyl, propyl, isopropyl, butyl, isobutyl, sec-butyl, tert-butyl, pentyl, hexyl, etc.), b) $C_{2-6}$ alkenyl (e.g., vinyl, allyl, isopropenyl, butenyl, isobutenyl, sec-butenyl, etc.), c) $C_{2-6}$ alkynyl (e.g., ethynyl, propargyl, butynyl, 1-hexynyl, etc.), d) $C_{3-6}$ cycloalkyl (e.g., cyclopropyl, cyclobutyl, cyclopentyl, cyclohexyl, etc.), and the $C_{3-6}$ cycloalkyl being optionally condensed with one benzene ring, e) $C_{6-14}$ aryl (e.g., phenyl, 1-naphthyl, 2-naphthyl, biphenylyl, 2-indenyl, 2-anthryl, etc.), preferably phenyl, f) $C_{7-16}$ aralkyl (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc.), preferably benzyl.

Among others, $C_{1-6}$ alkyl, $C_{6-14}$ aryl and $C_{7-16}$ aralkyl are preferable.

Examples of the "substituent" for the "hydrocarbon group which may be substituted" include halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, etc.), di-$C_{1-6}$ alkylamino (e.g., dimethylamino, diethylamino, etc.), acyl, acylamino, acyloxy, 5- to 7-membered saturated cyclic amino which may be substituted, sulfo, aromatic group which may be substituted, and so forth.

The "hydrocarbon group" may have 1 to 5, preferably 1 to 3 substituents as mentioned above at possible positions of the hydrocarbon group and, when the number of substituents is two or more, those substituents may be the same as or different from one another.

The above-mentioned "optionally halogenated $C_{1-6}$ alkyl" includes, for example, the "optionally halogenated $C_{1-6}$ alkyl" described in detail in the foregoing referring to X.

The above-mentioned "optionally halogenated $C_{3-6}$ cycloalkyl" includes, for example, $C_{3-6}$ cycloalkyl (e.g., cyclopropyl, cyclobutyl, cyclopentyl, cyclohexyl, etc.) optionally having 1 to 5, preferably 1 to 3 halogen atoms (e.g., fluoro, chloro, bromo, iodo, etc.). Thus, for example, cyclopropyl, cyclobutyl, cyclopentyl, cyclohexyl, 4,4-dichlorocyclohexyl, 2,2,3,3-tetrafluorocyclopentyl, 4-chlorocyclohexyl, etc. can be mentioned.

The above-mentioned "optionally halogenated $C_{1-6}$ alkoxy" includes, for example, $C_{1-6}$ alkoxy (e.g., methoxy, ethyoxy, propoxy, isopropoxy, butoxy, isobutoxy, sec-butoxy, pentyloxy, hexyloxy, etc.) optionally having 1 to 5, preferably 1 to 3 halogen atoms (e.g., fluoro, chloro, bromo, iodo, etc.). Thus, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc. can be mentioned.

The above-mentioned "optionally halogenated $C_{1-6}$ alkylthio" includes, for example, $C_{1-6}$ alkylthio (e.g., methylthio, ethylthio, propylthio, isopropylthio, n-butylthio, sec-butylthio, tert-butylthio, etc.) optionally having 1 to 5, preferably 1 to 3 halogen atoms (e.g., fluoro, chloro, bromo, iodo, etc.). Thus, for example, methylthio, difluoromethylthio, trifluoromethylthio, ethylthio, propylthio, isopropylthio, butylthio, 4,4,4-trifluorobutylthio, pentylthio, hexylthio, etc. can be mentioned.

The above-mentioned "acyl" includes, for example, the "acyl" shown by Y above. Preferred examples are formyl, carboxy, $C_{1-6}$ alkyl-carbonyl (e.g., acetyl, propionyl, etc.), $C_{1-6}$ alkoxy-carbonyl (e.g., methoxycarbonyl, ethoxycarbonyl, propoxycarbonyl, t-butoxycarbonyl, etc.), $C_{6-10}$ aryl-carbonyl (e.g., benzoyl, 1-naphthoyl, 2-naphthoyl, etc.), $C_{6-10}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocyclic carbonyl (e.g., nicotinoyl, isonicotinoyl, thenoyl, furoyl, morpholinocarbonyl, piperazinocarbonyl, pyrrolidinocarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-10}$ aryl-carbamoyl (e.g., phenylcarbamoyl, 1-naphthylcarbamoyl, 2-naphthylcarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g., methylsulfonyl, ethylsulfonyl, etc.), $C_{6-10}$ arylsulfonyl (e.g., benzenesulfonyl, 1-naphthalenesulfonyl, 2-naphthalenesulfonyl, etc.), etc.

The above-mentioned "acylamino" includes, for example, an amino substituted by 1 or 2 "acyl" shown by Y above. Preferred is an acylamino represented by the formula: —$NR^5COR^6$, —$NR^5COOR^{6a}$ or —$NR^5SO_2R^{6a}$ wherein $R^5$ represents hydrogen or $C_{1-6}$ alkyl, $R^6$ represents hydrogen, a hydrocarbon group which may be substituted or a heterocyclic group which may be substituted, $R^{6a}$ represents a hydrocarbon group which may be substituted or a heterocyclic group which may be substituted.

The "$C_{1-6}$ alkyl" for $R^5$ includes the "$C_{1-6}$ alkyl" shown by $R^4$ above.

The "hydrocarbon group which may be substituted" and the "heterocyclic group which may be substituted" for $R^6$ or $R^{6a}$ include the "hydrocarbon group which may be substituted" and the "heterocyclic group which may be substituted" shown by $R^3$, respectively.

Preferred examples of the "acylamino" are formylamino, $C_{1-6}$ alkyl-carboxamido (e.g., acetamido, etc.), $C_{6-10}$ aryl-carboxamido (e.g., phenylcarboxamido, naphthylcarboxamido, etc.), $C_{1-6}$ alkoxy-carboxamido (e.g., methoxycarboxamido, ethoxycarboxamido, propoxycarboxamido, butoxycarboxamido, etc.), $C_{1-6}$ alkyl-sulfonylamino (e.g., methylsulfonylamino, ethylsulfonylamino, etc.), etc.

The above-mentioned "acyloxy" includes, for example, an oxy substituted by one "acyl" shown by Y above. Preferred is an acyloxy represented by the formula: —O—$COR^7$, —O—$COOR^7$ or —O—$CONHR^7$ wherein $R^7$ represents a hydrocarbon group which may be substituted or a heterocyclic group which may be substituted.

The "hydrocarbon group which may be substituted" and the "heterocyclic group which may be substituted" for $R^7$ include the "hydrocarbon group which may be substituted" and the "heterocyclic group which may be substituted" shown by $R^3$, respectively.

Preferred examples of the "acyloxy" are $C_{1-6}$ alkyl-carbonyloxy (e.g., acetoxy, propionyloxy, etc.), $C_{6-10}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-10}$ aryl-carbamoyloxy (e.g., phenylcarbamoyloxy, naphthylcarbamoyloxy, etc.), nicotinoyloxy, etc.

The "5- to 7-membered saturated cyclic amino" for the "5- to 7-membered saturated cyclic amino which may be substituted" exemplified as substituents for the "hydrocarbon group which may be substituted" mentioned above, includes, for example, morpholino, piperazin-1-yl, piperidino, pyrrolidin-1-yl, hexamethyleneimin-1-yl, thiomorpholino, etc.

The "substituent" for the "5- to 7-membered saturated cyclic amino which may be substituted" includes, for example, (i) $C_{1-6}$ alkyl, (ii) $C_{6-14}$ aryl which may be substituted, (iii) $C_{7-16}$ aralkyl which may be substituted, (iv) 5- to 7-membered saturated cyclic amino (e.g., morpholino, piperazin-1-yl, piperidino, pyrrolidin-1-yl, hexamethyleneimin-1-yl, thiomorpholino, etc.) which maybe substituted, (v) 5- or 6-membered aromatic heterocyclic group which may be substituted, (vi) acyl, and so forth.

The "5- to 7 -membered saturated cyclic amino" may have 1 or 2 substituents as mentioned above at possible positions, when the number of substituents is two, those substituents may be the same as or different from one another.

The "$C_{6-14}$ aryl" for the "$C_{6-14}$ aryl which may be substituted" includes the "$C_{6-14}$ aryl" described in detail in the foregoing referring to $R^3$. Preferred is phenyl, etc.

The "$C_{7-16}$ aralkyl" for the "$C_{7-16}$ aralkyl which may be substituted" includes the "$C_{7-16}$ aralkyl" described in detail in the foregoing referring to $R^3$. Preferred is benzyl, etc.

The "5- or 6 -membered aromatic heterocyclic group" for the "5 - or 6 -membered aromatic heterocyclic group which may be substituted" includes, for example, 2-, 3- or 4-pyridyl, 1-, 2- or 3-indolyl, 2- or 3-thienyl, etc. Preferred is 2-, 3- or 4-pyridyl, etc.

The "substituent" which those "$C_{6-14}$ aryl which may be substituted", "$C_{7-16}$ aralkyl which may be substituted", "5- to 7-membered saturated cyclic amino which may be substituted" and "5- or 6-membered aromatic heterocyclic group which may be substituted", which are exemplified as substituents for 5- to 7-membered saturated cyclic amino which may be substituted mentioned above, respectively may have, includes, for example, 1 to 5 of halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), $C_{6-10}$ aryl (e.g., phenyl, etc.), carboxy, formyl, $C_{1-6}$ alkyl-carbonyl (e.g., acetyl, propionyl, etc.), $C_{1-6}$ alkoxy-carbonyl (e.g., methoxycarbonyl, ethoxycarbonyl, propoxycarbonyl, butoxycarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{1-6}$ alkyl-sulfonyl (e.g., methylsulfonyl, ethylsulfonyl, etc.), formylamino, $C_{1-6}$ alkyl-carboxamido (e.g., acetamido, etc.), $C_{1-6}$ alkoxy-carboxamido (e.g., methoxycarboxamido, ethoxycarboxamido, propoxycarboxamido, butoxycarboxamido, etc.), $C_{1-6}$ alkylsulfonylamino (e.g., methylsulfonylamino, ethylsulfonylamino, etc.), $C_{1-6}$ alkyl-carbonyloxy (e.g., acetoxy, propionyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, ethylmethylcarbamoyloxy, etc.), and so forth.

The "optionally halogenated $C_{1-6}$ alkyl", "optionally halogenated $C_{3-6}$ cycloalkyl", "optionally halogenated $C_{1-6}$ alkoxy" and "optionally halogenated $C_{1-6}$ alkylthio" include those described above, respectively.

The "acyl" includes the "acyl" shown by Y above. Preferred is $C_{6-10}$ aryl-carbonyl such as benzoyl, 1-naphthoyl, 2-naphthoyl, etc.

The above-mentioned "aromatic group" for the "aromatic group which may be substituted" includes, for example, an aromatic hydrocarbon group, an aromatic heterocyclic group, and so forth.

The "aromatic hydrocarbon group" includes, for example, a group formed by removing an optional hydrogen atom from a $C_{6-14}$ monocyclic or fused polycyclic (bi- or tri-cyclic) aromatic hydrocarbon compound (e.g., benzene, naphthalene, indene, anthracene, etc.) or a $C_{6-14}$ quinone (e.g., p-benzoquinone, 1,4-naphthoquinone, indan-4,7-dione, etc). Concretely mentioned are a $C_{6-14}$ aryl such as phenyl, 1-naphthyl, 2-naphthyl, 1-indenyl, anthryl, etc.; and a $C_{6-10}$ quinonyl such as indan-4,7-dion-1-yl, indan-4,7-dion-2-yl, p-benzoquinon-2-yl, 1,4-naphthoquinon-2-yl, etc. Among others, a $C_{6-10}$ aryl such as phenyl, 1-naphthyl and 2-naphthyl, and a $C_{6-10}$ quinonyl such as indan-4,7-dion-2-yl, p-benzoquinon-2-yl are preferred.

The "aromatic heterocyclic group" includes, for example, a 5- to 14-membered, preferably 5- to 10-membered aromatic heterocyclic group containing one or more (e.g., 1 to 4) hetero atoms selected from the group consisting of nitrogen, sulfur and oxygen atoms in addition to carbon atoms. Examples of the aromatic heterocyclic group mean a monovalent group formed by removing an optional hydrogen atom from the aromatic heterocyclic ring which can be fused with one or more (preferably one or two) aromatic rings (e.g., benzene ring, etc.). As such rings, concretely mentioned are thiophene, benzo[b]thiophene, benzo[b]furan, benzimidazole, benzotriazole, benzoxazole, benzothiazole, benzisothiazole, naphtho[2,3-b]thiophene, furan, phenoxathiin, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc.

Preferred examples of the "aromatic heterocyclic group" include a 5- or 6-membered aromatic heterocyclic group which can be fused with one benzene ring. Concretely mentioned are 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, 2- or 3-thienyl, phthalimido, etc. More preferable examples include 2- or 3-thienyl, 2-, 3- or 4-pyridyl, 2-quinolyl, 1-isoquinolyl, 1- or 2-indolyl, 2-benzothiazolyl, phthalimido, etc.

The "substituent" for the "aromatic group which may be substituted" includes, for example, halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), 5- to 7-membered saturated cyclic amino which may be substituted, acyl, acylamino, acyloxy, sulfo, $C_{6-10}$ aryl (e.g., phenyl, naphthyl, etc.), $C_{6-10}$ aryloxy (e.g., phenyloxy, naphthyloxy, etc.), oxo, and so forth.

The "optionally halogenated $C_{1-6}$ alkyl", "optionally halogenated $C_{3-6}$ cycloalkyl", "optionally halogenated $C_{1-6}$ alkoxy", "optionally halogenated $C_{1-6}$ alkylthio", "5- to 7-membered saturated cyclic amino which may be substituted", "acyl", "acylamino" and "acyloxy" mentioned above include, for example, those described in detail in the foregoing referring to the "substituents" for the "hydrocarbon group which may be substituted".

The "aromatic group" may have 1 to 5, preferably 1 to 3 substituents mentioned above at possible positions of the aromatic group and, when the number of substituents is two or more, those substituents may be the same as or different from one another.

The "heterocyclic group" for the "heterocyclic group which may be substituted" for $R^3$ or $R^{3a}$ includes, for example, a monovalent group formed by removing an optional hydrogen atom from a 5- to 14-membered (monocyclic, bicyclic or tricyclic) heterocyclic ring containing 1 to 4 hetero atoms of 1 or 2 species selected from the group consisting of nitrogen, oxygen and sulfur atoms in addition to carbon atoms, preferably, (i) a 5- to 14-membered, preferably 5- to 10-membered aromatic heterocyclic ring, (ii) a 6- to 10-membered non-aromatic heterocyclic ring or (iii) a 7- to 10-membered bridged heterocyclic ring.

The above-mentioned "5- to 14-membered aromatic heterocyclic ring", "6- to 10-membered non-aromatic heterocyclic ring" and "bridged heterocyclic ring" include those described in detail in the foregoing referring to the "divalent heterocyclic group" shown by X.

Preferable examples of the "heterocyclic group" include, for example, a 5- to 10-membered (monocyclic or dicyclic) heterocyclic group containing 1 to 4 hetero atoms of 1 or 2 species selected from the group consisting of nitrogen, oxygen and sulfur atoms in addition to carbon atoms. Concretely mentioned are a aromatic heterocyclic group such as 2- or 3-thienyl, 2-, 3- or 4-pyridyl, 2- or 3-furyl, 2-, 3-, 4-, 5- or 8-quinolyl, 4-isoquinolyl, pyrazinyl, 2- or 4-pyrimidinyl, 3-pyrrolyl, 2-imidazolyl, 3-pyridazinyl, 3-isothiazolyl, 3-isoxazolyl, 1-indolyl, 2-indolyl, 2-isoindolylnyl, etc; and a non-aromatic heterocyclic group such as 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, etc.

Among these groups, a 5- or 6-membered heterocyclic group containing 1 to 3 hetero atoms selected from the group consisting of nitrogen, oxygen and sulfur atoms in addition to carbon atoms. Concretely mentioned are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, etc.

The "heterocyclic group which may be substituted" may have 1 to 5, preferably 1 to 3 substituents which the "aromatic group which may be substituted" mentioned above may have. When the number of substituents is two or more, those substituents may be the same as or different from one another.

The "$C_{1-6}$ alkyl" for $R^4$ includes, for example, methyl, ethyl, propyl, isopropyl, butyl, isobutyl, sec-butyl, tert-butyl, pentyl, hexyl, etc.

The "nitrogen-containing heterocyclic ring" for the "nitrogen-containing heterocyclic ring which may be substituted" formed by, taken together with the adjacent nitrogen atom, $R^3$ and $R^4$ includes, for example, a 5- to 7-membered nitrogen-containing heterocyclic ring having one nitrogen atom and optionally having 1 to 3 hetero atoms selected from the group consisting of nitrogen, oxygen and sulfur atoms in addition to carbon atoms. Such examples include piperidine, morpholine, thiomorpholine, piperazine, azetidine, etc. Preferred is 6-membered nitrogen-containing heterocyclic ring having one nitrogen atom and optionally having one hetero atom selected from the group consisting of nitrogen and oxygen atoms in addition to carbon atoms.

The "nitrogen-containing heterocyclic ring which may be substituted" may have 1 to 3 substituents which the "aromatic group which may be substituted" mentioned above may have. When the number of substituents is two or more, those substituents may be the same as or different from one another.

Preferably, the "acyl" for Y includes, for example, a group of the formula: —(C═O)—$R^3$, —(C═O)—$OR^3$, —(C═O)—$NR^3R^4$ or —$SO_2$—$R^{3a}$ wherein each symbol is as defined above. More preferred are, for example, formyl, carboxy, $C_{1-6}$ alkoxy-carbonyl (e.g., methoxycarbonyl, ethoxycarbonyl, propoxycarbonyl, butoxycarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-10}$ aryl-carbamoyl (e.g., phenylcarbamoyl, naphthylcarbamoyl, etc.), $C_{1-6}$ alkylsulfonyl (e.g., methylsulfonyl, ethylsulfonyl, etc.), etc. Among others, especially preferred are carboxy, $C_{1-6}$ alkoxy-carbonyl, mono-$C_{1-6}$ alkyl-carbamoyl, di-$C_{1-6}$ alkyl-carbamoyl, etc.

The "hydroxy which may be substituted" for Y includes, for example, a hydroxy which may be substituted by the above-mentioned "hydrocarbon group which may be substituted", "acyl" or "aromatic heterocyclic group". Among others, preferred is the "hydrocarbon group which may be substituted". More preferred is $C_{1-6}$ alkyl, $C_{2-6}$ alkenyl, $C_{1-6}$ alkynyl, $C_{3-6}$ cycloalkyl, $C_{6-14}$ aryl or $C_{7-16}$ aralkyl, each of which may be substituted by 1 to 3 substituents. Especially preferred is a $C_{6-14}$ aryl (preferably phenyl) which may be substituted by 1 to 3 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{3-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{6-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{1-10}$ aryloxy and (20') oxo.

The "amino which may be substituted" for Y includes, for example, (i) an amino which may be substituted by 1 or 2 of 1 or 2 substituents selected from the group consisting of the above-mentioned "hydrocarbon group which may be substituted" and the above-mentioned "acyl", or (ii) a 5- to 7-membered saturated cyclic amino.

The "5- to 7-membered saturated cyclic amino" includes those described in detail in the foregoing referring to the substituents which the "hydrocarbon group which may be substituted" may have.

Preferred examples of the "amino which may be substituted" for Y include amino, mono-$C_{1-6}$ alkylamino (e.g., methylamino, ethylamino, etc.), di-$C_{1-6}$ alkylamino (e.g., dimethylamino, diethylamino, ethylmethylamino, etc.), 5- to 7-membered cyclic amino (e.g., morpholino, thiomorpholino, piperazin-1-yl, piperidino, pyrrolidin-1-yl, hexamethyleneimin-1-yl, etc.), $C_{1-6}$ alkyl-carboxamido (e.g., acetamido, etc.), $C_{6-10}$ aryl-carboxamido (e.g., phenylcarboxamido, naphthylcarboxamido, etc.), $C_{1-6}$ alkoxy-carboxamido (e.g., methoxycarboxamido, ethoxycarboxamido, propoxycarboxamido, butoxycarboxamido, etc.), N'-mono-$C_{1-6}$ alkyl-ureido (e.g., N'-methylureido, N'-ethylureido, etc.), N',N'-di-$C_{1-6}$ alkyl-ureido (e.g., N',N'-dimethylureido, N',N'-diethylureido, etc.), N'-mono-$C_{6-10}$ aryl-ureido (e.g., N'-phenylureido, N'-naphthylureido, etc.), etc.

The "aromatic group which may be substituted" for Y includes those described in detail in the foregoing referring to the substituents which the "hydrocarbon group which may be substituted" may have.

Preferably, Y is an acyl, a hydroxy which may be substituted, etc. More preferred is a hydroxy which may be substituted.

The above-mentioned "group of the formula: —X—Y" may be substituted at possible positions of the ring A.

The "5- to 8-membered ring" for the "5- to 8-membered ring which may be further substituted apart from the group of the formula: —X—Y wherein each symbol is as defined above" for ring A includes, for example, a 5- to 8-membered carbocyclic or heterocyclic ring which may contain a double bond apart from the double bond condensed with a quinone ring, and may contain 1 to 3 hetero atoms selected from the group consisting of nitrogen, sulfur and oxygen atoms in addition to carbon atoms. Concretely mentioned is a ring of the formula:

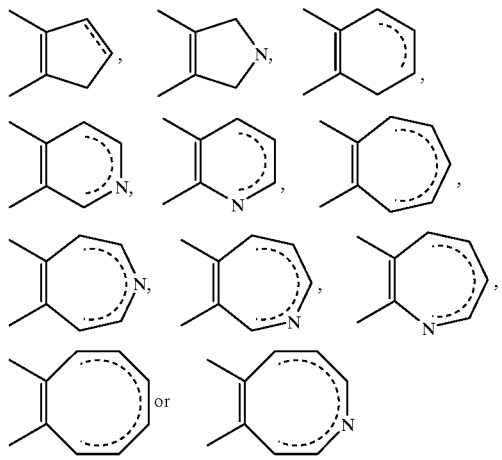

Among others, preferred is a 5- to 7-membered carbocyclic or heterocyclic ring which may contain one nitrogen atom in addition to carbon atoms.

More preferred is a ring of the formula:

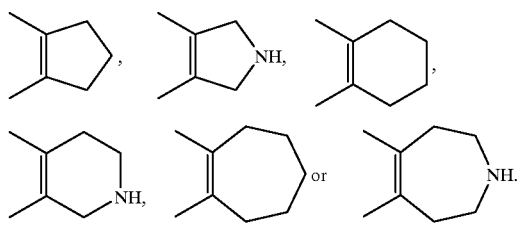

Especially preferred is a ring of the formula:

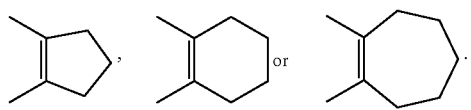

The "substituent" for the "5- to 8-membered ring which may be further substituted apart from the group of the formula: —X—Y wherein each symbol is as defined above" for ring A includes, for example, an acyl, a hydroxy which may be substituted, an amino which may be substituted, a hydrocarbon group which may be substituted, a heterocyclic group which may be substituted, an oxo, etc.

The above "acyl", "a hydroxy which may be substituted", "an amino which may be substituted", "a hydrocarbon group which may be substituted" and "a heterocyclic group which may be substituted" include those described above, respectively.

Preferred examples of the "substituent" includes carboxy, $C_{1-6}$ alkoxy-carbonyl, carbamoyl, mono-$C_{1-6}$ alkylamino-carbonyl, di-$C_{1-6}$ alkylamino-carbonyl, optionally hydroxylated $C_{1-6}$ alkyl, oxo, hydrocarbon group which may be substituted, etc.

Ring A may have 1 to 3 substituents mentioned above at possible positions of the ring and, when the number of substituents is two or more, those substituents may be the same as or different from one another. The above-mentioned substituents may be substituted at same position which is substituted by the group of the formula: —X—Y wherein each symbol is as defined above.

Ring A is preferably a ring of the formula:

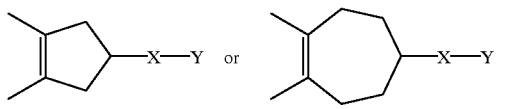

wherein each symbol is as defined above.

In compound (I), preferred compound is a compound wherein $R^1$ and $R^2$ each is $C_{1-6}$ alkyl;

X is (1) a $C_{2-8}$ alkylene or (2) a group of the formula: —(CH$_2$)m—X$^1$—, —(CH$_2$)m—X$^2$—X$^1$—, —X$^1$—X$^2$—(CH$_2$)n-, —X$^2$—X$^1$—(CH$_2$)n-, —(CH$_2$)m—X$^1$—(CH$_2$)n-, —(CH$_2$)m—X$^2$—(CH$_2$)n-, —(CH$_2$)m—X$^1$—X$^2$—(CH$_2$)n-, —(CH$_2$)m—X$^2$—X$^1$—(CH$_2$)n- or —X$^2$—X$^1$—X$^2$—(CH$_2$)n- wherein $X^1$ is a divalent $C_{6-14}$ aromatic hydrocarbon group (preferably 1,4-phenylene), $X^2$ is O, m is integer of 0 to 10, n is integer of 1 to 5, and m+n is an integer of 2 to 10;

Y is a hydroxy which may be substituted; and
ring A is a ring of the formula:

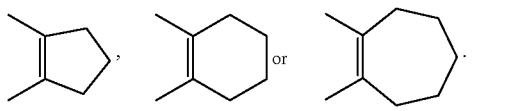

Among others, Y is preferably a hydroxy substituted by a phenyl which may be substituted by 1 to 3 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo.

Also preferred is a compound wherein $R^1$ and $R^2$ each is $C_{1-6}$ alkyl;

X is (1) $C_{1-8}$ alkylene or (2) a group of the formula: —(CH$_2$)m'—X$^2$'—X$^1$'—, —X$^1$'—X$^2$'—(CH$_2$)n'— or —(CH$_2$)m'—X$^2$'—X$^1$'—(CH$_2$)n'— wherein $X^{1'}$ is a 1,4-phenylene, $X^{2'}$ is O, m' is an integer of 1 to 4, and n' is 1 or 2;

Y is (1) a carboxy, (2) a carbonyl substituted by (i) a $C_{1-6}$ alkoxy, (ii) an amino, (iii) a mono- or di-$C_{1-6}$ alkylamino or (iv) a 6-membered saturated cyclic amino which may be substituted by a $C_{1-6}$ alkyl, a phenyl or a piperidino, (3) a hydroxy which may be substituted by (i) a phenyl which may be substituted by 1 to 3 substituents selected from the group consisting of halogen, $C_{1-3}$ alkylenedioxy, cyano, $C_{1-6}$ alkyl, $C_{1-6}$ alkoxy and mono-$C_{1-6}$ alkyl-carbamoyl, (ii) a $C_{1-6}$ alkyl-carbonyl, (iii) a mono- or di-$C_{1-6}$ alkyl-carbamoyl, (iv) a pyridyl or (v) quinolyl, (4) an amino substituted by 1 or 2 substituents selected from the group consisting of $C_{1-6}$ alkyl and $C_{1-6}$ alkyl-carbonyl, (5) a 6-membered saturated cyclic amino which may be substituted by (i) a phenyl, (ii) a benzyl which may be substituted by a phenyl, (iii) a piperidino or (iv) a pyridyl, (6) a phenyl, (7) a $C_{6-10}$ quinonyl substituted by 1 or 2 $C_{1-6}$ alkoxy, (8) a phthalimido, (9) a pyridyl which may be substituted by an oxo, (10) a quinolyl which may be substituted by an oxo, (11) benzotriazolyl or (12) a benzimidazolyl; and ring A is a ring of the formula:

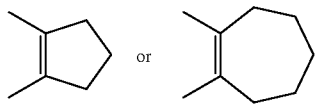

which may be further substituted by a carboxy, $C_{1-6}$ alkoxy-carbonyl, carbamoyl, mono- or di-$C_{1-6}$ alkylcarbamoyl, hydroxy-$C_{1-6}$ alkyl or phenyl.

In compound (I), more preferred is a compound of the formula:

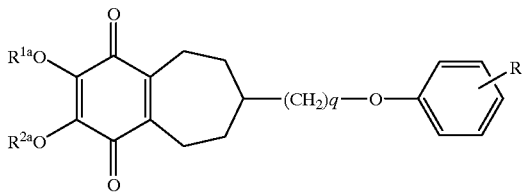

wherein $R^{1a}$ and $R^{2a}$ each is $C_{1-3}$ alkyl; q is an integer of 1 to 4; and R is 1 to 3 substituents selected from the group consisting of halogen, $C_{1-3}$ alkylenedioxy, cyano, optionally halogenated $C_{1-6}$ alkyl, optionally halogenated $C_{1-6}$ alkoxy, $C_{1-6}$ alkoxy-carbonyl, formylamino, $C_{1-6}$ alkyl-carboxamido, $C_{6-10}$ aryl-carboxamido, $C_{1-6}$ alkoxy-carboxamido and $C_{1-6}$ alkylsulfonylamino, or a salt thereof.

Especially preferred is 2-[8-(4-chlorophenoxy)octyl]-5,6-dimethoxyindan-4,7-dione, ethyl 4-[2-(2,3-dimethoxy-1,4-dioxo-4,5,6,7,8,9-hexahydro-1H-benzo[a]cyclohepten-7-yl)ethoxy]benzoate, or 7-[2-(4-chlorophenoxy)ethyl]-2,3-dimethoxy-4,5,6,7,8,9-hexahydro-1H-benzo[a]cycloheptene-1,4-dione, and so forth.

As the salts of compound (I), for example, metal salts, ammonium salts, salts with organic bases, salts with inorganic acids, salts with organic acids and salts with basic or acidic amino acids can be mentioned. Preferable examples of metal salts include alkali metal salts such as sodium salt and potassium salt; alkaline earth metal salts such as calcium salts, magnesium salts and barium salts; aluminum salts, etc. Preferred salts with organic bases are exemplified by salts with trimethylamine, triethylamine, pyridine, picoline, ethanolamine, diethanolamine, triethanolamine, dicyclohexylamine, N,N'-dibenzylethylenediamine, etc. Preferred salts with inorganic acids are exemplified by salts with hydrochloric acid, hydrobromic acid, nitric acid, sulfuric acid, phosphoric acid, etc. Preferred salts with organic acids are exemplified by salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferred salts with basic amino acids are exemplified by salts with arginine, lysine, ornithine, etc. Preferred salts with acidic amino acids are exemplified by salts with aspartic acid, glutamic acid, etc.

Among others, pharmaceutically acceptable salts are preferable. Preferable examples include, for example, when the compound (I) has a acidic functional group, alkali metal salts (e.g., sodium salt and potassium salt), alkaline earth metal salts (e.g., calcium salt, magnesium salt and barium salt), and ammonium salts; and when the compound (I) has a basic functional group, inorganic salts such as hydrochloride, sulfate, phosphate and hydrobromide, or, organic salts such as acetate, maleate, fumarate, succinate, methane-sulfonate, p-toluenesulfonate, citrate and tartrate.

Process for producing compound (I) are mentioned below.

Compound (I) can be produced using any per se known method, for example, the method shown in the following schemes.

The compounds in those schemes include their salts. As examples of the salts, referred to are the salts of compound (I) mentioned above.

Scheme 1

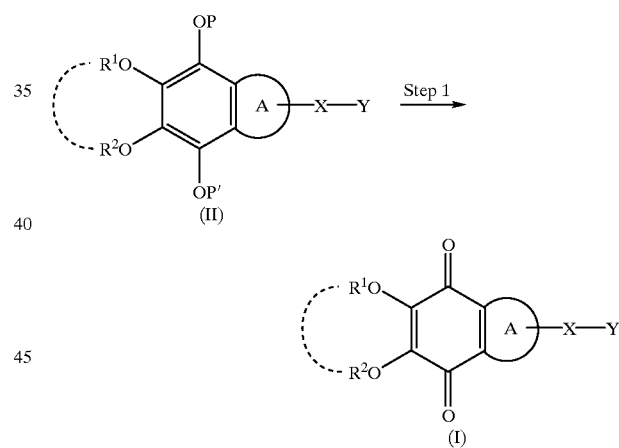

In those formulae, P and P' each represents a protective group; and the other symbols have the same meanings as above.

The "protective group" for P or P' may be any and every one generally used in the field of organic synthetic chemistry, provided that it does not interfere with the reaction. For example, employable are any protective groups that are stable in the intermediate production steps to be described hereinunder. Preferred are methyl and benzyl, etc.

(Step 1)

Compound (II) is subjected to quinone production reaction to obtain compound (I).

Compound (II) can be produced by any per se known methods, for example, the method of the following scheme 2 or analogous methods thereto.

In the step 1, the removal of P and P' from compound (II) and the oxidation of compound (II) can be effected simultaneously or separately.

For example, when P and P' each is methyl, compound (II) is reacted with a cerium compound [e.g., CAN (cerium(IV) ammonium nitrate), etc.] to give compound (I).

This reaction may be attained by stirring compound (II) with an excessive amount (preferably, 2 to 10 equivalents) of a cerium compound, in an inert solvent (e.g., mixed solvent of water and nitriles, etc.), at room temperature (0 to 30° C.) to 80° C., for 1 to 24 hours. If desired, this reaction Compound (I) obtained in the step 1 is optionally subjected to per se known deprotection, acylation, esterification, amination, amidation, hydrolysis or alkylation, or to combination of any two or more of those reactions, to obtain the intended products. These reactions may be attained, for example, according to the methods described in Comprehensive Organic Transformations, VCH Publishers Inc., 1989, written by Richard Larock, etc.

Scheme 2

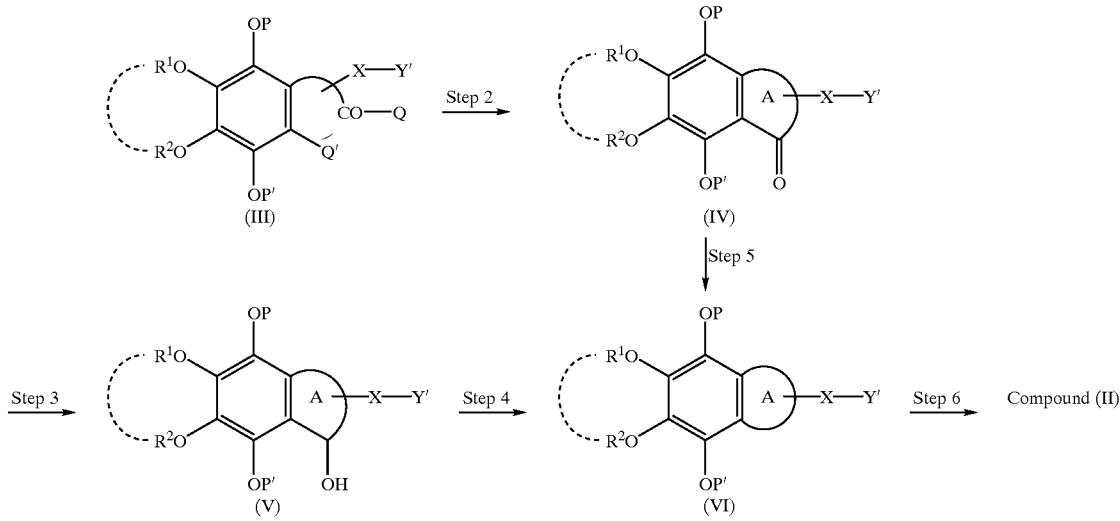

may be effected in the presence of a catalytic amount to 10 equivalents of a mineral acid (e.g., sulfuric acid, etc.) or an organic acid (e.g., 2,6-pyridine dicarboxylic acid, etc.).

Alternatively, compound (II) may be reacted with 2 to 10 equivalents of silver(II) oxide or a chromic acid reagent (e.g., pyridinium chlorochromate, Collins' reagent, etc.) by any per se known method, for example, the method described in Tetrahedron Letters, 94, 227 (1980), etc., to obtain compound (I).

For example, when P and P' each is benzyl, compound (II) may be subjected to per se known catalytic reduction to obtain its hydroquinone derivative [compound (IIa)], followed by subjecting the compound (IIa) which is optionally isolated, to per se known oxidation to obtain compound (I).

The catalytic reduction may be attained by reacting compound (II) with a catalytic amount of a metal catalyst (e.g., Raney nickel, platinum oxide, palladium metal, palladium-carbon, etc.), in alcohols, at 1 to 100 atmospheres, preferably 1 to 5 atmospheres in terms of hydrogen pressure, at room temperature to 100° C., for 1 to 48 hours.

The next oxidation step may be attained by stirring the compound (IIa) with 2 to 10 equivalents of an oxidizing agent, in an inert solvent, at room temperature to 50° C., for 1 to 24 hours.

The inert solvent includes, for example, water, ethers, halogenated hydrocarbons, etc. One or more of those solvents are employable either singly or as a suitable mixture of two or more species.

The oxidizing agent includes, for example, chromium compounds (e.g., chromic anhydride, Jones reagent, etc.), manganese compounds (e.g., manganese dioxide, potassium permanganate, etc.), silver oxide, ferric oxide, Fremy's salt, etc.). Preferred are ferric oxide, Fremy's salt, etc.

In these formulae, the group of the formula: —CO—Q represents a carboxylic acid or its reactive derivative; Q' represents a hydrogen or a halogen atom; Y' represents a group which may be converted into Y; and the other symbols have the same meanings as above.

Q preferably includes hydroxy, $C_{1-6}$ alkoxy (e.g., methoxy, ethoxy, propoxy, isopropoxy, butoxy, etc.), halogen (e.g., bromo, chloro, fluoro, etc.), $C_{6-10}$ aryloxy which may be substituted, $C_{7-12}$ aralkyloxy which may be substituted, $C_{1-6}$ alkyl-carbonyloxy (e.g., acetyloxy, propionyloxy, etc.), $C_{1-6}$ alkoxy-carbonyloxy (e.g., methoxycarbonyloxy, butoxycarbonyloxy, propoxycarbonyloxy, etc.), etc.

The "$C_{6-10}$ aryloxy" for the "$C_{6-10}$ aryloxy which may be substituted" includes, for example, phenyloxy, naphthyloxy, etc.

The "substituent" for the "$C_{6-10}$ aryloxy which may be substituted" includes, for example, 1 to 5 substituents selected from the group consisting of nitro and halogen, etc. As specific examples of the "$C_{6-10}$ aryloxy which may be substituted", mentioned are phenoxy, pentachlorophenyloxy, p-nitrophenyloxy, etc.

The "$C_{7-12}$ aralkyloxy" for the "$C_{7-12}$ aralkyloxy which may be substituted" includes, for example, benzyloxy, etc. The "substituents" for the "$C_{7-12}$ aralkyloxy which may be substituted" includes the "substituents" for the "$C_{6-10}$ aryloxy which may be substituted" mentioned above. As specific examples of the "$C_{7-12}$ aralkyloxy which may be substituted", mentioned are benzyloxy, p-chlorobenzyloxy, etc.

The "halogen atom" for Q' preferably includes bromo, chloro, etc.

Y' may be any and every group which can be converted into Y, including, for example, (i) "an acyl, a hydroxy which may be substituted, an amino which may be substituted or an aromatic group which may be substituted" such as that mentioned hereinabove for Y; and (ii) halogens, nitro, cyano, azido, silylated hydroxy, silylated amino, silylated carboxy and acetal-protected carbonyl, etc.

The "silyl" of the "silylated hydroxy", "silylated amino" and "silylated carboxy" includes, for example, trimethylsilyl, triethylsilyl, dimethylphenylsilyl, dimethyl-t-butylsilyl, diethyl-t-butylsilyl, etc.

The "acetal" of the "acetal-protected carbonyl" includes, for example, a cyclic acetal such as 1,3-dioxane, etc.; and an acyclic acetal such as di-$C_{1-6}$ alkylacetal, etc.

In the case that Y' is a halogen atom, it is converted, if desired, into an acyl, a hydroxy which may be substituted, an amino which may be substituted or the like, according to any per se known manner, for example, the methods described in Comprehensive Organic Transformations, 1989, mentioned above.

In the case that Y' is a nitro, cyano or azido, it is converted, if desired, into an amino by any per se known manner, for example, the methods described in Comprehensive Organic Transformations, 1989, mentioned above.

Y' preferably includes $C_{1-6}$ alkoxy-carbonyl (e.g., methoxycarbonyl, ethoxycarbonyl, propoxycarbonyl, etc.), silyloxy (e.g., trimethylsilyloxy, triethylsilyloxy, dimethylphenylsilyloxy, dimethyl-t-butylsilyloxy, diethyl-t-butylsilyloxy, etc.), phthalimido, etc.

(Step 2)

Compound (III) is subjected to per se known cyclization reaction to obtain compound (IV).

Compound (III) can be produced by any per se known methods, for example, the method of the following scheme 3 or analogous methods thereto.

For the cyclization reaction, for example, employable are the following two methods.

(1) Where Q' is a hydrogen atom in compound (III), for example, compound (III) is subjected to cyclization with an acid. Preferably, in the reaction, Q is hydroxy, halogen, etc.

This reaction may be attained by reacting compound (III) with a catalytic amount to an excessive amount, preferably 1 to 5 equivalents of an acid in an inert solvent, at −70 to 100° C., for 10 minutes to 24 hours.

The acid includes, for example, Lewis acids (e.g., aluminium chloride, stannic chloride, titanium tetrachloride, boron trifluoride diethyl etherate, etc.); mineral acids (e.g., sulfuric acid, polyphosphoric acid, etc.); organic acids (e.g., p-toluenesulfonic acid, trifluoromethanesulfonic acid, methanesulfonic acid, etc.); organic silicon derivatives (e.g., trifluoromethanesulfonic acid trimethylsilyl ether, etc.), etc.

The inert solvent includes, for example, halogenated hydrocarbons, aromatic solvents, etc., which may be used either singly or as a suitable mixture of two or more species.

(2) Where Q' is a halogen atom in compound (III), for example, compound (III) is cyclized through halogen-metal conversion using an organometallic reagent. In this reaction, Q is preferably $C_{1-6}$ alkoxy, phenyloxy, etc.

This reaction may be attained by reacting compound (III) with an excessive amount, preferably 1 to 5 equivalents of an organometallic reagent, in an inert solvent, at −120 to 50° C., preferably at −90 to −50° C., for 0.5 to 18 hours.

The organometallic reagent includes, for example, alkyl lithium (e.g., $C_{1-6}$ alkyl lithium such as methyl lithium, ethyl lithium, butyl lithium, sec-butyl lithium, tert-butyl lithium, etc.); aryl lithium (e.g., $C_{6-10}$ aryl lithium such as phenyl lithium, etc.); Grignard reagents (e.g., $C_{1-6}$ alkyl magnesium bromide such as methyl magnesium bromide, ethyl magnesium bromide, butyl magnesium bromide, sec-butyl magnesium bromide, tert-butyl magnesium bromide, etc.; $C_{6-10}$ aryl magnesium bromide such as phenyl magnesium bromide, etc.); alkyl zinc (e.g., $C_{1-6}$ alkyl zinc such as dimethyl zinc, diethyl zinc, dibutyl zinc, etc.); $C_{6-10}$ aryl sodium (e.g., phenyl sodium, etc.), etc.

The inert solvent includes, for example, ethers, aromatic solvents, etc., which may be used either singly or as a suitable mixture of two or more species. Preferred are ethyl ether, tetrahydrofuran (THF), 1,2-dimethoxyethane, etc.

(Step 3)

Compound (IV) is subjected to reduction to obtain compound (V).

The reduction may be effected in any per se known methods, for example, the reduction using a metal hydride or the catalytic reduction, etc, such as methods described in Organic Functional Group Preparations, 2nd Ed., Academic Press, Inc., etc.

For the reduction using a metal hydride, for example, compound (IV) is reacted with a metal hydride in an inert solvent.

The metal hydride includes, for example, lithium aluminiumhydride, sodium borohydride, lithium borohydride, sodium cyanoborohydride, diborane, dibutyl aluminium hydride, etc. Among others, preferred are a metal hydride such as lithium aluminium hydride, etc.

The amount of the metal hydride to be used is 1 to 20 equivalents, preferably 2 to 6 equivalents, relative to compound (IV). The reaction temperature in the reaction using a metal hydride is −70 to 100° C., preferably 0 to 50° C. The reaction time is 0.5 to 6 hours, preferably 0.5 to 2 hours.

The catalytic reduction may be attained by reacting compound (IV) with a catalytic amount of a metal catalyst (e.g., Raney nickel, platinum oxide, palladium metal, palladium-carbon, etc.) in an inert solvent (e.g., alcohols, etc.), under a hydrogen pressure of 1 to 100 atmospheres, at room temperature to 100° C., for 1 to 48 hours.

(Step 4)

Compound (V) is subjected to reductive dehydration to obtain compound (VI).

The reductive dehydration may be effected by any per se known methods for catalytic reduction, methods using an organic silyl reagent (e.g., alkylsilane reagent, etc.), etc.

The catalytic reduction may be attained by reacting compound (V) with a catalytic amount of a metal catalyst (e.g., Raney nickel, platinum oxide, palladium metal, palladium-carbon, etc.) in an inert solvent (e.g., alcohols, etc.), under a hydrogen pressure of 1 to 100 atmospheres, at room temperature to 100° C., for 1 to 48 hours. If desired, a catalytic amount to an excessive amount of an organic acid (e.g., acetic acid, etc.) or a mineral acid (e.g., hydrochloric acid, etc.) may be added to the reaction system.

In the method of using an alkylsilane reagent, compound (V) may be reacted with an alkyl silane reagent and an acid, in an inert solvent (e.g., halogenated hydrocarbons), at 0 to 100° C., preferably 0 to 30° C., for 10 minutes to 24 hours.

The alkylsilane reagent includes, for example, triethylsilane, phenyldimethylsilane, etc.

The amount of the alkylsilane reagent to be used is 1 to 10 equivalents, preferably 1 to 5 equivalents, relative to compound (V).

The acid includes, for example, an organic acid (e.g., trifluoroacetic acid, etc.), etc.

The amount of the acid to be used is a catalytic amount to an excessive amount, preferably 1 to 5 equivalents, relative to compound (V).

(Step 5)

Compound (IV) is subjected to reduction to obtain compound (VI).

The reduction may be attained, for example, by methods using metals. For example, compound (IV) is stirred along with an excessive amount (1 to 100 equivalents) of a metal (e.g., zinc powder, etc.), in an inert solvent (e.g., ethers, acetic acid, etc.), at room temperature to 100° C. for 1 to 24 hours.

(Step 6)

Compound (VI) is subjected to per se known organic synthetic reaction to obtain compound (II).

The organic synthetic reaction includes, for example, ether formation, deprotection, oxidation, reduction, alkylation, acylation, amination, hydroxylation, hydrolysis, etc. These reactions may be effected, for example, according to the methods described in Comprehensive Organic Transformations, 1989, mentioned above, etc.

For example, where Y' is a halogen atom in compound (VI), it may be substituted by a nitrogen or oxygen atom through substitution reaction.

The "reaction for substitution with nitrogen" may be attained by stirring compound (VI) with one equivalent to an excessive amount, preferably 1 to 5 equivalents of an amine, in no solvent or in an inert solvent, at room temperature to 200° C., preferably at 50 to 100° C., for 0.5 to 18 hours.

The amine includes, for example, ammonia, mono-$C_{1-6}$ alkylamine (e.g., methylamine, ethylamine, etc.), di-$C_{1-6}$ alkylamine (e.g., dimethylamine, diethylamine, etc.), 5- to 7-membered cyclic amine (e.g., morpholine, piperazine, piperidine, pyrrolidine, hexamethyleneimine, etc.), etc.

The inert solvent includes, for example, alcohols, ethers, amides, nitrites, etc., which may be used either singly or as a suitable mixture of two or more species.

The "reaction for substitution with oxygen" may be attained, for example, by (1) a method of reacting compound (VI) with one equivalent to an excessive amount, preferably 1.5 to 10 equivalents of a metal salt of an organic acid (e.g., sodium acetate, potassium acetate, silver acetate, etc.) in an inert solvent (e.g., alcohols, etc.), at room temperature to 100° C., for 0.5 to 24 hours to give an acyloxy compound; or (2) a method of reacting compound (VI) with one equivalent to an excessive amount, preferably 1.1 to 10 equivalents of an alkali metal compound (e.g., sodium hydroxide, potassium hydroxide, etc.) or silver oxide, in an inert solvent (e.g., water, alcohols or mixed solvents thereof, etc.), at room temperature to 100° C., for 0.5 to 24 hours to give a hydroxy compound.

For example, where Y' is an nitro or an azido in compound (VI), the compound (VI) may be subjected to per se known reduction to convert Y' into an amino group.

Where Y' is a hydroxy or an amino in compound (VI), compound (VI) may be subjected to per se known alkylation or acylation to obtain the intended compounds.

Concretely, compound (VI) is reacted with 1 to 3 equivalents, preferably 1.1 to 2 equivalents of a compound of the formula: L-Y", wherein L represents a leaving group, and Y" represents an acyl or a hydrocarbon group which may be substituted, in an inert solvent.

Where Y" is an acyl, the "leaving group" for L includes, for example, halogen atoms (e.g., chloro, bromo, iodo, etc.), $C_{1-4}$ alkylsulfonyloxy which may be substituted by 1 to 3 halogens (e.g., methanesulfonyloxy, trifluoromethanesulfonyloxy, etc.), $C_{6-10}$ arylsulfonyloxy which may be substituted by 1 to 4 halogens or $C_{1-6}$ alkyl (e.g., p-toluenesulfonyloxy, benzenesulfonyloxy, p-bromobenzenesulfonyloxy, etc.), $C_{1-6}$ alkyl-carbonyloxy (e.g., methylcarbonyloxy, ethylcarbonyloxy, propylcarbonyloxy, butylcarbonyloxy, etc.), $C_{1-6}$ alkoxycarbonyloxy (e.g., methoxycarbonyloxy, ethoxycarbonyloxy, propoxycarbonyloxy, butoxycarbonyloxy, etc.), phenoxycarbonyloxy, etc.

Where Y" is a hydrocarbon group which may be substituted, the "leaving group" for L includes, for example, halogen atoms, $C_{1-4}$ alkylsulfonyloxy which may be substituted by 1 to 3 halogens, $C_{6-10}$ arylsulfonyloxy group which may be substituted by 1 to 4 halogens, etc.

For the "acyl" for Y", referred to are the same as those for the "acyl" for Y.

For the "hydrocarbon group which may be substituted" for Y", referred to are the same as those for the "hydrocarbon group which may be substituted" of the "substituents" described in detail above for the "hydroxy group which may be substituted" or the "amino group which may be substituted" for Y.

The inert solvent includes, for example, water, alcohols, ethers, halogenated hydrocarbons, aromatic solvents, nitrites, amides, ketones, sulfoxides, etc., which may be used either singly or as a suitable mixture of two or more species. Of those, preferred are ethanol, acetonitrile, DMF, acetone, etc.

The reaction temperature is room temperature to 100° C., preferably room temperature to 50° C. The reaction time is 0.5 to 24 hours.

If desired, 1 to 3 equivalents of a base may be added to the reaction. The base is not always indispensable for the alkylation of the amino group.

The base includes, for example;

(1) strong bases such as alkali metal or alkaline earth metal hydrides (e.g., lithium hydride, sodium hydride, potassium hydride, calcium hydride, etc.), alkali metal or alkaline earth metal amides (e.g., lithium amide, sodium amide, lithium diisopropylamide, lithium dicyclohexylamide, lithium hexamethylsilazide, sodium hexamethylsilazide, potassium hexamethylsilazide, etc.), alkali metal or alkaline earth metal lower-alkoxides (e.g., sodium methoxide, sodium ethoxide, potassium t-butoxide, etc.), etc.;

(2) inorganic bases such as alkali metal or alkaline earth metal hydroxides (e.g., sodium hydroxide, potassium hydroxide, lithium hydroxide, barium hydroxide, etc.), alkali metal or alkaline earth metal carbonates (e.g., sodium carbonate, potassium carbonate, cerium carbonate, etc.), alkali metal or alkaline earth metal hydrogencarbonates (e.g., sodium hydrogencarbonate, potassium hydrogencarbonate, etc.), etc.; or (3) organic bases such as amines, e.g., triethylamine, dllsopropylethylamine, N-methylmorpholine, dimethylaminopyridine, DBU (1,8-diazabicyclo [5.4.0]-7-undecene), DBN (1,5-diazabicyclo[4.3.0] non-5-ene), etc., basic heterocyclic compounds, e.g., pyridine, imidazole, 2,6-lutidine, etc.

In compound (VI) where Y' is a $C_{1-6}$ alkoxy-carbonyl or $C_{6-10}$ aryloxy-carbonyl, the group Y' may be converted into a hydroxymethyl through reduction.

The reduction may be effected by any per se known methods, for example, the methods described in Comprehensive Organic Transformations, 1989, mentioned above, etc. For example, the compound (VI) is reacted with 1 to 20 equivalents, preferably 2 to 6 equivalents of a metal hydride in an inert solvent.

The metal hydride includes, for example, aluminium hydride, lithium aluminium hydride, sodium borohydride, lithium borohydride, sodium cyanoborohydride, diborane, dibutyl aluminium hydride, etc. Among others, preferred is lithium aluminium hydride.

The inert solvent includes, for example, ethers (preferably, THF, ethyl ether, etc.), alcohols, aromatic solvents (preferably, toluene), hydrocarbons (preferably, hexane), etc., which may be used either singly or as a suitable mixture of two or more species.

The reaction temperature is −70 to 100° C. The preferred reaction temperature varies, depending on the reducing agent used. For example, when lithium aluminium hydride is used, the preferred reaction temperature is room temperature to 50° C.

In compound (VI) where Y' is a carbamoyl or a N-substituted carbamoyl, the group Y' may be converted into the corresponding aminomethyl or N-substituted aminomethyl, respectively through reduction.

For example, where Y' is a carbamoyl, mono-N-$C_{1-6}$ alkyl-carbamoyl or di-N-$C_{1-6}$ alkyl-carbamoyl, the compound (VI) is subjected to reduction whereby the group Y' is converted into an aminomethyl, mono-N-$C_{1-6}$ alkylaminomethyl or di-N-$C_{1-6}$ alkylaminomethyl, respectively.

For the reduction, concretely, the compound (VI) is reacted with 1 to 20 equivalents, preferably 2 to 6 equivalents of a metal hydride in an inert solvent.

The metal hydride includes, for example, aluminium hydride, lithium aluminium hydride, sodium borohydride, lithium borohydride, sodium cyanoborohydride, diborane, dibutyl aluminium hydride, etc. Among others, preferred is lithium aluminium hydride.

The inert solvent includes, for example, ethers (preferably, THF, ethyl ether, etc.), alcohols, aromatic solvents (preferably, toluene), hydrocarbons (preferably, hexane), etc., which may be used either singly or as a suitable mixture of two or more species.

The reaction temperature is −70 to 100° C. The preferred reaction temperature varies, depending on the reducing agent used. For example, when lithium aluminium hydride is used, the preferred reaction temperature is 40 to 80° C.

In compound (VI) where Y' is an acyl which can be hydrolyzed (e.g., $C_{1-6}$ alkoxy-carbonyl, $C_{6-10}$ aryloxycarbonyl, etc.), the group Y' may be converted into a carboxy through hydrolysis.

The hydrolysis may be effected in accordance with any per se known alkali hydrolysis and acid hydrolysis.

For the alkali hydrolysis, the compound (VI) is reacted with an alkali in an inert solvent.

The alkali includes, for example, alkali metal or alkaline earth metal hydroxides, such as lithium hydroxide, sodium hydroxide, potassium hydroxide, barium hydroxide, etc. Of those, preferred is sodium hydroxide.

The amount of the alkali to be used is 2 to 100 equivalents, preferably 5 to 10 equivalents, relative to compound (VI).

The inert solvent includes, for example, water, alcohols, ethers, etc., which may be used either singly or as a suitable mixture of two or more species. Of those, preferred is a mixed solvent of water-methanol.

The reaction temperature is 10 to 120° C., preferably 50 to 120° C. The reaction time is 0.5 to 100 hours, preferably 1 to 50 hours.

In one preferred example of the reaction, the inert solvent to be used is a mixed solvent of water-methanol, the reaction temperature is 50 to 120° C., and the reaction time is 1 to 10 hours.

The acid hydrolysis may be effected, for example, by stirring the compound (VI) with an excessive amount, preferably 1 to 10 equivalents of a mineral acid (e.g., hydrochloric acid, sulfuric acid, phosphoric acid, etc.) in a solvent, at room temperature to 120° C., preferably at 60 to 100° C., for 0.5 to 18 hours.

The solvent may be a mixture of water and an organic acid (e.g., acetic acid, etc.). Preferably used is diluted hydrochloric acid alone or along with acetic acid.

For the compound (I) where ring A is a 5-membered carbocyclic ring, for example, first is obtained compound (VI') according to the following scheme 3, and thereafter the compound (VI') may be processed in accordance with the step 6 mentioned above to obtain compound (II'). Compound (II') is within the scope of compound (II).

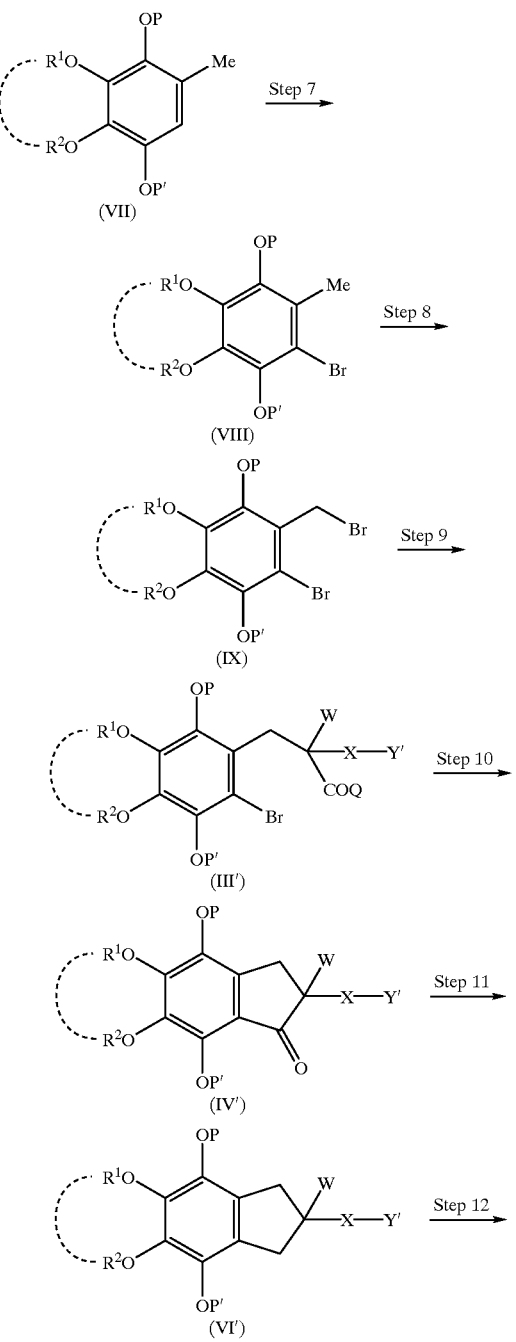

Scheme 3

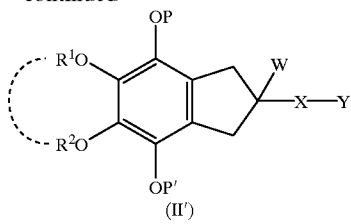

In these formulae, the symbols have the same meanings as above.

(Step 7)

Compound (VII) is subjected to bromination to obtain compound (VIII).

Compound (VII) is an easily-available, known compound, and can be produced by per se known methods, for example, the methods described in the Journal of Organic Chemistry, 54, 3872 (1987), etc.

Briefly, compound (VII) is reacted with 1 to 1.5 equivalents of a brominating reagent (e.g., bromine, N-bromosuccinimide (NBS), etc.), in an inert solvent (e.g., halogenated hydrocarbons, esters, acetic acid, mixed solvents thereof, etc.), at −20 to 100° C., preferably at 0° C. to room temperature, for 0.1 to 18 hours.

(Step 8)

Compound (VIII) is subjected to radical bromination to obtain compound (IX).

Briefly, compound (VIII) is reacted with 1 to 1.5 equivalents of a brominating reagent (e.g., NBS, etc.) in the presence of a catalytic amount to 1 equivalent of a radical-generating agent (e.g., perbenzoic acid, 2,2'-azobis (isobutyronitrile) (AIBN), etc.), in an inert solvent (e.g., ethyl acetate, halogenated hydrocarbons, etc.), at room temperature to 100° C., preferably at 50 to 80° C., for 0.1 to 18 hours.

(Step 9)

Compound (IX) is reacted with compound (X) of the formula:

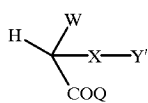

wherein W represents hydrogen, nitro, an acyl, a hydroxy which may be substituted, an amino which may be substituted, a hydrocarbon group which may be substituted, or a heterocyclic group which may be substituted; and the other symbols have the same meanings as above, in an inert solvent to obtain compound (III').

For the "acyl", the "hydroxy which may be substituted", the "amino which may be substituted", the "hydrocarbon group which may be substituted" and the "heterocyclic group which may be substituted" for W, referred to are the same as those mentioned in detail above for the substituents which ring A may have.

In this reaction, Q is preferably $C_{1-6}$ alkoxy, benzyloxy or the like.

The amount of compound (X) to be used is 1 to 1.5 equivalents relative to compound (IX).

The reaction temperature is room temperature to 100° C., preferably room temperature to 50° C. The reaction time is 0.5 to 24 hours. In general, 1 to 3 equivalents of a base is added to the reaction system.

The inert solvent includes, for example, alcohols, ethers, halogenated hydrocarbons, aromatic solvents, nitrites, amides, ketones, sulfoxides, etc., which may be used either singly or as a suitable mixture of two or more species. Among others, preferred are acetonitrile, DMF, acetone, ethanol, etc.

The base includes, for example;
(1) strong bases such as alkali metal or alkaline earth metal hydrides (e.g., lithium hydride, sodium hydride, potassium hydride, calcium hydride, etc.), alkali metal or alkaline earth metal amides (e.g., lithium amide, sodium amide, lithium diisopropylamide, lithium dicyclohexylamide, lithium hexamethylsilazide, sodium hexamethylsilazide, potassium hexamethylsilazide, etc.), alkali metal or alkaline earth metal lower-alkoxides (e.g., sodium methoxide, sodium ethoxide, potassium t-butoxide, etc.), etc.;
(2) inorganic bases such as alkali metal or alkaline earth metal hydroxides (e.g., sodium hydroxide, potassium hydroxide, lithium hydroxide, barium hydroxide, etc.), alkali metal or alkaline earth metal carbonates (e.g., sodium carbonate, potassium carbonate, cerium carbonate, etc.), alkali metal or alkaline earth metal hydrogencarbonates (e.g., sodium hydrogencarbonate, potassium hydrogencarbonate, etc.), etc.; or
(3) amines such as triethylamine, diisopropylethylamine, N-methylmorpholine, dimethylaminopyridine, DBU (1,8-diazabicyclo[5.4.0]-7-undecene), DBN (1,5-diazabicyclo[4.3.0]non-5-ene), etc., basic heterocyclic compounds, as well as aromatic amines, for example, basic heterocyclic compounds such as pyridine, imidazole, 2,6-lutidine, etc.

(Step 10)

Compound (III') is subjected to reduction to obtain compound (IV').

Briefly, compound (III') is cooled in ethers (preferably, THF, ethyl ether, etc.) to between −100 and −60° C., and 1 to 2 equivalents, preferably 1 to 1.2 equivalents, of an alkali metal reagent is added thereto and stirred at −100 to −20° C. for 0.5 to 6 hours.

The alkali metal reagent includes, for example, alkyl lithium, aryl lithium, Grignard reagents, alkyl zinc, $C_{6-10}$ aryl sodium, etc., such as those mentioned above for the step 2.

(Step 11)

Compound (IV') is subjected to reduction to obtain compound (VI').

The reduction may be effected by combining the steps 3, 4 and 5.

For example, for the first stage reduction of the ketone to the corresponding hydroxy, employable is a method of reacting compound (IV') with 1 to 10 equivalents of sodium borohydride in alcohols at 0 to 50° C., preferably at room temperature, for 0.5 to 18 hours. For the reductive dehydration in the second stage, for example, preferred is catalytic reduction such as that for the above-mentioned step 4. Especially preferably, compound (IV') is reacted with a palladium-carbon catalyst, while being stirred therewith in alcoholics under a hydrogen pressure of 1 to 5 atmospheres for 1 to 18 hours.

Compound (VI') obtained in the step 11 where W is $C_{1-6}$ alkoxy-carbonyl may be subjected to decarboxylation, if desired.

The decarboxylation may be effected under an acidic condition, for example, by reacting compound (VI') with an organic acid (e.g., acetic acid, etc.) or a mineral acid (preferably, sulfuric acid, hydrochloric acid, perchloric acid, etc.), at room temperature to 100° C., preferably at 60 to 100° C., for 1 to 24 hours.

(Step 12)

In the same manner as in the step 6, compound (VI') is converted into compound (II').

For the compound (I) where ring A is a 6-membered nitrogen-containing ring, compound (II") may be obtained, for example, according to the following scheme 4. Compound (II") is within the scope of compound (II).

Scheme 4

(XI)

(XII)

(XIII)

(XIV)

(XV)

(XVI)

-continued (II")

In these formulae, the symbols have the same meanings as above.

(Step 13)

Compound (XI) is subjecting to acylation to obtain compound (XII).

The acylation may be attained by subjecting compound (XI) to halogen-metal conversion under the same condition as in the step 2, then adding thereto 1 equivalent to an excessive amount, preferably 1 to 1.5 equivalents of ethyl chlorocarbonate, and reacting the two with stirring them at the defined reaction temperature or at room temperature, for 1 to 15 hours. Preferably, the reaction temperature is −70 to −20° C.

(Step 14)

Compound (XII) is subjected to bromination to obtain compound (XIII).

The bromination may be effected under the same condition as in the step 8.

(Step 15)

Compound (XIII) is subjected to cyanation to obtain compound (XIV).

Briefly, compound (XIII) is stirred with 1 to 5 equivalents of a cyanating agent (e.g., sodium cyanide, potassium cyanide, etc.) in an inert solvent (e.g., DMF, DMSO, water, etc.) at room temperature to 100° C., preferably at 40 to 70° C., for 1 to 18 hours, preferably for 2 to 5 hours.

(Step 16)

Compound (XIV) is subjected to cyclization to obtain compound (XV).

For the cyclization, generally employed is catalytic reduction. Briefly, compound (XIV) is reacted with a catalytic amount of a metal catalyst (e.g., Raney nickel, platinum oxide, palladium metal, palladium-carbon, etc., preferably Raney nickel) in an inert solvent (e.g., ethanol saturated with ammonia), under a hydrogen pressure of 1 to 100 atmospheres, at room temperature to 100° C., for 1 to 48 hours. Preferably, the reaction is effected under a hydrogen pressure of 4 to 10 atmospheres, at 40 to 100° C. for 1 to 10 hours.

(Step 17)

Compound (XV) is subjected to reduction to obtain compound (XVI).

For the reduction, preferably used are various metal hydride reagents. For example, for this, usable are the metal hydrides referred to hereinabove for the step 3. Preferably, compound (XV) is reduced with an excessive amount of a metal hydride such as lithium aluminium hydride, aluminium hydride, diborane or the like, in ethers such as THF, etc.

(Step 18)

In the same manner as in the step 6, compound (XVI) is processed to obtain compound (II').

For the compound (I) where ring A is a 7-membered carbocyclic ring, for example, first is obtained compound (VI") according to the following scheme 5, and thereafter the compound (VI") may be processed in accordance with the-step 6 mentioned above to obtain compound (III'''). Compound (II''') is within the scope of compound (II).

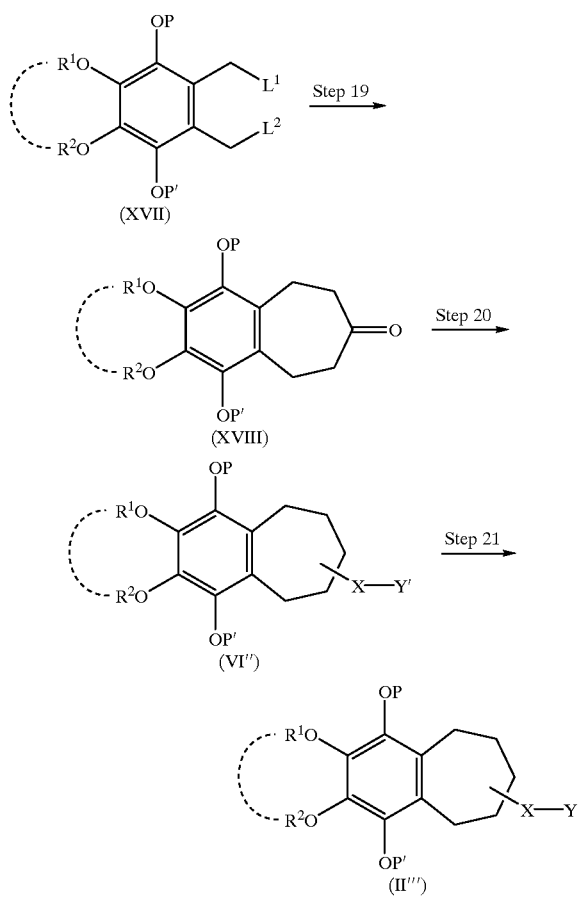

In these formulae, $L^1$ and $L^2$ each represents a leaving group, and the other symbols have the same meanings as above.

The "leaving group" for $L^1$ or $L^2$ includes, for example, the "leaving group" for L mentioned above. Preferably, $L^1$ and $L^2$ each is, for example, halogen atoms (e.g., chloro, bromo, iodo, etc.), $C_{1-4}$ alkylsulfonyloxy which may be substituted by 1 to 3 halogens (e.g., methanesulfonyloxy, trifluoromethanesulfonyloxy, etc.), $C_{6-10}$ arylsulfonyloxy which may be substituted by 1 to 4 substituents selected from the group consisting of $C_{1-6}$ alkyl and halogen (e.g., p-toluenesulfonyloxy, benzenesulfonyloxy, p-bromobenzenesulfonyloxy, etc.).
(Step 19)

Compound (XVII) is subjected to 7-membered ring formation reaction followed by decarboxylation to obtain compound (XVIII).

Compound (VII) is produced by per se known methods, for example, the methods described in Chemish Berichte, 1879 (1957), Journal of Chemical Society, 426 (1966), etc. For example, compound (VII) where P, P', $R^1$ and $R^2$ each is methyl, and $L^1$ and $L^2$ each is chloro can be obtained according to the methods described in Chemish Berichte, 1879 (1957). For example, compound (VII) where P, P', $R^1$ and $R^2$ each is methyl, and $L^1$ and $L^2$ each is bromo can be obtained according to Journal of Chemical Society, 426 (1966).

The above 7-membered ring formation reaction may be attained by reacting compound (XVII) with 0.5 to 1.5 equivalents of diethyl 1,3-acetonedicarboxylate in an inert solvent and in the presence of a base.

The base includes, for example, the above-described strong bases, inorganic bases and organic bases, etc. Among others, preferred are inorganic bases. More preferred are alkali metal or alkaline earth metal hydroxides (e.g., sodium hydroxide, potassium hydroxide, lithium hydroxide, barium hydroxide, etc.), alkali metal or alkaline earth metal carbonates (e. g., sodium carbonate, potassium carbonate, cerium carbonate, etc.), etc.

The amount of the base to be used is at least 2 equivalents, preferably 2 to 4 equivalents, relative to diethyl 1,3-acetonedicarboxylate.

The inert solvent includes, for example, water, alcohols, ethers, halogenated hydrocarbons, aromatic solvents, nitriles, amides, ketones, sulfoxides, etc., which may be used either singly or as a suitable mixture of two or more species. Of those, preferred are nitriles such as acetonitrile, etc.

The reaction temperature is room temperature to 100° C., preferably room temperature. The reaction time is 0.1 to 24 hours.

Next, thus obtained crude product is subjected to decarboxylation to obtain compound (XVIII).

The decarboxylation may be effected in any per se known methods. For example, the crude product is reacted with an excessive amount, preferably 1 to 10 equivalents, of mineral acid (e.g., hydrochloric acid, sulfuric acid, phosphoric acid, etc.) in an inert solvent.

The inert solvent may be a mixture of water and an organic acid (e.g., acetic acid, etc.). Preferably, this reaction is carried out in a diluted hydrochloric acid alone or a mixture of diluted hydrochloric acid with an acetic acid.

The reaction temperature is room temperature to 120° C., preferably 60 to 120° C. The reaction time is 0.5 to 24 hours. (Step 20)

The obtained compound (XVIII) is subjected to any per se known methods, for example, the method of the following scheme 6 or analogous methods thereto, etc. to obtain compound (VI'').

For example, compound (VI''') which is compound (VI'') where X is an alkylene can be produced by the method of the following scheme 6.
(Step 21)

In the same manner as in the step 6, compound (VI'') is processed to obtain compound (II''').

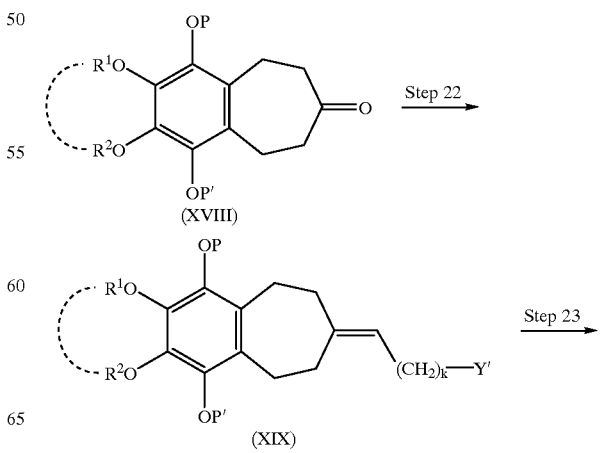

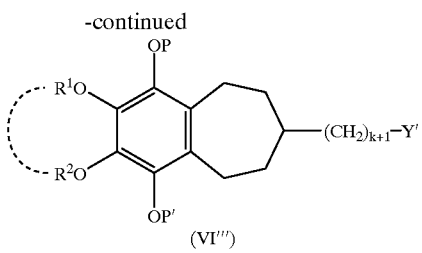

(VI''')

In these formulae, k represents an integer of 0 to 14, and the other symbols have the same meanings as above.

(Step 22)

Compound (XVIII) is subjected to Wittig reaction to obtain compound (XIX).

In this reaction, k is preferably an integer 0 to 10. Y' is preferably an acyl, more preferably carboxy or $C_{1-6}$ alkoxycarbonyl.

The Wittig reaction may be attained by reacting compound (XVIII) with a Wittig reagent in an inert solvent and in the presence of a base.

Compound (VII) is commercially available, and can be produced by per se known methods, for example, the methods described in Journal of Medicinal Chemistry, 28, 287 (1985), etc.

The amount of the Wittig reagent to be used is at least 1, preferably 1 to 2 equivalents, relative to compound (XVIII).

The base includes, for example, the above-described strong bases, inorganic bases and organic bases, etc. Among others, preferred are strong bases. More preferred is sodium hydride, lithium diisopropylamide, lithium dicyclohexylamide, sodium methoxide, sodium ethoxide, potassium t-butoxide, etc.

The amount of the base to be used is at least one equivalent relative to the Wittig reagent. In the case that the Wittig reagent has no carboxy nor hydroxy, the amount of the base is preferably 1 to 2 equivalents relative to the Wittig reagent. In the case that the Wittig reagent has a carboxy or hydroxy, the amount of the base is preferably 2 to 4 equivalents relative to the Wittig reagent.

The inert solvent includes, for example, water, alcohols, ethers, halogenated hydrocarbons, aromatic solvents, nitriles, amides, ketones, sulfoxides, etc., which may be used either singly or as a suitable mixture of two or more species. Of those, preferred is ethanol, toluene, DMF, etc.

The reaction temperature is room temperature to 100° C., preferably room temperature to 50° C. The reaction time is 0.5 to 24 hours.

(Step 23)

Compound (XIX) is subjected to catalytic reduction to obtain compound (VI''').

The catalytic reduction may be attained by reacting compound (XIX) with a catalytic amount of a metal catalyst (e.g., Raney nickel, platinum oxide, palladium metal, palladium-carbon, etc.), in an inert solvent, at 1 to 100 atmospheres in terms of hydrogen pressure.

The inert solvent includes, for example, water, alcohols, ethers, esters, halogenated hydrocarbons, aromatic solvents, nitriles, amides, etc., which may be used either singly or as a suitable mixture of two or more species. Of those, preferred is methanol, ethanol, ethyl acetate, etc.

The reaction temperature is room temperature to 100° C. The reaction time is 1 to 48 hours.

For the compound (I) where Y and a fused ring in which ring A is condensed with the quinone ring are indan-4,7-dione, respectively, for example, compound (II'''') can also be obtained according to the following scheme 7. Compound (II'''') is within the scope of compound (II).

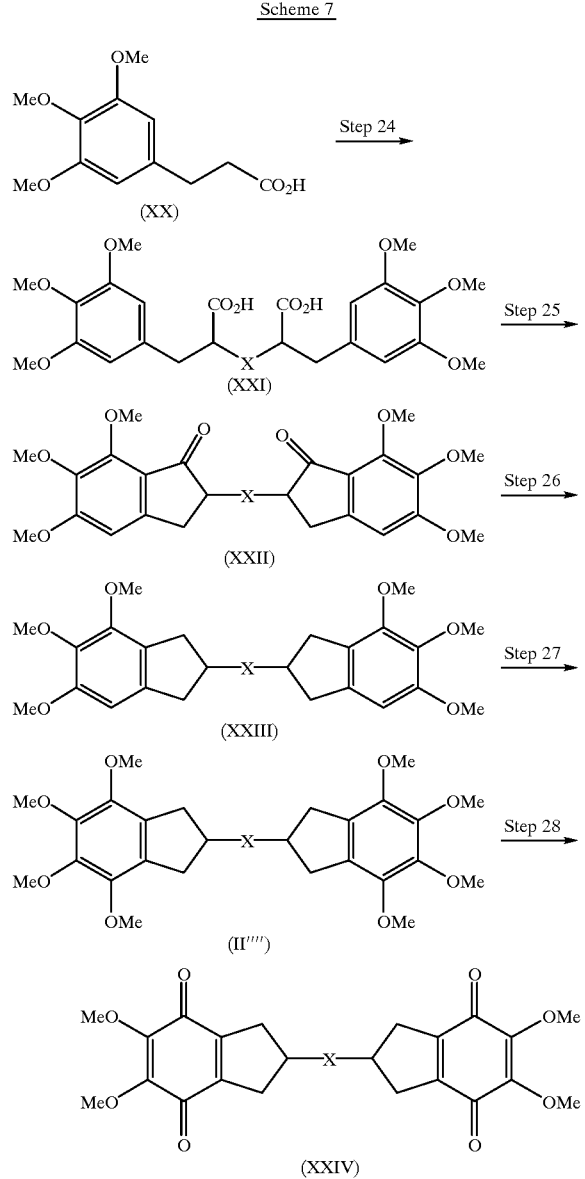

Scheme 7

In these formulae, all symbols have the same meanings as above.

(Step 24)

Compound (XX) is reacted with a compound of the formula: $L^3$—X—$L^4$ wherein $L^3$ and $L^4$ each represents a leaving group, and X has the same meaning as above, in an inert solvent and a base, to obtain compound (XXI).

The "leaving group" for $L^3$ or $L^4$ includes, for example, the "leaving group" for L mentioned above. Preferably, $L^3$ and $L^4$ each is, for example, halogen atoms (e.g., chloro, bromo, iodo, etc.), $C_{1-4}$ alkylsulfonyloxy which may be substituted by 1 to 3 halogens (e.g., methanesulfonyloxy, trifluoromethanesulfonyloxy, etc.), $C_{6-10}$ arylsulfonyloxy which may be substituted by 1 to 4 substituents selected from the group consisting of $C_{1-6}$ alkyl and halogen (e.g., p-toluenesulfonyloxy, benzenesulfonyloxy, p-bromobenzenesulfonyloxy, etc.).

Compound (XX) can be commercially available.

The amount of compound (XX) to be used is 2 to 4, preferably 2 to 2.5 equivalents, relative to the compound of the formula: $L^3$—X—$L^4$.

The base includes, for example, the above strong base and the above organometallic reagent, etc. Of those, preferred is lithium dlisopropylamide, lithium dicyclohexylamide, butyl lithium. sec-butyl lithium, tert-butyl lithium, etc.

The amount of the base to be used is at least 2, preferably 2 to 3 equivalents, relative to compound (XX).

The inert solvent includes, for example, ethers, halogenated hydrocarbons, aromatic solvents, amides, sulfoxides, etc., which may be used either singly or as a suitable mixture of two or more species. Of those, preferred is THF alone or a mixture of THF and DMF or DMSO, etc.

The reaction temperature is −70° C. to room temperature, preferably −20 to 30° C. The reaction time is 0.5 to 24 hours.
(Step 25)

Compound (XXI) is subjected to intramolecular Friedel-Crafts reaction to obtain compound (XXII).

The intramolecular Friedel-Crafts reaction may be attained, for example, according to the methods described in Organic Functional Group Preparations, the second edition, Academic press, Inc., etc. Among others, preferred is the reaction using a polyphosphoric acid. In this case, the excessive amount, preferably 5 to 50 equivalents of the polyphosphoric acid is used.

The reaction temperature is room temperature to 100° C., preferably 50 to 100° C. The reaction time is 0.5 to 24 hours.
(Step 26)

Compound (XXII) is subjected to reduction to obtain compound (XXIII).

The reduction may be attained by the catalytic reduction or the combination of the above step 3 with the step 4.

The catalytic reduction may be attained by reacting compound (XXII) with a catalytic amount of a metal catalyst (e.g., Raney nickel, platinum oxide, palladium metal, palladium-carbon, etc.) in an inert solvent (e.g., organic acid such as acetic acid, alcohols, etc.) under a hydrogen pressure of 1 to 100 atmospheres.

The reaction temperature is room temperature to 100° C. The reaction time is 1 to 48 hours. If desired, a catalytic amount to 1 equivalent of a mineral acid (e.g., perchloric acid, hydrochloric acid, etc.) may be added to the reaction system.
(Step 27)

Compound (XXIII) is subjected to bromination and followed by substitution of the bromo by a methoxy to obtain compound (II'''').

The substitution may be attained, for example, according to the methods described in Tetrahedron Letters, 34, 1007 (1993), etc.
(Step 28)

In the same manner as in the step 1, Compound (II'''') is processed to obtain compound (XXIII). Compound (XXIII) is within the scope of compound (I).

The above "alcohols" includes, for example, methanol, ethanol, isopropanol, tert-butanol, etc.

The above "ethers" includes, for example, ethyl ether, tetrahydrofuran (THF), dioxane, 1,2-dimethoxyethane, etc.

The above "halogenated hydrocarbons" includes, for example, dichloromethane, chloroform, 1,2 -dichloroethane, carbon tetrachloride, etc.

The above "aromatic solvents" includes, for example, benzene, toluene, xylene, pyridine, etc.

The above "hydrocarbons" includes, for example, hexane, pentane, cyclohexane, etc.

The above "amides" includes, for example, N,N'-dimethylformamide (DMF), N,N'-dimethylacetamide, etc.

The above "ketones" Includes, for example, acetone, methyl ethyl ketone, etc.

The above "sulfoxides" includes, for example, dimethylsulfoxide (DMSO), etc.

The above "nitriles" includes, for example, acetonitrile, etc.

The above "esters" includes, for example, ethyl acetate, etc.

In the above-mentioned reactions where the starting compounds are substituted by any of amino, carboxy, hydroxy or carbonyl, those groups may be protected by ordinary protective groups which are generally used in peptide chemistry. The protective groups may be removed after the reaction to give the intended products.

The amino-protecting group includes, for example, formyl, $C_{1-6}$ alkyl-carbonyl (e.g., acetyl, ethylcarbonyl, t-butylcarbonyl, etc.), $C_{1-6}$ alkyloxy-carbonyl (e.g., methoxycarbonyl, ethoxycarbonyl, t-butoxycarbonyl, etc.), benzoyl, $C_{7-10}$ aralkyl-carbonyl (e.g., benzylcarbonyl, etc.), $C_{7-10}$ aralkyloxy-carbonyl (e.g., benzyloxycarbonyl, 9-fluorenylmethoxycarbonyl, etc.), trityl, phthaloyl, N,N-dimethylaminomethylene, silyl (e.g., trimethylsilyl, triethylsilyl, dimethylphenylsilyl, dimethyl-t-butylsilyl, diethyl-t-butylsilyl, etc.), $C_{2-6}$ alkenyl (e.g., 1-allyl, etc.), etc. These groups may be substituted by 1 to 3 substituents of halogen atoms (e.g., fluoro, chloro, bromo, iodo, etc.), nitro, etc.

The carboxy-protecting group includes, for example, $C_{1-6}$ alkyl (e.g., methyl, ethyl, n-propyl, isopropyl, butyl, tert-butyl, etc.), phenyl, trityl, silyl (e.g., trimethylsilyl, triethylsilyl, dimethylphenylsilyl, dimethyl-t-butylsilyl, diethyl-t-butylsilyl, etc.), a $C_{2-6}$ alkenyl group (e.g., 1-allyl, etc.), etc. These groups may be substituted by 1 to 3 substituents of halogen atoms (e.g., fluoro, chloro, bromo, iodo, etc.), nitro, etc.

The hydroxy-protecting group includes, for example, phenyl, $C_{7-10}$ aralkyl (e.g., benzyl, etc.), formyl, $C_{1-6}$ alkyl-carbonyl (e.g., acetyl, propionyl, etc.), benzoyl, $C_{7-10}$ aralkyl-carbonyl (e.g., benzylcarbonyl, etc.), tetrahydropyranyl, tetrahydrofuranyl, silyl (e.g., trimethylsilyl, triethylsilyl, dimethylphenylsilyl, dimethyl-t-butylsilyl, diethyl-t-butylsilyl, etc.), $C_{2-6}$ alkenyl (e.g., 1-allyl, etc.), etc. These groups may be substituted by 1 to 3 substituents of halogen atoms (e.g., fluoro, chloro, bromo, iodo, etc.), $C_{1-6}$ alkyl (e.g., methyl, ethyl, n-propyl, etc.), nitro, etc.

The carbonyl-protecting group includes, for example, cyclic acetals (e.g., 1,3-dioxorane, etc.), acyclic acetals (e.g., di-$C_{1-6}$ alkylacetals, etc.), etc.

Those protective groups may be removed by any per se known methods, for example, the methods described in Protective Groups in Organic Synthesis, published by John Wiley and Sons, 1980, etc. For example, the method of removing these protective groups, includes the methods using acids, bases, ultraviolet rays, hydrazine, phenylhydrazine, sodium N-methyldithiocarbamate, tetrabutylammonium fluoride, palladium acetate, etc.; and reduction, etc.

Compound (I) can be isolated and purified by any known procedures, for example, through solvent extraction, ph adjustment, redistribution, crystallization, recrystallization, chromatography, etc. The starting compounds and intermediates and their salts for compound (I) can also be isolated and purified according to the same known procedures as above, but without any isolation procedure, they may be used in the next step while they are in reaction mixtures.

Compound (I) may also be in the form of hydrates or non-hydrates thereof.

Where compound (I) includes optical isomers, stereoisomers, regio isomers and rotational isomers, those are within the scope of compound (I), and can be isolated as their single compound through per se known synthesis or separation. For example, where optical isomers of compound (I) exist, those resolved from their mixtures through optical resolution are within the scope of compound (I).

The optical isomers can be produced in any per se known manner. Concretely, optically active synthetic intermediates or mixtures of racemic isomers of the final product are subjected to ordinary optical resolution to give the corresponding optical isomers.

For the optical resolution, employable are any per se known methods, such as a fractional recrystallization method, a chiral column method, a diastereomer method, etc.

1) Fractional Recrystallization

The method which comprises allowing a racemate to react with an optically active compound (e.g., (+)-mandelic acid, (−)-mandelic acid, (+)-tartaric acid, (−)-tartaric acid, etc.) to give a salt, which is then isolated through fractional recrystallization, followed by, when desired, subjecting the isolated compound to neutralization to obtain free optical isomers.

2) Chiral Column Method

The method of separating a racemate or a salt thereof, which comprises utilizing a column for fractionating optical isomers (chiral column). In the case of liquid column chromatography, for example, a mixture of optical isomers is applied to a chiral column, such as ENANTIO-OVM (manufactured by Tosoh Corp.), CHIRAL SERIES (manufactured by Daicel Co.), etc., which is then eluted with water, various buffers (e.g., phosphate buffer) and organic solvents (e.g., ethanol, methanol, acetonitrile), singly or a suitable mixture of them, to isolate the individual optical isomers. In case of gas chromatography, for example, a chiral column such as CP-Chirasil-DeX CB (manufactured by GL Science Co.), etc. is used for the fractionation.

3) Diastereomer Method

The method of obtaining the optical isomer, which comprises allowing a mixture of racemate to react with an optically active reagent to give a mixture of diastereomers, subjecting the mixture to conventional fractionation procedure (e.g., fractional recrystallization, chromatography, etc.) to give a simple substance, then cleaving off the optically active reagent moiety by a chemical treatment such us hydrolysis. For example, where compound (I) has a hydroxy group or a primary or secondary amino group in the molecule, it is subjected to condensation with an optically active organic acid (e.g., MPTA [α-methoxy-α-(trifluoromethyl)phenylacetic acid], (−)-menthoxyacetic acid, etc.) or the like to give the corresponding ester-type or amide-type diastereomers. On the other hand, where compound (I) has a carboxylic acid group, it is subjected to condensation with an optically active amine or an alcohol reagent to give the corresponding amide-type or ester-type diastereomers. The thus-isolated diastereomer can be converted to the original compound by subjecting to acidic or basic hydrolysis.

As having an excellent mitochondrial function activating effect, an excellent antioxidative effect, etc., compound (I) is effective in inhibiting various disorders to be caused by mitochondrial function insufficiency or mitochondrial electron-transport disorder, such as hypodynamia, retinal pigment degeneration, paropsis, dystonia, convulsion, dyskinesia, cerebral infarction-like episode, hypacusis, peripheral nervous system disorders, etc.

In addition, compound (I) has low toxicity.

Therefore, compound (I) is usable as medicines for preventing and/or treating various disorders to be caused by mitochondrial function insufficiency or mitochondrial electron-transport disorder in mammals including human beings, and its dose may be small.

The disorders include, for example, neurodegenerative disorders (e.g., Parkinson's disease, Alzheimer's disease, amyotrophic lateral sclerosis, Huntington's disease, etc.), other central nervous system disorders (e.g., cerebrovascular dementia, schizophrenia, depression, etc.), mitochondrial disease [e.g., CPEO (chronic progressive external ophthalmoplegia), Kearns-Sayre syndrome, MERRF (myoclonus epilepsy with ragged-red fibers), MELAS (mitochondrial myopathy, encephalopathy lactic acidosis and stroke-like episodes), Leigh disease, Alpers disease, Leber disease, Pearson disease etc.], cardiovascular system disorders (e.g., cardiomyopathy such as congestive cardiomyopathy, etc., arteriosclerosis, myocardial infarction, peripheral vascular disease, angina pectoris, congestive heart failure, hypertension, cardiogenic shock, acute or chronic renal failure, etc.), insulin-independent diabetes mellitus, paropsis, senile hypacusis, hepatic disease, cancer, and so forth. (Referred to is a reference, Proceedings of National Academy of Sciences, USA, 91, 8731–8738 (1994), etc.) As additionally having an excellent nerve growth factor secretion promoting effect, a β amyloid-caused neuronal cell death preventing effect, etc., compound (I) is also useful as medicines for preventing and/or treating central nervous system disorders (e.g., Parkinson's disease, Alzheimer's disease, cerebrovascular dementia, etc.) in mammals including human beings. Among others, preferred is a medicine for preventing and/or treating neurodegenerative disorders such as Parkinson's disease, Alzhelmer's disease, amyotrophic lateral sclerosis, Huntington's disease, etc., more preferred is medicine for preventing and/or treating Alzheimer's disease.

Compound (I) can be used together with an anti-dementia drug.

Compound (I) can be formulated into pharmaceutical compositions by any per se known means. Directly or after having been formulated into pharmaceutical compositions along with suitable amounts of any pharmaceutically acceptable carriers, compound (I) can be safely administered to mammals including human beings. For example, compound (I) can be mixed with suitable amounts of any desired, pharmaceutically acceptable carriers in any per se known formulation processes to give tablets (including sugar-coated tablets and film-coated tablets), powdery preparations, granules, capsules (including soft capsules), liquid preparations, injections, suppositories, controlled-release preparations, etc., which may be safely administered to mammals including human beings, either orally or non-orally (e.g., local, rectal or intravenous administrations, etc.).

In the pharmaceutical composition of the present invention, the amount of compound (I) is 0.1 to nearly 100% by weight of the total weight of the composition. The dose of the composition varies, depending on the subject to which the composition is administered, the administration route employed, the disorder of the subject, etc. For example, for the oral composition for treating Alzheimer's disease, its dose may be about 0.1 to 2000 mg/adult (weighing about 60 kg) or so, preferably about 15 to 300 mg/adult or so, in terms of the active ingredient of compound (I), and this may be administered once or several times a day.

Any ordinary organic and inorganic carrier substances that are generally used in formulating medicines are usable as the carriers for formulating the pharmaceutical compositions of the present invention. For example, employable are ordinary excipients, lubricants, binders, disintegrators, etc. for formulating solid preparations; and solvents, solubilizers, suspending agents, isotonizing agents, buffers, soothing agents, etc. for formulating liquid preparations. If desired, further employable are other additives such as preservatives, antioxidants, colorants, sweeteners, adsorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, etc.

The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

The preservatives include, for example, p-hydroxybenzoates, chlorobutanol, benzyl alcohol, phenethyl alcohol, dehydroacetic acid, sorbic acid, etc.

The antioxidants include, for example, sulfites, ascorbic acid, etc.

BEST MODE FOR CARRYING OUT THE INVENTION

The invention will be described in more detail hereinafter, with reference to Reference Examples, Examples, Formulation Example and Experimental Examples, which, however, are not intended to restrict the scope of the present invention. Various changes and modifications can be made within the range that does not deviate the scope of the present invention.

In the following Reference Examples and Examples, "Room temperature" is meant to indicate a temperature falling between 0° C. and 30° C., and for removing water from the organic solution used therein, employed were anhydrous magnesium sulfate or anhydrous sodium sulfate. Unless otherwise specifically indicated, "%" is by weight.

The meanings of the abbreviations used hereinafter are as follows.

s: singlet
d: doublet
t: triplet
q: quartet
m: multiplet
br: broad
J: coupling constant
Hz: Hertz
$CDCl_3$: deuterated chloroform
THF: tetrahydrofuran
DMF: N,N-dimethylformamide
DMSO: dimethylsulfoxide
CAN: cerium(IV) ammonium nitrate
NBS: N-bromosuccinimide
AIBN: 2,2'-azobis(isobutyronitrile)
LDA: lithium diisopropylamide
$^1$H-NMR: proton nuclear magnetic resonance spectrum (generally measured as the free form of each sample in $CDCl_3$)

Reference Example 1

1,2,3,4-Tetramethoxy-5-methylbenzene

A solution of sodium dithionite (95.4 g, 0.548 mols) in water (330 ml) was added to a solution of 2,3-dimethoxy-5-methyl-1,4-benzoquinone (50 g, 0.274 mols) in diethyl ether (330 ml), and shaken for 15 minutes. The ether layer was washed with a saturated aqueous sodium chloride solution, then dried and concentrated in vacuo. The resulting crystals were washed with hexane to obtain 2,3-dimethoxy-5-methyl-1,4-hydroquinone (46.1 g).

Dimethylsulfate (126 g, 1.00 mol) was added to 2,3-dimethoxy-5-1,4-hydroquinone (46.1 g, 0.250 mols), and then ethanol was added thereto. To the resulting mixture was dropwise added a methanol solution of sodium methoxide (28%, 241 g, 1.25 mols), and then concentrated in vacuo. After having added water thereto, this was extracted with ethyl acetate, and the organic layer was washed with water and a saturated aqueous sodium chloride, then dried, and concentrated in vacuo. The residue was purified by alumina column chromatography (hexane:ethyl acetate=25:1), and the entitled compound (51.6 g) was obtained as an oil.

$^1$H-NMR ($CDCl_3$) δ: 2.23 (3H,s), 3.78 (3H,s), 3.82 (3H, s), 3.87 (3H,s), 3.93 (3H,s), 6.45 (1H,s).

Reference Example 2

1-Bromo-2,3,4,5-tetramethoxy-6-methylbenzene

Bromine (46.7 g, 0.292 mols) was dropwise added to a solution of 1,2,3,4-tetramethoxy-5-methylbenzene (51.6 g, 0.243 mols) in acetic acid (100 ml) at room temperature, and the reaction mixture was stirred for 15 minutes and then concentrated in vacuo. The residue was diluted with ethyl acetate, and the organic layer was washed with water, a saturated aqueous sodium bicarbonate solution, water and a saturated aqueous sodium chloride solution, then dried, and concentrated in vacuo. The thus-obtained crude product was purified by silica gel column chromatography (hexane:ethyl acetate=20:1) to obtain the entitled compound (59.1 g) as an oil.

$^1$H-NMR ($CDCl_3$) δ: 2.30(3H,s), 3.79 (3H,s), 3.85 (3H,s), 3.91 (6H,s).

Reference Example 3

1-Bromo-6-bromomethyl-2,3,4,5-tetramethoxybenzene

An ethyl acetate (300 ml) solution of 1-bromo-2,3,4,5-tetramethoxy-6-methylbenzene (49.5 g, 0.170 mols), N-bromosuccinimide (31.8 g, 0.179 mols) and AIBN (558 mg, 3.40 mmols) was heated under reflux for 1 hour. The reaction mixture was concentrated in vacuo, and then diluted with hexane. The resulting crystals were separated by filtration, and the filtrate was concentrated to obtain the entitled compound (62.6 g) as an oil.

$^1$H-NMR (CDCl$_3$) δ: 3.86 (3H,s), 3.91 (3H,s), 3.95 (3H,s) 3.98 (3H,s), 4.71 (2H,s).

Reference Example 4

Ethyl 8-Bromooctanoate

Thionylchloride (8.15 ml, 0.112 mols) was added dropwise to an ethanol (500 ml) solution of 8-bromooctanoic acid (50.0 g, 0.224 mols) with cooling with ice, and the reaction mixture was then stirred for 12 hours at room temperature. The reaction mixture was concentrated in vacuo, and a saturated aqueous sodium bicarbonate solution was added to the residue, which was then extracted with ethyl acetate. The organic layer was washed with water and a saturated aqueous sodium chloride solution, then dried, and concentrated in vacuo. The thus-obtained crude product was purified by alumina column chromatography (hexane) to obtain the entitled compound (51.6 g) as an oil.

$^1$H-NMR (CDCl$_3$) δ: 1.18–1.96 (10H,m), 1.26 (3H,t,J= 7.1 Hz), 2.29 (2H,t,J=7.3 Hz), 3.41 (2H,t,J=6.8 Hz), 4.13 (2H,q,J=7.1 Hz).

Reference Example 5

Ethyl 2,9-diethoxycarbonylnonanate

Diethyl malonate (9.85 g, 61.5 mmols) was added to an ethanol (170 ml) solution of sodium ethoxide (4.61 g, 67.7 mmols) with cooling with ice, and then stirred for 15 minutes at room temperature, and thereafter ethyl 8-bromooctanoate (17.0 g, 67.7 mmols) was added thereto. The reaction mixture was heated under reflux for 2 hours, and then an aqueous saturated ammonium chloride solution was added thereto, and extracted with ethyl acetate. The organic layer was washed with water and a saturated aqueous sodium chloride solution, then dried, and concentrated in vacuo. The thus-obtained crude product was purified by silica gel column chromatography (hexane:ethyl acetate= 20:1) to obtain the entitled compound (13.7 g) as an oil.

$^1$H-NMR (CDCl$_3$) δ: 1.2–2.0 (21H,m), 2.28 (2H,t,J=7.4 Hz), 3.31 (1H,t,J=7.6 Hz), 4.05–4.30 (6H,m).

Reference Example 6

Ethyl 10-(6-bromo-2,3,4,5-tetramethoxyphenyl)-9,9-diethoxycarbonyldecanoate

A THF (10 ml) solution of ethyl 2,9-diethoxycarbonylnonanoate (8.86 g, 26.8 mmols) was dropwise added to a THF (90 ml) suspension of sodium hydride (60% oily, 1.29 g, 32.2 mmols) at room temperature. The reaction mixture was stirred for 2 hours, and then a THF (10 ml) solution of 1-bromo-6-bromomethyl-2,3,4,5-tetramethoxybenzene (10.9 g, 29.5 mmols) was dropwise added at room temperature, and stirring was continued for additional 2 hours. The reaction mixture was diluted with a saturated aqueous ammonium chloride solution and then concentrated in vacuo. The residue was extracted with ethyl acetate, and the resulting organic layer was washed with water and a saturated aqueous sodium chloride solution, then dried, and concentrated in vacuo. The crude product thus obtained was purified by silica gel column chromatography (hexane:ethyl acetate=10:1 to 4:1) to obtain the entitled compound (10.9 g) as an oil.

$^1$H-NMR (CDCl$_3$) δ: 1.1–1.8 (21H,m), 2.27 (2H,t,J=7.5 Hz), 3.51 (2H,s), 3.71 (3H,s), 3.82 (3H,s), 3.88 (3H,s), 3.93 (3H,s), 4.04–4.30 (6H,m).

Reference Example 7

Ethyl 8-(2-ethoxycarbonyl-4,5,6,7-tetramethoxyindan-2-yl) octanoate

A hexane solution of n-butyl lithium (1.68 M, 13.1 ml, 22.0 mmols) was dropwise added to a THF (80 ml) solution of ethyl 10-(6-bromo-2,3,4,5-tetramethoxyphenyl)-9,9-diethoxycarbonyldecanoate (7.54 g, 12.2 mmols) under a nitrogen stream at −70° C. or lower The reaction mixture was stirred for 15 minutes, and then a THF (10 ml) solution of acetic acid (1.71 g, 28.5 mmols) was dropwise added thereto at −70° C. or lower. After having been allowed to warm to room temperature, the reaction mixture was concentrated in vacuo. A saturated aqueous sodium bicarbonate solution was added to the resulting residue, which was then extracted with ethyl acetate. The organic layer was washed with water and a saturated aqueous sodium chloride solution, then dried, and distilled in vacuo. The resulting crude product was dissolved in ethanol (80 ml), to which was added sodium borohydride (923 mg, 24.4 mmols) with cooling with ice. The reaction mixture was allowed to warm to room temperature, and then stirred for 6 hours. Water was added thereto, and extracted with ethyl acetate. The organic layer was washed with a saturated aqueous sodium chloride solution, and then dried. The solvent was evaporated out in vacuo, and the resulting crude product was isolated through silica gel column chromatography (hexane:ethyl acetate= 10:1 to 5:1) to obtain ethyl 8-(2-ethoxycarbonyl-1-hydroxy-4,5,6,7-tetramethoxyindan-2-yl)octanoate (3.77 g).

To ethyl 8-(2-ethoxycarbonyl-1-hydroxy-4,5,6,7-tetramethoxyindan-2-yl)octanoate (3.77 g, 7.59 mmols), added was trifluoroacetic acid (40 ml) at room temperature, and then triethylsilane (4.85 ml, 30.4 mmols) was added thereto, and stirred for 15 minutes. The reaction mixture was concentrated in vacuo, a saturated aqueous sodium bicarbonate solution was added thereto, and extracted with ethyl acetate, and the resulting organic layer was washed with water and a saturated aqueous sodium chloride solution, and then dried. The solvent was evaporated out in vacuo, and the resulting crude product was purified by silica gel column chromatography (hexane:ethyl acetate=20:1 to 10:1) to obtain the entitled compound (1.31 g) as an oil.

$^1$H-NMR (CDCl$_3$) δ: 1.10–1.80 (18H,m), 2.27 (2H,t,J= 7.5 Hz), 2.85 (2H,d,J=16.2 Hz), 3,41 (2H,d,J=16.2 Hz), 3.83 (6H,s), 3.89 (6H,s), 4.12 (2H,q,J=7.3 Hz), 4.16 (2H,q,J=7.3 Hz).

Reference Example 8

8-(2-Carboxy-4,5,6,7-tetramethoxyindan-2-yl)octanoic acid

A mixture comprised of an ethanol (4 ml) solution of ethyl 8-(2-ethoxycarbonyl-4,5,6,7-tetramethoxyindan-2-yl) octanoate (200 mg, 0.416 mmols) and an aqueous sodium hydroxide solution (3 M, 0.553 ml, 1.66 mmols) was heated under reflux for 12 hours. The reaction mixture was concentrated in vacuo, which was made acidic with 1 N hydrochloric acid, followed by extraction with ethyl acetate. The organic layer was washed with a saturated aqueous sodium chloride solution, and then dried. The solvent was evaporated out in vacuo, and the resulting crude product was purified by silica gel column chromatography (hexane:ethyl acetate=1:2 to ethyl acetate only) to obtain the entitled compound (88.6 mg) as an oil.

$^1$H-NMR (CDCl$_3$) δ: 1.18–1.84 (12H,m), 2.34 (2H,t,J= 7.0 Hz), 2.86 (2H,d,J=16.3 Hz), 3.45 (2H,d,J=16.3 Hz), 3.82 (6H,s), 3.88 (6H,s).

Reference Example 9

8-(2-Ethoxycarbonyl-4,5,6,7-tetramethoxyindan-2-yl) octanoic acid

A mixture comprised of an ethanol (8 ml) solution of ethyl 8-(2-ethoxycarbonyl-4,5,6,7-tetramethoxyindan-2-yl)

octanoate (367 mg, 0.764 mmols) and an aqueous sodium hydroxide solution (1N, 0.764 ml, 0.764 mmols) was stirred at room temperature for 6 hours, and an aqueous sodium hydroxide solution (1 N, 0.153 ml, 0.153 mmols) was added thereto and the stirring was continued at room temperature for further 6 hours. The reaction mixture was concentrated in vacuo, which was made acidic by adding 1 N hydrochloric acid, followed by extraction with ethyl acetate. The organic layer was washed with water and a saturated aqueous sodium chloride solution, and then dried. The solvent was evaporated out in vacuo, and the resulting crude product was purified by silica gel column chromatography (hexane:ethyl acetate=2:1 to 1:2) to obtain the entitled compound (78.6 mg) as an oil.

$^1$H-NMR (CDCl$_3$) δ: 1.16–1.80 (12H,m), 1.26 (3H,t,J=7.0 Hz), 2.33 (2H,t,J=7.5 Hz), 2.85 (2H,d,J=16.1 Hz), 3.41 (2H,d,J=16.1 Hz), 3.83 (6H,s), 3.89 (6H,s), 4.16 (2H,q,J=7.0 Hz).

Reference Example 10
N-[8-(2-Ethoxycarbonyl-4,5,6,7-tetramethoxyindan-2-yl) octanoyl]morpholine A THF (4.0 ml) suspension of 8-(2-ethoxycarbonyl-4,5,6,7-tetramethoxyindan-2-yl)octanoic acid (114 mg, 0.252 mmols), morpholine (0.110 ml, 1.26 mmols), 1-ethyl-3-(3-dimethylaminopropyl)carbodiimide hydrochloride (96.6 mg, 0.504 mmols) and 1-hydroxybenzotriazole monohydrate (77.2 mg, 0.504 mmols) was stirred at room temperature for 12 hours. The reaction mixture was concentrated in vacuo, to which was added water. Then, this was extracted with ethyl acetate, and the organic layer was washed with water and a saturated aqueous sodium chloride solution, and then dried. The solvent was evaporated out, and the resulting crude product was purified by silica gel column chromatography (hexane:ethyl acetate=4:1 to 1:1) to obtain the entitled compound (123 mg) as an oil.

$^1$H-NMR (CDCl$_3$) δ: 1.16–1.80 (12H,m), 1.26 (3H,t,J=7.0 Hz), 2.29 (2H,t,J=7.5 Hz), 2.84 (2H,d,J=16.2 Hz), 3.41 (2H,d,J=16.2 Hz), 3.40–3.52 (2H,m), 3.54–3,74 (6H,m), 3.83 (6H,s), 3.89 (6H,s), 4.16 (2H,q,J=7.0 Hz).

Reference Example 11
8-(2-Carbamoyl-4,5,6,7-tetramethoxyindan-2-yl) octanamide Oxalyl chloride (0.086 ml, 0.988 mmols) was added to a THF (5.0 ml) solution of 8-(2-carboxy-4,5,6,7-tetramethoxyindan-2-yl)octanoic acid (105 mg,0.247 mmols) and a catalytic amount of DMF, at room temperature. The reaction mixture was stirred for 30 minutes, and then concentrated in vacuo. The residue was dissolved in THF (5.0 ml). The resulting THF solution was dropped into aqueous 28% ammonia (5.0 ml) with cooling with ice. The reaction mixture was stirred for 5 minutes, to which was added water followed by extraction with ethyl acetate. The organic layer was washed with a saturated aqueous sodium chloride solution, then dried, and concentrated in vacuo to obtain the entitled compound (103 mg) as an amorphous powder.

$^1$H-NMR (CDCl$_3$) δ: 1.18–1.76 (12H,m), 2.21 (2H,t,J=7.5 Hz), 2.89 (2H,d,J=15.8 Hz), 3.34 (2H,d,J=15.8 Hz), 3.83 (6H,s), 3.89 (6H,s), 5.3–5.7 (4H,m).

Reference Example 12
Ethyl 2-(8-hydroxyoctyl)-4,5,6,7-tetramethoxy-2-indancarboxylate A THF solution of borane complex (1 M, 3.74 ml, 3.74 mmols) was added to a THF (9.0 ml) solution of 8-(2-ethoxycarbonyl-4,5,6,7-tetramethoxyindan-2-yl)octanoic acid (847 mg, 1.87 mmol), with cooling with ice. The reaction mixture was allowed to warm to room temperature, and then stirred for 2 hours. 1N hydrochloric acid was added and the reaction mixture was then extracted with ethyl acetate. The organic layer was washed with water and a saturated aqueous sodium chloride solution, and then dried. The solvent was evaporated out in vacuo, and the resulting crude product was purified by silica gel column chromatography (hexane:ethyl acetate=4:1) to obtain the entitled compound (713 mg) as an oil.

$^1$H-NMR (CDCl$_3$) δ: 1.16–1.80 (14H,m), 1.26 (3H,t,J=7.0 Hz), 2.85 (2H,d,J=16.1 Hz), 3.41 (2H,d,J=16.1 Hz), 3.63 (2H,t,J=6.6 Hz), 3.83 (6H,s), 3.89 (6H,s), 4.16 (2H,q,J=7.0 Hz).

Reference Example 13
8-(2-Hydroxymethyl-4,5,6,7-tetramethoxyindan-2-yl) octanol Lithium aluminium hydride (72.1 mg, 1.90 mmols) was added to a diethyl ether (6.0 ml) solution of ethyl 8-(2-ethoxycarbonyl-4,5,6,7-tetramethoxyindan-2-yl)octanoate (315 mg, 0.634 mmols), with cooling with ice. The reaction mixture was warmed to room temperature, and then stirred for 1 hour. 1N hydrochloric acid was added to the reaction mixture with cooling with ice, which was then extracted with ethyl acetate. The organic layer was washed with a saturated aqueous sodium chloride solution, and then dried. The solvent was evaporated out, and the resulting crude product was purified by silica gel column chromatography (hexane:ethyl acetate=4:1 to 1:1) to obtain the entitled compound (239 mg) as an oil.

$^1$H-NMR (CDCl$_3$) δ: 1.18–1.70 (14H,m), 2.67 (2H,d,J=16.1 Hz), 2.83 (2H,d,J=16.1 Hz), 3.51 (2H,br,s), 3.64 (2H, t,J=6.6 Hz), 3.82 (6H,s), 3.89 (6H,s).

Reference Example 14
2-(8-Hydroxyoctyl)-4,5,6,7-tetramethoxy-2-indancarboxylic acid An aqueous sodium hydroxide solution (3N, 1.07 ml, 3.22 mmols) was added to an ethanol (10 ml) solution of ethyl 2-(8-hydroxyoctyl)-4,5,6,7-tetramethoxy-2-indancarboxylate (708 mg, 1.61 mmols). The reaction mixture was heated under reflux for 6 hours, and then concentrated in vacuo, which was made acidic with 1 N hydrochloric acid and then extracted with ethyl acetate. The organic layer was washed with a saturated aqueous sodium chloride solution, and then dried. The solvent was evaporated out in vacuo, and the resulting crude product was purified by silica gel column chromatography (hexane:ethyl acetate=2:1 to 1:2) to obtain the entitled compound (335 mg) as an oil.

$^1$H-NMR (CDCl$_3$) δ: 1.12–1.84 (14H,m), 2.87 (2H,d,J=16.5 Hz), 3.46 (2H,d,J=16.5 Hz), 3.64 (2H,t,J=6.6 Hz), 3.83 (6H,s), 3.89 (6H,s).

Reference Example 15
N-Methyl-2-(8-hydroxyoctyl)-4,5,6,7-tetramethoxy-2-indancarboxamide A THF (3.0 ml) solution of 2-(8-hydroxyoctyl)-4,5,6,7-tetramethoxy-2-indan-carboxylic acid (300 mg, 0.731 mmols) was added to a THF (3.0 ml) suspension of methyl ammonium chloride (247 mg, 3.66 nmnols), 1-ethyl-3-(3-dimethylaminopropyl)carbodiimide hydrochloride (420 mg, 2.19 mmols), 1-hydroxybenzotriazole monohydrate (335 mg, 2.19 mmols) and triethylamine (1.02 ml, 7.31 mmols), at room temperature. The reaction mixture was stirred for 12 hours, and then concentrated in vacuo. Water was added to the resulting residue, which was then extracted with ethyl acetate. The organic layer was washed with a saturated aqueous sodium chloride solution, and then dried. The solvent was evaporated out in vacuo, and the resulting crude product was purified by alumina column chromatography (ethyl acetate) to obtain the entitled compound (277 mg) as an oil.

$^1$H-NMR (CDCl$_3$) δ: 1.16–1.76 (14H,m), 2.83 (3H,d,J=4.8 Hz), 2.88 (2H,d,J=15.8 Hz), 3.30 (2H,d,J=15.8 Hz), 3.62 (2H,t,J=6.6 Hz), 3.82 (6H,s), 3.89 (6H,s), 5.50–5.66 (1H,m).

Reference Example 16

Ethyl 8-(4,5,6,7-tetramethoxyinden-2-yl)octanoate

A hexane solution of n-butyl lithium (1.68 M, 6.13 ml, 10.3 mmols) was dropwise added to a THF (40 ml) solution of ethyl 10-(6-bromo-2,3,4,5-tetramethoxyphenyl)-9,9-diethoxycarbonyldecanoate (3.53 g, 5.70 mmols), under nitrogen stream at −70° C. or lower. The reaction mixture was stirred for 15 minutes, and a THF (10 ml) solution of acetic acid (1.71 g, 28.5 mmols) was dropwise added thereto at −70° C. or lower, and then warmed to room temperature. The reaction mixture was concentrated in vacuo, and a saturated aqueous sodium bicarbonate solution was added thereto, and then extracted with ethyl acetate. The organic layer was washed with water and a saturated aqueous sodium chloride solution, and then dried. The solvent was evaporated out in vacuo, and the resulting crude product was dissolved in a mixture comprised of acetic acid (30 ml) and 10% HCl 10 ml, and stirred at 80° C. for 36 hours. The reaction mixture was concentrated in vacuo, followed by addition of water, and then extraction with ethyl acetate. The organic layer was washed with water and a saturated aqueous sodium chloride solution, and then dried. The solvent was evaporated out in vacuo, and the resulting crude product was purified by silica gel column chromatography (hexane:ethyl acetate=2:1) to obtain a crude product (1.30 g) of 8-(4,5,6,7-tetramethoxyindan-1-oxo-2-yl)octanoic acid.

Thionylchloride (0.723 ml, 9.90 mmols) was added to an ethanol (30 ml) solution of the crude product of 8-(4,5,6,7-tetramethoxyindan-1-oxo-2-yl)octanoic acid (1.30 g, ca. 3.30 mmols), which was allowed to warm to room temperature, and stirred for 30 minutes. The reaction mixture was concentrated in vacuo, and then diluted with ethyl acetate. The organic layer was washed with a saturated aqueous sodium bicarbonate solution, water and a saturated aqueous sodium chloride solution, and then dried. The solvent was evaporated out in vacuo to obtain a crude product (1.31 g) of ethyl 8-(4,5,6,7-tetramethoxyindan-1-oxo-2-yl)octanoate.

Sodium borohydride (235 mg, 6.20 mmols) was added to an ethanol (13 ml) solution of the crude product of ethyl 8-(4,5,6,7-tetramethoxyindan-1-oxo-2-yl)octanoate (1.31 g, ca. 3.10 mmols), then the solution was allowed to warm to room temperature, and stirred for 6 hours. The reaction mixture was concentrated in vacuo, to which was added water. Then, the reaction mixture was neutralized with 10% hydrochloric acid, and then extracted with ethyl acetate. The organic layer was washed with water and a saturated aqueous sodium chloride solution, and then dried. The solvent was evaporated out in vacuo, and the resulting residue was purified by silica gel column chromatography (hexane:ethyl acetate=10:1 to 2:1) to obtain a crude product of ethyl 8-(1-hydroxy-4,5,6,7-tetramethylindan-2-yl)octanoate (575 mg).

Trifluoroacetic acid (6.0 ml) was added to the crude product of 8-(1-hydroxy-4,5,6,7-tetramethylindan-2-yl) octanoate (575 mg, ca. 1.35 mmols), and triethylsilane (0.862 ml, 5.40 mmols) was added thereto, and the stirring was continued for 30 minutes. The reaction mixture was concentrated in vacuo followed by addition of a saturated aqueous sodium bicarbonate solution, which was then extracted with ethyl acetate. The organic layer was washed with water and a saturated aqueous sodium chloride solution, and then dried. The solvent was evaporated out, and the resulting crude product was purified by silica gel column chromatography (hexane:ethyl acetate=10:1 to 8:1) to obtain the entitled compound (410 mg) as an oil.

$^1$H-NMR (CDCl$_3$) δ: 1.10–1.76 (10H, m), 1.26 (3H,t,J=7.0 Hz), 2.30 (2H,t,J=7.6 Hz), 2.44 (2H,t,J=7.5 Hz), 3.31 (2H,s), 3.90 (6H,s), 3.96 (6H,s), 4.13 (2H,q,J=7.0 Hz), 6.55 (1H,s).

Reference Example 17

Ethyl 8-(4,5,6,7-tetramethoxyindan-2-yl)octanoate

An ethanol (6.0 ml) suspension of ethyl 8-(4,5,6,7-tetramethoxyinden-2-yl)octanoate (310 mg, 0.763 mmols) and 10% palladium-carbon (60 mg) was stirred under a hydrogen atmosphere at room temperature for 4 hours. The palladium-carbon was removed by filtration, and the filtrate was concentrated in vacuo to obtain the entitled compound (310 mg) as an oil.

$^1$H-NMR (CDCl$_3$) δ: 1.20–1.74 (12H,m), 1.26 (3H,t,J=7.0 Hz), 2.30 (2H,t,J=7.5 Hz), 2.30–2.56 (3H,m), 2.98–3.14 (2H,m), 3.83 (6H,s), 3.89 (6H,s), 4.13 (2H,q,J=7.0 Hz).

Reference Example 18

8-(4,5,6,7-Tetramethoxyindan-2-yl)octanol

Lithium aluminium hydride (41.8 mg, 1.10 mmols) was added to a diethyl ether (3.0 ml) solution of ethyl 8-(4,5,6,7-tetramethoxyindan-2-yl)octanoate (150 mg, 367 mmols), with cooling with ice. The reaction mixture was allowed to warm to room temperature and stirred for 1 hour. 1 N hydrochloric acid was added to the reaction mixture, which was then extracted with ethyl acetate. The organic layer was washed with water and a saturated aqueous sodium chloride solution, and then dried. The solvent was evaporated out in vacuo, and the resulting crude product was purified by silica gel column chromatography (hexane:ethyl acetate=10:1 to 4:1) to obtain the entitled compound (138 mg) as an oil.

$^1$H-NMR (CDCl$_3$) δ: 1.20–1.70 (14H,m), 2.32–2.58 (3H, m), 2.96–3.16 (2H,m), 3.65 (2H,t,J=6.6 Hz), 3.83 (6H,s), 3.89 (6H,s).

Reference Example 19

Ethyl 4-benzyloxyphenylacetate

A DMF (100 ml) suspension of 4-hydroxyphenylacetic acid (10.0 g, 55.5 mmols), benzyl bromide (7.93 ml, 66.6 mmols) and potassium carbonate (23.1 g, 167 mmols) was stirred at room temperature for 6 hours. Water was added to the reaction mixture, which was then extracted with ethyl acetate. The organic layer was washed with water and a saturated aqueous sodium chloride solution, and then dried. The solvent was evaporated out in vacuo, and the resulting crude product was purified by silica gel column chromatography (hexane alone to hexane:ethyl acetate=10:1) to obtain the entitled compound (14.6 g) as an oil.

$^1$H-NMR (CDCl$_3$) δ: 1.25 (3H,t,J=7.2 Hz), 3.55 (2H,s), 4.14 (2H,q,J=7.2 Hz), 5.05 (2H,s), 6.93 (2H,d,J=8.6 Hz), 7.20 (2H,d,J=8.6 Hz), 7.26–7.50 (5H,m).

Reference Example 20

Ethyl 2-(4-benzyloxyphenyl)-2-ethoxycarbonylacetate

A heptane solution of LDA (2.0 M, 36.4 ml, 72.8 mmols) was dropwise added to a THF (130 ml) solution of ethyl 4-benzyloxyphenylacetate (13.1 g, 48.5 mmols) and ethyl chlorocarbonate (9.25 ml, 97.0 mmols), under a nitrogen stream at −70° C. or lower. The reaction mixture was stirred for 15 minutes, then a saturated aqueous ammonium chloride solution was added thereto, and the resulting mixture was allowed to warm to room temperature, and then extracted with diethyl ether. The organic layer was washed with a saturated aqueous sodium chloride solution, and then dried. The solvent was evaporated out in vacuo, and the resulting residue was washed with hexane to obtain the entitled compound (13.8 g) as crystals, which were further recrystallized from hexane.

m.p.: 65–66° C.

Reference Example 21

Ethyl 2-(4-benzyloxyphenyl)-3-(6-bromo-2,3,4,5-tetramethoxyphenyl)-2-ethoxycarbonylpropionate A DMF (120 ml) suspension of ethyl 2-(4-benzyloxyphenyl)-2-ethoxycarbonylacetate (12.0 g, 35.1 mmols), 1-bromo-6-bromomethyl-2,3,4,5-tetramethoxybenzene (16.9 g, 45.6 mmols) and potassium carbonate (14.5 g, 105 mmols) was stirred at room temperature for 6 hours, and then 1-bromo-6-bromomethyl-2,3,4,5-tetramethoxybenzene (2.60 g, 7.02 mmols) was added thereto stirring was continued at room temperature for further 6 hours. Water was added to the reaction mixture, which was then extracted with diethyl ether. The organic layer was washed with water and a saturated aqueous sodium chloride solution, and then dried. The solvent was evaporated out in vacuo, and the resulting crude product was purified by recrystallization (from hexane-ethyl acetate) to obtain the entitled compound (11.0 g) as crystals.

m.p.: 93–94° C.

Reference Example 22

Ethyl 2-(4-benzyloxyphenyl)-4,5,6,7-tetramethoxy-1-oxo-2-indancarboxylate

A hexane solution of n-butyl lithium (1.68 M, 11.3 ml, 19.0 mmols) was dropwise added to a THF (100 ml) solution of ethyl 2-(4-benzyloxyphenyl)-3-(6-bromo-2,3,4,5-tetramethoxyphenyl)-2-ethoxycarbonylpropionate (10.0 g, 15.8 mmols), under a nitrogen stream at −90° C or lower. The reaction mixture was stirred for 30 minutes, and a THF (10 ml) solution of acetic acid (1.86 g, 31.6 mmols) was dropwise added thereto still at −90° C. or lower. The reaction mixture was allowed to warm to room temperature, and diluted with diethyl ether. The organic layer was washed with a saturated aqueous sodium bicarbonate solution, water and a saturated aqueous sodium chloride solution, and then dried. The solvent was evaporated out in vacuo, and the resulting crude product was purified by silica gel column chromatography (hexane:ethyl acetate=10:1 to 5:1) to obtain the entitled compound (3.78 g) as an oil.

$^1$H-NMR (CDCl$_3$) δ: 1.21 (3H,t,J=7.1 Hz), 3,44 (1H,d,J=17.4 Hz), 3.89 (3H,s), 3.90 (3H,s), 4.00 (3H,s), 4.03 (3H,s), 3.85–4.28 (1H,m), 4.20 (2H,q,J=7.1 Hz), 5.04 (2H,s), 6.94 (2H,d,J=9.0 Hz), 7.26–7.50 (7H,m).

Reference Example 23

Ethyl 2-(4-benzyloxyphenyl)-4,5,6,7-tetramethoxy-2-indancarboxylate

Ethyl 2-(4-benzyloxyphenyl)-4,5,6,7-tetramethoxy-1-oxo-2-indancarboxylate (3.78 g, 7.46 mmols) was dissolved in ethanol (40 mmols), and sodium borohydride (564 mg, 14.9 mmols) was added thereto with cooling with ice. The reaction mixture was warmed to room temperature, and then stirred for further 6 hours. Water was added to the reaction mixture, which was neutralized with 10% hydrochloric acid, and then extracted with ethyl acetate. The organic layer was washed with water and a saturated aqueous sodium chloride solution, and then dried. The solvent was evaporated out in vacuo, and the resulting crude product was purified by silica gel column chromatography (hexane:ethyl acetate=4:1 to 2:1) to obtain ethyl 2-(4-benzyloxyphenyl)-1-hydroxy-4,5,6,7-tetramethoxy-2-indancarboxylate (3.02 g).

Trifluoroacetic acid (30 ml) was added to ethyl 2-(4-benzyloxyphenyl)-1-hydroxy-4,5,6,7-tetramethoxy-2-indancarboxylate (3.02 g, 5.94 mmols) with cooling with ice, and then triethylsilane (3.80 ml, 23.8 mmols) was added thereto at room temperature. The reaction mixture was stirred for 30 minutes, and then concentrated in vacuo. The residue was diluted with ethyl acetate, and the organic layer was washed with a saturated aqueous sodium bicarbonate solution, water and a saturated aqueous sodium chloride solution, and then dried. The solvent was evaporated out, and the resulting crude product was purified by silica gel column chromatography (hexane:ethyl acetate=10:1 to 8:1) to obtain the entitled compound (1.73 g) as an oil.

$^1$H-NMR (CDCl$_3$) δ: 1.12 (3H,t,J=7.2 Hz), 3.19 (2H,d,J=15.6 Hz), 3.86 (6H,s), 3.90 (6H,s), 3.98 (2H,d,J=15.6 Hz), 4.05 (2H,q,J=7.2 Hz), 5.05 (2H,s), 6.94 (2H,d,J=8.8 Hz), 7.26–7.48 (7H,s).

Reference Example 24

2-(4-Benzyloxyphenyl)-4,5,6,7-tetramethoxy-2-indancarboxylic acid

An aqueous sodium hydroxide solution (3 N, 0.204 ml, 0.612 mmols) was added to an ethanol (4 ml) solution of ethyl 2-(4-benzyloxyphenyl)-4,5,6,7-tetramethoxy-2-indancarboxylate (150 mg, 0.305 mmols), and heated under reflux for 6 hours. The reaction mixture was concentrated in vacuo, and was made acidic by adding 1 N hydrochloric acid and then extracted with ethyl acetate. The organic layer was washed with a saturated aqueous sodium chloride solution, and then dried. The solvent was evaporated out in vacuo, and the resulting crude product was purified by recrystallization (from hexane-ethyl acetate) to obtain the entitled compound (108 mg) as crystals.

m.p.: 171–172° C.

Reference Example 25

Ethyl 2-(4-hydroxyphenyl)-4,5,6,7-tetramethoxy-2-indancarboxylate

An ethanol (5.0 ml) suspension of ethyl 2-(4-benzyloxyphenyl)-4,5,6,7-tetramethoxy-2-indancarboxylate (105 mg, 0.213 mmols) and 10% palladium-carbon (32 mg) was stirred under a hydrogen pressure of one atmosphere at room temperature for 4 hours. The palladium-carbon was removed by filtration, and the filtrate was concentrated in vacuo to obtain the entitled compound (81.5 mg) as an oil.

$^1$H-NMR (CDCl$_3$) δ: 1.12 (3H,t,J=7.2 Hz), 3.19 (2H,d,J=15.6 Hz), 3.86 (6H,s), 3.90 (6H,s), 3.97 (2H,d,J=15.6 Hz), 4.05 (2H,q,J=7.2 Hz), 4.97 (1H,br,s), 6.79 (2H,d,J=8.7 Hz), 7.28 (2H,d,J=8.7 Hz).

Reference Example 26

Ethyl 2-[4-(4-ethoxycarbonyl-1-oxabutyl)phenyl]-4,5,6,7-tetramethoxy-2-indancarboxylate Sodium hydride (60% oily, 9.8 mg, 0.244 mmols) was added to a DMF (2 ml) solution of ethyl 2-(4-hydroxyphenyl)-4,5,6,7-tetramethoxy-2-indancarboxylate (81.5 mg, 0.203 mmols), with cooling with ice. The reaction mixture was stirred at room temperature for 30 minutes, and ethyl 4-bromobutyrate (0.0600 ml, 0.406 mmols) was dropwise added thereto at room temperature, and stirring was continued for 3 hours. Water was added to the reaction mixture, which was then extracted with diethyl ether. The organic layer was washed with water and a saturated aqueous sodium chloride solution, and then dried. The solvent was evaporated out, and the resulting crude product was purified by silica gel column chromatography (hexane:ethyl acetate=10:1 to 5:1) to obtain the entitled compound (85.1 mg) as an oil.

$^1$H-NMR (CDCl$_3$) δ: 1.12 (3H,t,J=7.0 Hz), 1.25 (3H,t,J=7.1 Hz), 2.00–2.20 (2H,m), 2.51 (2H,t,J=7.1 Hz), 3.18 (2H,d,J=15.8 Hz), 3.80–4.22 (8H,m), 3.86 (6H,s), 3.89 (6H,s), 6.84 (2H,d,J=8.8 Hz), 7.32 (2H,d,J=8.8 Hz).

Reference Example 27

2-[4-(4-Carboxy-1-oxabutyl)phenyl]-4,5,6,7-tetramethoxy-2-indancarboxylic acid

An aqueous sodium hydroxide solution (3 N, 0.440 ml, 1.32 mmols) was added to an ethanol (4 ml) solution of ethyl 2-[4-(4-ethoxycarbonyl-1-oxabutyl)phenyl]-4,5,6,7-tetramethoxy-2-indancarboxylate (342 mg, 0.662 mmols), and heated under reflux for 6 hours. The reaction mixture was concentrated in vacuo, diluted with water, made acidic by adding 10% hydrochloric acid, and then extracted with ethyl acetate. The organic layer was washed with a saturated aqueous sodium chloride solution, and then dried. The solvent was evaporated out, and the resulting crude product was purified by recrystallization (from hexane-ethyl acetate) to obtain the entitled compound (300 mg) as crystals.

m.p.: 148–150° C.

Reference Example 28

Ethyl 2-(6-bromo-2,3,4,5-tetramethoxybenzyl)-2-ethoxycarbonyl-6-(4-methoxycarbonylphenoxy)hexanoate Sodium hydride (60% oily, 1.02 g, 25.6 mmols) was added to a DMF (80 ml) solution of ethyl 2-ethoxycarbonyl-6-(4-methoxycarbonylphenoxy)hexanoate (8.55 g, 23.3 mmols), with cooling with ice, then allowed to warm to room temperature, and stirred for 30 minutes. Next, a DMF (10 ml) solution of 1-bromo-6-bromomethyl-2,3,4,5-tetramethoxybenzene (9.47 g, 25.6 mmols) was dropwise added thereto at room temperature, and stirred for 6 hours. Water was added to the reaction mixture, which was then extracted with diethyl ether. The organic layer was washed with water and a saturated aqueous sodium chloride solution, and then dried. The solvent was evaporated out in vacuo, and the resulting crude product was purified by silica gel column chromatography (hexane:ethyl acetate=20:1 to 5:1) to obtain the entitled compound (15.0 g) as an oil.

$^1$H-NMR (CDCl$_3$) δ: 1.24 (6H,t,J=7.1 Hz), 1.35–1.90 (6H,m), 3.53 (2H,s),3.73 (3H,s), 3.82 (3H,s), 3.88 (3H,s), 3.89 (3H,s), 3.93 (3H,s), 3.97 (2H,t,J=6.4 Hz), 4.02–4.32 (4H,m), 6.87 (2H,d,J=9.0 Hz), 7.97 (2H,d,J=9.0 Hz).

Reference Example 29

Ethyl 4,5,6,7-tetramethoxy-2-[4-(4-methoxycarbonylphenoxy)butyl]-1-oxo-2-indancarboxylate A hexane solution of n-butyl lithium (1.68 M, 3.27 ml, 5.50 mmols) was dropwise added to a THF (30 ml) solution of ethyl 2-(6-bromo-2,3,4,5-tetramethoxybenzyl)-2-ethoxycarbonyl-6-(4-methoxycarbonylphenoxy)hexanoate (3.00 g, 4.58 mmols), under a nitrogen stream at −90° C. or lower, and stirring was continued for 15 minutes. Then, the temperature was raised to −78° C., and stirring was further continued for 15 minutes. To the reaction mixtures was added a THF (5 ml) solution of acetic acid (1.38 g, 22.9 mmols) at −70° C. or lower, which was then allowed to warm to room temperature, and a saturated aqueous sodium bicarbonate solution was added thereto, which was then extracted with diethyl ether. The organic layer waswashed with water and a saturated aqueous sodium chloride solution, and then dried. The solvent was evaporated out, and the resulting crude product was purified by recrystallization (from hexane-ethyl acetate) to obtain the entitled compound (1.22 g) as crystals.

m.p.: 116–118° C.

Reference Example 30

Methyl 4-[4-(4,5,6,7-tetramethoxyindan-1-oxo-2-yl)butoxy]benzoate

Ethyl 4,5,6,7-tetramethoxy-2-[4-(4-methoxycarbonylphenoxy)butyl]-1-oxo-2-indancarboxylate (3.00 g, 5.65 mmols) was dissolved in a mixture of acetic acid (30 ml) and concentrated hydrochloric acid (10 ml), and stirred at 80° C. for 12 hours. The reaction mixture was diluted with ethyl acetate, and the organic layer was washed with water and a saturated aqueous sodium chloride solution, and then dried. The solvent was evaporated out in vacuo, and the resulting residue was isolated by silica gel column chromatography (hexane:ethyl acetate=1:1 to ethyl acetate only) to obtain a crude product of 4-[4-(4,5,6,7-tetramethoxyindan-1-oxo-2-yl)butoxy]benzoic acid (1.65 g).

An DMF (15 ml) solution of the crude product of 4-[4-(4,5,6,7-tetramethoxyindan-1-oxo-2-yl)butoxy]benzoic acid (1.65 g, ca. 3.71 mmols), potassium carbonate (1.14 g, 11.1 mmols) and methyl iodide (0.693 ml, 11.1 mmols) was stirred at room temperature for 12 hours. The reaction mixture was diluted with diethyl ether, and the organic layer was washed with water and a saturated aqueous sodium chloride solution, and then dried. The solvent was evaporated out in vacuo, and the resulting crude product was purified with recrystallization (from hexane-ethyl acetate) to obtain the entitled compound (1.60 g) as crystals.

m.p.: 75–77° C.

Reference Example 31

Methyl 4-[4-(4,5,6,7-tetramethoxyindan-2-yl)butoxy]benzoate

Sodium borohydride (254 mg, 6.72 mmols) was added to a methanol (15 ml) solution of methyl 4-[4-(4,5,6,7-tetramethoxyindan-1-on-2-yl)butoxy]benzoate (1.54 g, 3.36 mmols), with cooling with ice, and then the mixture allowed to warm to room temperature, and stirring was continued for 6 hours. Water was added to the reaction mixture, which was then neutralized with hydrochloric acid added thereto, and thereafter extracted with ethyl acetate. The organic layer was washed with water and a saturated aqueous sodium chloride solution, and then dried. The solvent was evaporated out in vacuo to obtain methyl 4-[4-(1-hydroxy-4,5,6,7-tetramethoxyindan-2-yl)butoxy]benzoate (1.50 g).

A methanol (30 ml) suspension of methyl 4-[4-(1-hydroxy-4,5,6,7-tetramethoxyindan-2-yl)butoxy]benzoate (1.50 g, 3.26 mmols), concentrated hydrochloric acid (0.0652 ml, 0.652 mmols) and 10% palladium-carbon (300 mg) was stirred under a hydrogen stream at room temperature for 4 hours. The palladium-carbon was removed by filtration, and the filtrate was concentrated in vacuo. The resulting crude product was purified by recrystallization (from hexane) to obtain the entitled compound (1.25 g) as crystals.

m.p.: 68–71° C.

Reference Example 32

4-[4-(4,5,6,7-Tetramethoxyindan-2-yl)butoxy]phenylmethanol

Lithium aluminium hydride (68.3 mg, 1.80 mmols) was added to a diethyl ether (10 ml) solution of methyl 4-[4-(4,5,6,7-tetramethoxyindan-2-yl)butoxy]benzoate (400 mg, 0.900 mmols), with cooling with ice, then the mixture was warmed to room temperature, and stirred for 1 hour. 1N hydrochloric acid was added to the reaction mixture with cooling with ice, which was then extracted with ethyl acetate. The organic layer was washed with water and a saturated aqueous sodium chloride solution, and then dried. The solvent was evaporated out in vacuo to obtain the entitled compound (370 mg) as an oil.

$^1$H-NMR (CDCl$_3$) δ: 1.48–1.94 (6H,m), 2.32–2.60 (3H, m), 2.96–3.16 (2H,m), 3.83 (6H,s), 3.89 (6H,s), 3.98 (2H, t,J=6.4 Hz), 4.62 (2H,s), 6.89 (2H,d,J=8.6 Hz), 7.29 (2H,d, J=8.6 Hz).

Reference Example 33
4-[4-(4,5,6,7-Tetramethoxyindan-2-yl)butoxy]benzoic acid

An aqueous sodium hydroxide solution (3 N, 1.04 ml, 3.12 mmols) was added to a methanol (10 ml) solution of methyl 4-[4-(4,5,6,7-tetramethoxyindan-2-yl)butoxy] benzoate (920 mg, 2.07 mmols), and heated under reflux for 6 hours. Water was added to the reaction mixture, which was made acidic by adding 1 N hydrochloric acid and extracted with ethyl acetate. The organic layer was washed with a saturated aqueous sodium chloride solution, and then dried. The solvent was evaporated out in vacuo, and the resulting crude product was purified by recrystallization (from hexane-ethyl acetate) to obtain the entitled compound (855 mg) as crystals.

m.p.: 136–138° C.

Reference Example 34
N,N-Dimethyl-4-[4-(4,5,6,7-tetramethoxyindan-2-yl) butoxy]benzamide A THF (16 ml) suspension of 4-[4-(4,5,6,7-tetramethoxyindan-1-yl)butoxy]benzoic acid (400 mg, 0.929 mmols), dimethylammonium chloride (150 mg, 1.86 mmols), 1-ethyl-3-(3-dimethylaminopropyl)carbodiimide hydrochloride (357 mg, 1.86 mmols), 1-hydroxybenzotriazole monohydrate (285 mg, 1.86 mmols) and triethylamine (0.777 ml, 5.57 mmols) was stirred at room temperature for 12 hours. Water was added to the reaction mixture, which was then extracted with ethyl acetate. The organic layer was washed with a saturated aqueous sodium chloride solution, and then dried. The solvent was evaporated out in vacuo, and the resulting crude product was purified by alumina column chromatography (ethyl acetate) followed by recrystallization (from hexane-ethyl acetate) to obtain the entitled compound (408 mg) as crystals.

m.p.: 99–102° C.

Reference Example 35
8-(4,5,6,7-Tetramethoxyindan-2-yl)octyl acetate

To a solution of 8-(4,5,6,7-tetramethoxyindan-2-yl) octanol (1.20 g) in pyridine (6.0 ml) was dropwise added anhydrous acetic acid (0.555 ml) at room temperature. After being stirred for 12 hr, the reaction mixture was concentrated in vacuo, made acidic with 1N hydrochloric acid, and extracted with ethyl acetate. The organic layer was washed with 1N hydrochloric acid, water, and saturated aqueous sodium chloride, and dried. The solvent was removed in vacuo. The resulting residue was purified by silica gel column chromatography (hexane:ethyl acetate=10:1) to yield the entitled compound (1.25 g) as crystals.

m.p.: 47–48° C.

Reference Example 36
8-(4,5,6,7-Tetramethoxyindan-2-yl)octyl N-ethylcarbamate

To a solution of 8-(4,5,6,7-tetramethoxyindan-2-yl) octanol (1.20 g) and ethyl isocyanate (0.517 ml) in THF (12 ml) was added one drop of pyridine. After being stirred for 12 hr at 40° C., the reaction mixture was concentrated in vacuo. The residue was purified by silica gel column chromatography (hexane:ethyl acetate=2:1) to yield the entitled compound (1.42 g) as crystals.

m.p.: 85–86° C.

Reference Example 37
8-(4,5,6,7-Tetramethoxyindan-2-yl)octyl methanesulfonate

To a solution of 8-(4,5,6,7-tetramethoxyindan-2-yl) octanol (1.95 g) and triethylamine (1.11 ml) in acetonitrile (20 ml) was dropwise added methanesufonyl chloride (0.494 ml) with cooling with ice. After the stirring was continued for 15 min, saturated aqueous sodium bicarbonate was added to the reaction mixture, which was then extracted with ethyl acetate. The organic layer was washed with saturated aqueous sodium bicarbonate, water, and saturated aqueous sodium chloride, and dried. The solvent was removed in vacuo to yield the entitled compound (2.36 g) as an oil.

$^1$H-NMR (CDCl$_3$) δ: 1.16–1.86(14H, m), 2.28–2.58(3H, m), 2.90–3.18(2H, m), 3.01(3H, s), 3.83(6H, s), 3.89(6H, s), 4.23(2H, t).

Reference Example 38
2-(8-Iodooctyl)-4,5,6,7-tetramethoxyindan

The mixture of 8-(4,5,6,7-tetramethoxyindan-2-yl)octyl methanesulfonate (2.36 g), sodium iodide (2.38 g) in acetone (20 ml) was heated under reflux for 3 hr. Water was added to the reaction mixture, which was then extracted with ethyl acetate. The organic layer was washed with 5% aqueous sodium sulfite, water, and saturated aqueous sodium chloride, and dried. The solvent was removed in vacuo to yield the entitled compound (2.44 g) as an oil.

$^1$H-NMR (CDCl) δ: 1.16–1.94(14H, m), 2.28–2.58(3H, m), 2.94–3.16(2H, m), 3.19(2H, t), 3.83(6H, s), 3.89(6H, s).

Reference Example 39
N-[8-(4,5,6,7-Tetramethoxyindan-2-yl)octyl]-N,N-dimethylamine The mixture of 2-(8-iodooctyl)-4,5,6,7-tetramethoxyindan (1.20 g), dimethylamine hydrochloride (411 mg) and potassium carbonate (1.74 g) in DMF (12 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (hexane to hexane:ethyl acetate= 10:1) to yield the entitled compound (620 mg) as an oil.

$^1$H-NMR (CDCl$_3$) δ: 1.16–1.94(14H, m), 2.10–2.60(5H, m), 2.21(6H, s), 2.92–3.16(2H, m), 3.83(6H, s), 3.89(6H, s).

Reference Example 40
1-[8-(4,5,6,7-Tetramethoxyindan-2-yl)octyl]-4-phenylpiperidine hydrochloride The mixture of 2-(8-iodooctyl)-4,5,6,7-tetramethoxyindan (1.00 g), 4-phenylpiperidine (711 mg) and potassium carbonate (1.45 g) in DMF (10 ml) was stirred at room temperature for 12 hr. The reaction mixture was diluted with water and extracted with ethyl acetate. The organic layer was washed with water and saturated aqueous sodium chloride, and dried. The solvent was removed in vacuo. The residue was purified by alumina column chromatography (hexane to hexane:ethyl acetate=20:1) and converted into its hydrochloride, which was then recrystallized from ethanol-diisopropylether to yield the entitled compound (860 mg) as crystals.

m.p.: 183–185° C.

Reference Example 41
N-[8-(4,5,6,7-Tetramethoxyindan-2-yl)octyl]phthalimide

To a solution of 2-(8-iodooctyl)-4,5,6,7-tetramethoxyindan (1.98 g) in DMF (10 ml) was dropwise added potassium phthalimide (924 mg). After being stirred at room temperature for 12 hr, the reaction mixture was diluted with ethyl acetate. The organic layer was washed with water and saturated aqueous sodium chloride and dried. The solvent was removed in vacuo and the residue was purified by alumina column chromatography (hexane to hexane:ethyl acetate=10:1) and then recrystallized from hexane gave the entitled compound (1.74 g) as crystals.

m.p.: 64–65° C.

Reference Example 42
N-[8-(4,5,6,7-Tetramethoxyindan-2-yl)octyl]amine

The mixture of N-[8-(4,5,6,7-tetramethoxyindan-2-yl)octyl]phthalimide (384 mg), hydrazine monohydrate (194 mg) in ethanol (8 ml) was heated under reflux for 6 hr. The reaction mixture was cooled to room temperature and solid was filtered off and the filtrate was concentrated. The residue was diluted with ethyl acetate, washed with 1M aqueous potassium carbonate, water, and saturated aqueous sodium chloride, and dried. The solvent was removed in vacuo to yield the entitled compound (260 mg) as an oil.

$^1$H-NMR (CDCl$_3$) δ: 1.16–1.60(14H, m), 2.28–2.80(5H, m), 2.94–3.16(2H, m), 3.83(6H, s), 3.89(6H, s).

Reference Example 43
N-[8-(4,5,6,7-Tetramethoxyindan-2-yl)octyl]acetamide

To a mixture of 8-(4,5,6,7-tetramethoxyindan-2-yl)octylamine (878 mg), potassiumcarbonate (2.54 g),water (16 ml), and ethyl acetate (16 ml) was dropwise added acetyl chloride (0.341 ml) with cooling with ice. After being stirred for 15 min, the reaction mixture was extracted with ethyl acetate. The organic layer was washed with water and saturated aqueous sodium chloride and dried. The solvent was removed in vacuo. The residue was purified by silica gel column chromatography (ethyl acetate) and then with recrystallization (hexane-ethyl acetate) to give the entitled compound (0.830 g) as crystals.

m.p.: 57–61° C.

Reference Example 44
1-[8-(4,5,6,7-Tetramethoxyindan-2-yl)octyl]-4-(2-pyridyl)piperazine The mixture of 2-(8-iodooctyl)-4,5,6,7-tetramethoxyindan (1.20 g), 1-(2-pyridyl)piperazine (823 mg), and potassium carbonate (1.04 g) in DMF (12 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (hexane to hexane:ethyl acetate=10:1) to yield the entitled compound (1.16 g) as an oil.

$^1$H-NMR (CDCl$_3$) δ: 1.16–1.86(14H, m), 2.26–2.64(9H, m), 2.94–3.16(2H, m), 3.56(4H, t), 3.83(6H, s), 3.89(6H, s), 6.56–6.70(2H, m), 7.40–7.54(1H, m), 8.14–8.24(1H, m).

Reference Example 45
1-[8-(4,5,6,7-Tetramethoxyindan-2-yl)octyl]-4-piperidinopiperidine dihydrochloride The mixture of 2-(8-iodooctyl)-4,5,6,7-tetramethoxyindan(1.18 g), 4-piperidinopiperidine (835 mg), and potassium carbonate (1.03 g) in DMF (10 ml) was stirred at room temperature for 12 hr. The reaction mixture was diluted with water and extracted with ethyl acetate. The organic layer was washed with water and saturated aqueous sodium chloride, and dried. The solvent was removed in vacuo. The residue was purified by alumina column chromatography (hexane to hexane:ethyl acetate=4:1) and converted into its hydrochloride, which was further recrystallized from ethanol-ethyl acetate to yield the entitled compound (1.08 g) as crystals.

m.p.: 220° C. (decomposed).

Reference Example 46
1-[8-(4,5,6,7-Tetramethoxyindan-2-yl)octyl]-4-diphenylmethylpiperazine The mixture of 2-(8-iodooctyl)-4,5,6,7-tetramethoxyindan (1.17 g), 1-diphenylmethylpiperazine (1.24 g) and potassium carbonate (1.70 g) in DMF (10 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (hexane to hexane:ethyl acetate=10:1) to yield the entitled compound (1.19 g) as an oil.

$^1$H-NMR(CDCl$_3$) δ: 1.16–1.74(14H, m), 2.24–2.60(13H, m), 2.94–3.16(2H, m), 3.82(6H, s), 3.89(6H, s), 4.21(1H, s), 7.10–7.46(10H, m).

Reference Example 47
4-[8-(4,5,6,7-Tetramethoxyindan-2-yl)octyl]morpholine hydrochloride The mixture of 2-(8-iodooctyl)-4,5,6,7-tetramethoxyindan (806 mg), morpholine (294 mg), and potassium carbonate (467 mg) in DMF (8 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (hexane:ethyl acetate=10:1) and converted into its hydrochloride, which was further recrystallized from ethanol-diisopropylether to yield the entitled compound (556 mg) as crystals.

m.p.: 123–124° C.

Reference Example 48
4-Benzyl-1-[8-(4,5,6,7-tetramethoxyindan-2-yl)octyl]piperazine dihydrochloride 2-(8-Iodooctyl)-4,5,6,7-tetramethoxyindan (830 mg), 1-benzylpiperazine (613 mg), potassium carbonate (481 mg) in DMF (8 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (hexane to hexane:ethyl acetate=4:1) and converted into its hydrochloride, which was further recrystallized from ethanol-diisopropylether to yield the entitled compound (870 mg) as crystals.

m.p.: 208–212° C.

Reference Example 49
2-[8-(4-Chlorophenoxy)octyl]-4,5,6,7-tetramethoxyindan

The mixture of 2-(8-iodooctyl)-4,5,6,7-tetramethoxyindan (830 mg), 4-chlorophenol (269 mg), and potassium carbonate (481 mg) in DMF (8 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (hexane to hexane:ethyl acetate=10:1) to yield the entitled compound (776 mg) as crystals.

m.p.: 38–42° C.

Reference Example 50
Ethyl 4-(3-chloropropoxy)benzoate

The mixture of ethyl 4-hydroxybenzoate(50.0 g), 1-bromo-3-chloropropane (56.8 g), and potassium carbonate (125 g) in acetonitrile (500 ml) was stirred 40° C. for 48 hr. The reaction mixture was concentrated and the residue was diluted with water, then extracted with diethyl ether. The organic layer was washed with water and saturated aqueous sodium chloride and dried. The solvent was removed in vacuo. The residue was purified by alumina column chromatography (hexane to hexane:ethyl acetate=20:1) to yield the entitled compound (66.5 g) as an oil.

$^1$H-NMR (CDCl$_3$) δ: 1.38(3H, t), 2.14–2.40(2H, m), 3.75(2H, t), 4.17(2H, t), 4.35(2H, q), 6.92(2H, d), 8.00(2H, d).

Reference Example 51
Ethyl 4-(3-iodopropoxy)benzoate

The mixture of ethyl 4-(3-chloropropoxy)benzoate (26.5 g), sodium iodide (49.0 g) in acetone (300 ml) was heated under reflux for 24 hr. The reaction mixture was diluted with water and extracted with diethyl ether. The organic layer was washed with 5% aqueous sodium sulfite, water, saturated aqueous sodium chloride, and dried. The solvent was removed in vacuo to yield the entitled compound (34.4 g) as an oil.

$^1$H-NMR (CDCl$_3$) δ: 1.38(3H, t), 2.18–2.42(2H, m), 3.37(2H, t), 4.10(2H, t), 4.35(2H, q), 6.92(2H, d), 8.00(2H, d).

Reference Example 52
Ethyl 2-ethoxycarbonyl-5-(4-ethoxycarbonylphenoxy)pentanoate To a solution of sodium ethoxide (90%, 6.79 g) in ethanol (250 ml) was dropwise added ethyl malonate (12.0 g) with cooling with ice. The reaction mixture was allowed to warm to room temperature and stirred for 30 min and ethyl 4-(3-iodopropoxy)benzoate (25.0 g) was dropwise added with cooling with ice. The reaction mixture was allowed to warm to room temperature and stirred for 12 hr. The reaction mixture was diluted with water and extracted with ethyl acetate. The organic layer was washed with water and saturated aqueous sodium chloride and dried. The solvent was removed in vacuo. The residue was purified by silica gel column chromatography (hexane to hexane:ethyl acetate=10:1) to yield the entitled compound (13.0 g) as an oil.

$^1$H-NMR (CDCl$_3$) δ: 1.27(6H, t), 1.38(3H, t), 1.77–1.97 (2H, m), 2.00–2.20(2H, m), 3.42(1H, t), 4.04(2H, t), 4.21 (4H, q), 4.35(2H, q), 6.90(2H, d), 7.99(2H, d).

Reference Example 53
Ethyl 3-(2-bromo-3,4,5,6-tetramethoxyphenyl)-2-ethoxycarbonyl-2-[3-(4-ethoxycarbonylphenoxy)propyl]propionate To a solution of ethyl 2-ethoxycarbonyl-5-(4-ethoxycarbonylphenoxy)pentanoate (25.9 g) in DMF (200 ml) was portionwise added sodium hydride (60% oil dispersion, 3.11 g) with cooling with ice. The reaction mixture was allowed to warm to room temperature and stirred for 30 min. To the reaction mixture was dropwise added a solution of 1-bromo-6-bromomethyl-2,3,4,5-tetramethoxybenzene (28.8 g) in DMF (50 ml) with cooling with ice. The reaction mixture was allowed to warm to room temperature and stirred for 6 hr. The reaction mixture was diluted with water and extracted with diethyl ether. The organic layer was washed with water and saturated aqueous sodium chloride and dried. The solvent was removed in vacuo. The residue was purified by silica gel column chromatography (hexane to hexane:ethyl acetate=7:1) to yield the entitled compound (42.6 g) as an oil.

$^1$H-NMR (CDCl$_3$) δ: 1.25(6H, t), 1.38(3H, t), 1.70–2.00 (4H, m), 3.56(2H, s), 3.73(3H, s), 3.81(3H, s), 3.80–4.04 (2H, m), 3.87(3H, s), 3.93(3H, s), 4.08–4.30(4H, m), 4.34 (2H, q), 6.86(2H, d), 7.97(2H, d).

Reference Example 54
Ethyl 2-[3-(4-ethoxycarbonylphenoxy)propyl]-4,5,6,7-tetramethoxy-1-oxo-2-indancarboxylate To a solution of ethyl 3-(2-bromo-3,4,5,6-tetramethoxyphenyl)-2-ethoxycarbonyl-2-[3-(4-ethoxycarbonylphenoxy)propyl]propionate (40.0 g) in THF (400 ml) was dropwise added n-butyl lithium in hexane (1.68M; 41.8 ml) under nitrogen atmosphere at −100° C. or under and the solution was allowed to warm to −78° C. in 30 min. The reaction mixture was cooled to −100° C. again and a solution of acetic acid (7.33 g) in THF (20 ml) was dropwise added, which was then allowed to warm to room temperature. The reaction mixture was diluted with ethyl acetate and the organic layer was washed with saturated aqueous sodium bicarbonate, water, and saturated aqueous sodium chloride, and dried. The solvent was removed in vacuo. The residue was purified by silica gel column chromatography (hexane to hexane:ethyl acetate=7:1) to yield the entitled compound (29.7 g) as an oil.

$^1$H-NMR (CDCl$_3$) δ: 1.22(3H, t), 1.37(3H, t), 1.58–2.38 (4H, m), 2.97(1H, d), 3.60(1H, d), 3.91(6H, s), 3.94–4.10 (2H, m), 3.98(3H, s), 4.05(3H, s), 4.16(2H, q), 4.34(2H, q), 6.86(2H, d), 7.97(2H, d).

Reference Example 55
Methyl 4-[3-(4,5,6,7-tetramethoxy-1-oxoinadan-2-yl)propoxy]benzoate A solution of ethyl 2-[3-(4-ethoxycarbonylphenoxy)propyl]-4,5,6,7-tetramethoxy-1-oxo-2-indancarboxylate (14.9 g), acetic acid (75 ml), and concentrated hydrochloric acid (75 ml) was stirred at 80° C. for 6 hr and then heated under reflux for 2 hr. The reaction mixture was concentrated in vacuo and diluted with ethyl acetate. The organic layer was washed with saturated aqueous sodium chloride, and dried. The solvent was removed in vacuo and the mixture of the residue, potassium carbonate (19.5 g), iodomethane (8.77 ml) in DMF (100 ml) was stirred at room temperature for 12 hr. The reaction mixture was diluted with diethyl ether and the organic layer was washed with water and saturated aqueous sodium chloride and dried. The solvent was removed in vacuo and the residue was purified by silica gel column chromatography (hexane to hexane:ethyl acetate=5:1) and then with recrystallization from hexane-ethyl acetate to yield the entitled compound (9.85 g) as crystals.

m.p.: 68–70° C.

Reference Example 56
Methyl 4-[3-(4,5,6,7-tetramethoxyindan-2-yl)propoxy]benzoate To a solution of methyl 4-[3-(4,5,6,7-tetramethoxyl-oxoinadan-2-yl)propoxy]benzoate (9.20 g) in methanol (100 ml) was added sodium borohydride (1.57 g) with cooling with ice. The reaction mixture was allowed to warm to room temperature, stirred for 4 hr, and diluted with ethyl acetate. The organic layer was washed with water and saturated aqueous sodium chloride and dried. The solvent was removed in vacuo. The residue was dissolved in methanol (100 ml) and hydrogenated in the presence of concentrated hydrochloric acid (0.041 ml) and 10% palladium-carbon (1.84 g) under hydrogen atmosphere (1 atm) at room temperature for 12 hr. The catalyst was filtered off and the filtrate was concentrated in vacuo. The residue was purified by silica gel column chromatography (hexane to hexane-:ethyl acetate=8:1) and then with recrystallization from hexane gave the entitled compound (7.85 g) as crystals.

m.p.: 70–72° C.

Reference Example 57

4-[3-(4,5,6,7-Tetramethoxyindan-2-yl)propoxy]benzoic acid

To a solution of methyl 4-[3-(4,5,6,7-tetramethoxyindan-2-yl)propoxy]benzoate (7.35 g) in methanol (74 ml) was dropwise added aqueous sodium hydroxide (3N, 8.57 ml), which was heated under reflux for 6 hr. The reaction mixture was concentrated in vacuo, made acidic with 1N hydrochloric acid, and extracted with ethyl acetate. The organic layer was washed with water and saturated aqueous sodium chloride and dried. The solvent was removed in vacuo. The residue was recrystallized from hexane-ethyl acetate to yield the entitled compound (6.58 g) as crystals.

m.p.: 160–161° C.

Reference Example 58

N,N-Dimethyl-4-[3-(4,5,6,7-tetramethoxyindan-2-yl) propoxy]benzamide

The mixture of 4-[3-(4,5,6,7-tetramethoxyindan-2-yl)propoxy]benzoic acid (2.00 g), dimethylammonium hydrochloride (783 mg), 1-ethyl-3-(3-dimethylaminopropyl) carboduimide hydrochloride (1.84 g), 1-hydroxybenzotriazole monohydrate (1.47 g), and triethylamine (4.01 ml) in THF (40 ml) was stirred at room temperature for 12 hr. The reaction mixture was diluted with ethyl acetate and the organic layer was washed with water and saturated aqueous sodium chloride and dried. The solvent was removed in vacuo. The residue was purified by silica gel column chromatography (hexane:ethyl acetate=1:2 to ethyl acetate) to yield the entitled compound (2.12 g) as an oil.

$^1$H-NMR (CDCl$_3$) δ: 1.56–2.00(4H, m), 2.36–2.64(3H, m), 2.94–3.22(8H, m), 3.84(6H, s), 3.89(6H, s), 4.02(2H, d), 6.90(2H, d), 7.40(2H, d).

Reference Example 59

4,5,6,7-Tetramethoxy-2-[3-(4-dimethylaminomethylphenoxy)propyl]indan hydrochloride To a solution of N, N-dimethyl-4-[3-(4,5,6,7-tetramethoxyindan-2-yl)propoxy]benzamide (1.34 g) in THF (13 ml) was added lithium aluminum hydride (229 mg). After being heated under reflux for 1 hr, the reaction mixture was treated with saturated aqueous Rochelle salt at room temperature. The precipitate was filtered off and the filtrate was concentrated in vacuo. The residue was purified by alumina column chromatography (hexane to hexane-:ethyl acetate=4:1) and converted into its hydrochloride, which was further recrystallized from ethanol-diisopropylether to yield the entitled compound (1.17 g) as crystals.

m.p.: 172–175° C.

Reference Example 60

4,5,6,7-Tetramethoxy-2-[3-[4-[(4-piperidinopiperidino) carbonyl]phenoxy]propyl]indan hydrochloride The mixture of 4-[3-(4,5,6,7-tetramethoxyindan-2-yl) propoxy]benzoic acid (2.00 g), 4-piperidinopiperidine (1.62 g), 1-ethyl-3-(3-dimethylaminopropyl)carbodiimide hydrochloride (1.84 g), 1-hydroxybenzotriazole monohydrate (1.47 g), and triethylamine (2.01 ml) in THF (40 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (hexane to hexane:ethyl acetate=1:2) and converted into its hydrochloride, which was further recrystallized from ethanol-diisopropylether to yield the entitled compound (2.85 g) as crystals.

m.p.: 201–204° C.

Reference Example 61

4,5,6,7-Tetramethoxy-2-[3-[4-[(4-piperidinopiperidino) methyl]phenoxy]propyl]indan dihydrochloride To a suspension of lithium aluminum hydride (200 mg) in THF (15 ml) was dropwise added a solution of 4,5,6,7-tetramethoxy-2-[3-[4-[(4-piperidinopiperidino)carbonyl] phenoxy]propyl]indan (1.49 g) in THF (10 ml). After being heated under reflux for 1 hr, the reaction mixture was treated with saturated aqueous Rochelle salt at room temperature. The precipitate was filtered off and the filtrate was concentrated in vacuo. The residue was purified by alumina column chromatography (hexane to hexane:ethyl acetate=4:1) and converted into its hydrochloride, which was then recrystallized from ethanol to yield the entitled compound (1.11 g) as crystals.

m.p.: 259–266° C. (decomposed).

Reference Example 62

2,3,4,5-Tetramethoxy-6-methylbenzaldehyde

To a solution of 1,2,3,4-tetramethoxy-5-methylbenzene (20.0 g) in methylene chloride (100 ml) was dropwise added titanium tetrachloride (20.6 ml) with cooling with ice, followed by addition of 1,1-dichlorodimethylether (11.0 ml) with cooling with ice. The reaction mixture was allowed to warm to room temperature and further stirred for 8 hr. The reaction mixture was poured into ice-water, and extracted with diethyl ether. The organic layer was washed with water and saturated aqueous sodium chloride and dried. The solvent was removed in vacuo and the residue was purified by silica gel column chromatography (hexane to hexane-:ethyl acetate=10:1) to give the entitled compound(21.5 g) as an oil.

$^1$H-NMR (CDCl$_3$) δ: 2.46(3H, s), 3.77(3H, s), 3.91(3H, s), 3.95(3H, s), 4.03(3H, s), 10.44(1H, s).

Reference Example 63

2,3,4,5-Tetramethoxy-6-methylphenylmethanol

To a suspension of lithium aluminum hydride (2.37 g) in diethyl ether (150 ml) was dropwise added a solution of 2,3,4,5-tetramethoxy-6-methylbenzaldehyde (15.0 g) in diethyl ether (30 ml) with cooling with ice. After the reaction mixture was stirred for 30 min, 10% hydrochloric acid was added to the reaction mixture, which was diluted with water and extracted with ethyl acetate. The organic layer was washed with water and saturated aqueous sodium chloride and dried. The solvent was removed in vacuo. The residue was purified by silica gel column chromatography (hexane to hexane:ethyl acetate=2:1) to yield the entitled compound (14.2 g) as an oil.

$^1$H-NMR (CDCl$_3$) δ: 2.27(3H, s), 3.79(3H, s), 3.89(3H, s), 3.90(3H, s), 3.92(3H, s), 4.62–4.74(2H, m).

Reference Example 64
5-Bromomethyl-1,2,3,4-tetramethoxy-6-methylbenzene

To a solution of 2,3,4,5-tetramethoxy-6-methylphenylmethanol (44.4 g) in THF (200 ml) was dropwise added phosphorus tribromide (29.8 g) with cooling with ice. After being stirred for 1 hr, the reaction mixture was poured into ice-water and extracted with ethyl acetate. The organic layer was washed with saturated aqueous sodium bicarbonate, water, and saturated aqueous sodium chloride, and dried. The solvent was removed in vacuo to yield the entitled compound (54.4 g) as an oil.

$^1$H-NMR (CDCl$_3$) δ: 2.27(3H, s), 3.79(3H, s), 3.89(3H, s), 3.93(3H, s), 3.95(3H, s), 4.61(2H, s).

Reference Example 65
5,6-Bis(bromomethyl)-1,2,3,4-tetramethoxybenzene

A solution of 1-bromomethyl-1,2,3,4-tetramethoxy-6-methylbenzene (54.4 g), NBS (34.7 g), and AIBN (585 mg) in ethyl acetate (500 ml) was heated under reflux for 1.5 hr, followed by further addition of NBS (6.31 g) and AIBN (117 mg). The reflux was continued for additional 1.5 hr. The reaction mixture washed with water, saturated aqueous sodium bicarbonate, water, and saturated aqueous sodium chloride, and dried. The solvent was removed in vacuo and the entitled compound (68.0 g) as an oil.

$^1$H-NMR (CDCl$_3$) δ: 3.93(6H, s), 3.95(6H, s), 4.72(4H, s).

Reference Example 66
1,2,3,4-Tetramethoxy-6,7,8,9-tetrahydro-5H-benzo[a]cyclohepten-7-one To a solution of 5,6-bis(bromomethyl)-1,2,3,4-tetramethoxybenzene (44.5 g) and diethyl 1,3-acetonedicrboxylate (46.9 g) in acetonitrile (450 ml) was added potassium carbonate (48.1 g) with cooling with ice. After being stirred for 30 min, the reaction mixture was allowed to warm to room temperature and stirred for additional 12 hr. The reaction mixture was diluted with water, made acidic with concentrated hydrochloric acidic, and extracted with ethyl acetate. The organic layer was washed with saturated aqueous sodium chloride, and dried The solvent was removed in vacuo. The residue was dissolved in acetic acid (333 ml) followed by addition of concentrated hydrochloric acid (111 ml) and the stirring was continued at 100° C. for 1 hr. The reaction mixture was concentrated in vacuo, diluted with water, and extracted with ethyl acetate. The organic layer was washed with saturated aqueous sodium bicarbonate, water, and saturated aqueous sodium chloride, and dried. The solvent was removed in vacuo. The residue was purified by alumina column chromatography (ethyl acetate) and then with recrystallization from hexane-ethyl acetate to yield the entitled compound (23.4 g) as crystals.

m.p.: 77–78° C.

Reference Example 67
Ethyl 2-(1,2,3,4-tetramethoxy-6,7,8,9-tetrahydro-5H-benzo[a]cyclohepten-7-ylidene)acetate Sodium hydride (60% oil dispersion, 1.42 g) was added to THF (30 ml) followed by addition of ethyl diethyl phosphonoacetate (7.98 g) with cooling with ice and the stirring was continued for 15 min. The reaction mixture was allowed to warm to room temperature and further stirred for 1 hr, followed by addition of a solution of 1,2,3,4-tetramethoxy-6,7,8,9-tetrahydro-5H-benzo[a]cyclohepten-7-one (5.00 g) in THF (20 ml) at room temperature. After being stirred for further 1 hr, the reaction mixture was diluted with water and extracted with ethyl acetate. The organic layer was washed with water and saturated aqueous sodium chloride and dried. The solvent was removed in vacuo. The residue was purified by silica gel column chromatography (hexane to hexane:ethyl acetate=10:1) to yield the entitled compound (5.72 g) as crystals.

m.p.: 61–63° C.

Reference Example 68
Ethyl 2-(1,2,3,4-Tetramethoxy-6,7,8,9-tetrahydro-5H-benzo[a]cyclohepten-7-yl)acetate To a solution of 2-(1,2,3,4-tetramethoxy-6,7,8,9-tetrahydro-5H-benzo[a]cyclohepten-7-ylidene)ethyl acetate (5.50. g) in ethanol (110 ml) was added 10% palladium-carbon (550 mg), which was stirred under hydrogen atmosphere (1 atm) at room temperature for 12 hr. The catalyst was filtered off and the filtrate was concentrated in vacuo. The residue was purified by silica gel column chromatography (hexane to hexane:ethyl acetate=10:1) to yield the entitled compound (5.44 g) as an oil.

$^1$H-NMR (CDCl$_3$) δ: 0.90–1.24(2H, m), 1.27(3H, t), 1.88–2.54(7H, m), 3.14–3.34(2H, m), 3.75(6H, s), 3.91(6H, s), 4.14(2H, q).

Reference Example 69
2-(1,2,3,4-Tetramethoxy-6,7,8,9-tetrahydro-5H-benzo[a]cyclohepten-7-yl)ethanol To a suspension of lithium aluminum hydride (486 mg) in diethyl ether (20 ml) was dropwise added a solution of 2-(1,2,3,4-tetramethoxy-6,7,8,9-tetrahydro-5H-benzo[a]cyclohepten-7-yl)ethyl acetate (3.00 g) in diethyl ether (10 ml) with cooling with ice. After the reaction mixture stirred for 30 min, 10% hydrochloric acid was added to the reaction mixture, which was diluted with water and extracted with ethyl acetate. The organic layer was washed with water, saturated aqueous sodium bicarbonate, water, and saturated aqueous sodium chloride, and dried. The solvent was removed in vacuo. The residue was purified by silica gel column chromatography (hexane to hexane:ethyl acetate=1:1) to yield the entitled compound (2.60 g) as crystals.

m.p.: 64–66° C.

Reference Example 70
2-(1,2,3,4-Tetramethoxy-6,7,8,9-tetrahydro-5H-benzo[a]cyclohepten-7-yl)ethyl methanesulfonate To a solution of 2-(1,2,3,4-tetramethoxy-6,7,8,9-tetrahydro-5H-benzo[a]cyclohepten-7-yl)ethanol (2.50 g) and triethylamine (1.68 ml) in acetonitrile (50 ml) was dropwise added methanesufonyl chloride (0.750 ml) with cooling with ice. After the reaction mixture was stirred for 15 min, saturated aqueous sodium bicarbonate was added to the solution with cooling with ice, which was extracted with ethyl acetate. The organic layer was washed with 1N hydrochloric acid, water, saturated aqueous sodium bicarbonate, water, and saturated aqueous sodium chloride, and dried. The solvent was removed in vacuo to yield the entitled compound (3.12 g) as an oil.

$^1$H-NMR (CDCl$_3$) δ: 0.92–1.20(2H, m), 1.60–2.10(5H, m), 2.28–2.52(2H, m), 3.02(3H, s), 3.16–3.36(2H, m), 3.76 (6H, s), 3.91(6H, s), 4.29(2H, t).

Reference Example 71
7-(2-Iodoethyl)-1,2,3,4-tetramethoxy-6,7,8,9-tetrahydro-5H-benzo[a]cycloheptene The mixture of 2-(1,2,3,4-tetramethoxy-6,7,8,9-tetrahydro-5H-benzo[a]cyclohepten-7-yl)ethyl methanesulfonate (3.12 g), sodium iodide (3.61 g), and acetone (40 ml) was heated under reflux for 1 hr. The reaction mixture was diluted with water and extracted with ethyl acetate. The organic layer was washed with 5% aqueous sodium sulfite, water, and saturated aqueous sodium chloride, and dried.

The solvent was removed in vacuo to yield the entitled compound (3.29 g) as crystals.

m.p.: 75–82° C.

Reference Example 72
2-(1,2,3,4-Tetramethoxy-6,7,8,9-tetrahydro-5H-benzo[a] cyclohepten-7-yl)acetic acid To a solution of 2-(1,2,3,4-tetramethoxy-6,7,8,9-tetrahydro-5H-benzo[a]cyclohepten-7-yl)ethyl acetate (2.29 g) in methanol (23 ml) was dropwise added aqueous sodium hydroxide (3N, 3.25 ml) and the reaction mixture was heated under reflux for 6 hr. The reaction mixture was concentrated in vacuo, made acidic with 1N hydrochloric acid, and extracted with ethyl acetate. The organic layer was washed with water and saturated aqueous sodium chloride and dried. The solvent was removed in vacuo. The residue was recrystallized from hexane-ethyl acetate to yield the entitled compound (1.81 g) as crystals.

m.p.: 109–111° C.

Reference Example 73
Ethyl 4-[2-(1,2,3,4-Tetramethoxy-6,7,8,9-tetrahydro-5H-benzo[a]cyclohepten-7-yl)ethoxy]benzoate The mixture of 7-(2-iodoethyl)-1,2,3,4-tetramethoxy-6,7,8,9-tetrahydro-5H-benzo[a]cycloheptene (1.00 g), 4-hydroxybenzoate (593 mg), potassium carbonate (987 mg), and DMF (10 ml) was stirred at room temperature for 12 hr. The reaction mixture was diluted with water and extracted with ethyl acetate. The organic layer was washed with water and saturated aqueous sodium chloride, and dried. The solvent was removed in vacuo. The residue was purified by alumina column chromatography (hexane to hexane:ethyl acetate=15:1) and then with recrystallization from hexane-ethyl acetate to yield the entitled compound (910 mg) as crystals.

m.p.: 129–131° C.

Reference Example 74
4-[2-(1,2,3,4-Tetramethoxy-6,7,8,9-tetrahydro- 5H-benzo [a]cyclohepten-7-yl)ethoxy]phenylmethanol To a suspension of lithium aluminum hydride (91.8 mg) in diethyl ether (10 ml) was dropwise added a solution of ethyl 4-[2-(1,2,3,4-tetramethoxy-6,7,8,9-tetrahydro-5H-benzo[a]cyclohepten-7-yl)ethoxy]benzoate (553 mg) in THF (10 ml) with cooling with ice. After stirring was continued for 15 min, 10% hydrochloric acid was added to the reaction mixture, which was diluted with water and extracted with ethyl acetate. The organic layer was washed with water and saturated aqueous sodium chloride and dried. The solvent was removed in vacuo. The residue was recrystallized from hexane-ethyl acetate to yield the entitled compound (320 mg) as crystals.

m.p.: 114–116° C.

Reference Example 75
4-[2-(1,2,3,4-Tetramethoxy-6,7,8,9-tetrahydro-5H-benzo[a] cyclohepten-7-yl)ethoxy]benzoic acid The mixture of ethyl 4-[2-(1,2,3,4-tetramethoxy-6,7,8,9-tetrahydro-5H-benzo[a]cyclohepten-7-yl)ethoxy]benzoate (1.77 g), aqueous sodium hydride (3N, 1.93 ml), and methanol (30 ml) was heated under reflux for 6 hr. The reaction mixture was concentrated in vacuo, diluted with water, made acidic with hydrochloric acid, and extracted with ethyl acetate. The organic layer was washed with water and saturated aqueous sodium chloride and dried. The solvent was removed in vacuo. The residue was recrystallized from THF-diisopropylether to yield the entitled compound (1.34 g) as crystals.

m.p.: 190–192° C.

Reference Example 76
7-[2-(4-Chlorophenoxy)ethyl]-1,2,3,4-tetramethoxy-6,7,8, 9-tetrahydro-5H-benzo[a]cycloheptene The mixture of 7-(2-iodoethyl)-1,2,3,4-tetramethoxy-6,7, 8,9-tetrahydro-5H-benzo[a]cycloheptene (1.64 g), 4-chlorophenol (602 mg), potassium carbonate (1.08 g), and DMF (16 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (toluene) to yield the entitled compound (1.58 g) as crystals.

m.p.: 98–102° C.

Reference Example 77
7-[2-(4-Phenylphenoxy)ethyl]-1,2,3,4-tetramethoxy-6,7,8, 9-tetrahydro-5H-benzo[a]cycloheptene The mixture of 7-(2-iodoethyl)-1,2,3,4-tetramethoxy-6,7, 8,9-tetrahydro-5H-benzo[a]cycloheptene(1.64 g),4-hydroxybiphenyl (797 mg), potassium carbonate (1.08 g), and DMF (16 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (toluene) to yield the entitled compound (1.73 g) as crystals.

m.p.: 115–120° C.

Reference Example 78
1-(tert-Butyl)-1,1-dimethylsilyl (8-chlorooctyl)ether

To a solution of 8-chlorooctanol (24.3 g) and tert.-butyldimethylchlorosilane (26.8 g) in DMF (250 ml) was dropwise added imidazole (25.2 g) with cooling with ice. The reaction mixture was allowed to warm to room temperature and stirring was continued for additional 12 hr. The reaction mixture was diluted with diethyl ether and the organic layer was washed with water and saturated aqueous sodium chloride and dried. The solvent was removed in vacuo. The residue was purified by silica gel column chromatography (hexane to hexane:diethyl ether=25:1) to yield the entitled compound (40.7 g) as an oil.

$^1$H-NMR (CDCl$_3$) δ: 0.05(6H, s), 0.89(9H, s), 1.20–1.86 (12H, m), 3.53(2H, t), 3.60(2H, t).

Reference Example 79
1-(tert-Butyl)-1,1-dimethylsilyl (8-iodooctyl) ether

The mixture of 1-(tert-butyl)-1,1-dimethylsilyl (8-chlorooctyl) ether (40.7 g), sodium iodide (43.8 g) and acetone (400 ml) was heated under reflux for 12 hr. The reaction mixture was concentrated in vacuo, diluted with water, and extracted with diethyl ether. The organic layer was washed with 5% aqueous sodium sulfite, water, and saturated aqueous sodium chloride, and dried. The solvent was removed in vacuo. The residue was purified by silica gel column chromatography (hexane to hexane:diethyl ether= 25:1) to yield the entitled compound (36.4 g) as an oil.

$^1$H-NMR (CDCl$_3$) δ: 0.05(6H, s), 0.89(9H, s), 1.14–1.94 (12H, m), 3.19(2H, t), 3.60(2H, t).

Reference Example 80
Ethyl 10-[[1-(tert-butyl)-1,1-dimethylsilyl]oxy]-2-phenyldecanoate To THF(100 ml) was dropwise added a solution of LDA in heptane (2.00M, 48.3 ml) under nitrogen atmosphere, followed by addition of a solution of phenylethyl acetate (12.2 g) in THF (10 ml) at −70° C. or under. After the reaction mixture was stirred for 30 min, a solution of 1-(tert-butyl)-1,1-dimethylsilyl (8-Iodooctyl) ether (25.0 g) in THF (10 ml) at −70° C. or under and the solution was allowed to warm to 0° C. in 15 min. Saturated aqueous sodium chloride was added to the reaction mixture, which was then extracted with diethyl ether. The organic layer was washed with saturated aqueous sodium chloride and dried. The solvent was removed in vacuo. The residue was purified by silica gel column chromatography (hexane to hexane-:ethyl acetate=30:1) to yield the entitled compound (21.2 g) as an oil.

$^1$H-NMR (CDCl$_3$) δ: 0.04(6H, s), 0.89(9H, s), 0.94–2.18 (17H, m), 3.51(1H, t), 3.58(2H, t), 4.00–4.26(2H, m), 7.16–7.36(5H, m).

Reference Example 81

Ethyl 2-(2-bromo-3,4,5,6-tetramethoxybenzyl)-10-[[1-(tert-butyl)-1,1-dimethylsilyl]oxy]-2-phenyldecanoate To THF(100 ml) was dropwise added a solution of LDA in heptane (2.00M, 33.6 ml), followed by addition of ethyl 10-[[1-(tert-butyl)-1,1-dimethylsilyl]oxy]-2-phenyldecanoate (18.2 g) in THF (20 ml) at −70° C. or under. After the reaction mixture was stirred for 30 min, a solution of 1-bromo-6-bromomethyl-2,3,4,5-tetramethoxybenzene (19.9 g) in THF (20 ml) was dropwise added to the reaction mixture at −70° C. or under, which was allowed to warm to room temperature. Saturated aqueous sodium chloride was added to the reaction mixture, which was then extracted with diethyl ether. The organic layer was washed with saturated aqueous sodium chloride, and dried. The solvent was removed in vacuo. The residue was purified by silica gel column chromatography (hexane to hexane-:ethyl acetate=30:1) to yield the entitled compound (21.2 g) as an oil.

$^1$H-NMR (CDCl$_3$) δ: 0.04(6H, s), 0.89(9H, s), 0.94–2.24 (17H, m), 3.40(1H, d), 3.58(2H, t), 3.68(3H, s), 3.68(3H, s), 3.68(1H, d), 3.84(3H, s), 3.88(3H, s), 4.16–4.30(2H, m), 7.00–7.18(5H, m).

Reference Example 82

8-(4,5,6,7-Tetramethoxy-1-oxo-2-phenylinadan-2-yl)octanol

To a solution of ethyl 2-(2-bromo-3,4,5,6-tetramethoxybenzyl)-10-[[1-(tert-butyl)-1,1-dimethylsilyl]oxy]-2-phenyldecanoate (3.00 g) in THF (30 ml) was dropwise added n-butyl lithium in hexane (1.68 M, 2.82 ml) under nitrogen atmosphere at −100° C. or under, which was then allowed to warm to −78° C. in 15 min. After the reaction mixture was stirred for 30 min, saturated aqueous sodium chloride was added to the reaction mixture, which was then extracted with diethyl ether. The organic layer was washed with saturated aqueous sodium chloride and dried. The solvent was removed in vacuo. The residue was dissolved in THF (30 ml), followed by addition of a solution of tetrabutyl ammonium fluoride in THF (1.00 M, 6.47 ml) at room temperature. After being stirred for 6 hr, the reaction mixture was passed through silica gel column chromatography followed by elution with ethyl acetate, which was further purified by silica gel column chromatography (hexane to hexane:ethyl acetate=2:1) to yield the entitled compound (1.63 g) as an oil.

$^1$H-NMR (CDCl$_3$) δ: 1.00–2.22(14H, m), 3.21(1H, d), 3.51(1H, d), 3.61(2H, t), 3.89(3H, s), 3.91(3H, s), 3.96(3H, s), 4.04(3H, s), 7.00–7.46(5H, m).

Reference Example 83

8-(4,5,6,7-Tetramethoxy-2-phenylindan-2-yl)octanol

To a suspension of lithium aluminum hydride (231 mg) in diethyl ether (14 ml), was added aluminum chloride (811 mg) with cooling with ice, which was then allowed to warm to room temperature. After being stirred for 15 min, the reaction mixture was cooled with ice, followed by addition of a solution of 8-(4,5,6,7-tetramethoxy-1-oxo-2-phenylinadan-2-yl)octanol (1.39 g) in diethylether (7 ml). After the reaction mixture was stirred for 15 min, 1N hydrochloric acid was added to the reaction mixture, which was then extracted with ethyl acetate. The organic layer was washed with water and saturated aqueous sodium chloride, and dried. The solvent was removed in vacuo. The residue was purified by silica gel column chromatography (hexane to hexane:ethyl acetate=2:1) to yield the entitled compound (1.00 g) as an oil.

$^1$H-NMR (CDCl$_3$) δ: 0.94–1.72(14H, m), 3.08–3.34(4H, m), 3.58(2H, t), 3.85(6H, s), 3.91(6H, s), 7.14–7.42(5H, m).

Reference Example 84

8-(4,5,6,7-Tetramethoxy-2-phenylindan-2-yl)octanal

To a solution of oxalyl chloride (0.394 ml) in THF (36 ml) was dropwise added a solution of dimethylsulfoxide (468 mg) in THF (2.4 ml) at −70° C. or under nitrogen atmosphere. After the reaction mixture was stirred for 10 min, a solution of 8-(4,5,6,7-tetramethoxy-2-phenylindan-2-yl)octanol (1.00 g) in THF (12 ml) was dropwise added to the reaction mixture at −70° C. or under. After being stirred for 15 min, the reaction mixture was stirred at between −60° C. and −50° C. for 1 hr, to which triethylamine (2.30 ml) was dropwise added. The reaction mixture was allowed to warm to 0° C. and stirred for 20 min, diluted with water, and extracted with ethyl acetate. The organic layer was washed with water and saturated aqueous sodium chloride and dried. The solvent was removed in vacuo. The residue was purified by silica gel column chromatography (hexane to hexane:ethyl acetate=4:1) to yield the entitled compound (985 mg) as an oil.

$^1$H-NMR (CDCl$_3$) δ: 0.90–1.70(12H, m), 2.34(2H, dt), 3.20(4H, s), 3.85(6H, s), 3.91(6H, s), 7.14–7.42(5H, m), 9.71(1H, t).

Reference Example 85

8-(4,5,6,7-Tetramethoxy-2-phenylindan-2-yl)octanoic acid

To a mixture of 8-(4,5,6,7-tetramethoxy-2-phenylindan-2-yl)octanal (985 mg), sodium dihydrogenphosphate (72.6 mg), 30% hydrogen peroxide (0.435 ml), acetonitrile (10 ml), and water (4 ml) was dropwise added a solution of sodium chlorite (80%, 355 mg) in water (14 ml) with cooling with ice in 30 min. After the reaction mixture was stirred for 30 min, aqueous sodium sulfite to the reaction mixture, which was then made acidic with 1N hydrochloric acid and extracted with ethyl acetate. The organic layer was washed with saturated aqueous sodium chloride and dried. The solvent was removed in vacuo. The residue was purified by silica gel column chromatography (hexane to hexane-:ethyl acetate=1:2) to yield the entitled compound (665 mg) as an oil.

$^1$H-NMR (CDCl$_3$) δ: 0.90–1.70(12H, m), 2.27(2H, t), 3.20(4H, s), 3.85(6H, s), 3.91(6H, s), 7.14–7.42(5H, m).

Reference Example 86

2-(8-Iodooctyl)-4,5,6,7-tetramethoxy-2-phenylindan

To a solution of 8-(4,5,6,7-tetramethoxy-2-phenylindan-2-yl)octanol (2.65 g) and triethylamine (1.25 ml) in acetonitrile (27 ml) was dropwise added methanesufonyl chloride (0.557 ml) with cooling with ice. After the reaction mixture was stirred for 15 min, saturated aqueous sodium bicarbonate was added to the reaction mixture with cooling with ice, which was extracted ethyl acetate. The organic layer was washed with water, 1N hydrochloric acid, water, and saturated aqueous sodium chloride, and dried. The solvent was removed in vacuo. The residue was heated with sodium iodide (2.70 g) in acetone (60 ml) under reflux for 3 hr. Water was added to the reaction mixture, which was then extracted with ethyl acetate. The organic layer was washed with 5% aqueous sodium sulfite, water, and saturated aqueous sodium chloride, and dried. The solvent was removed in vacuo to yield the entitled compound (3.27 g) as an oil.

$^1$H-NMR (CDCl$_3$) δ: 0.90–1.84(14H, m), 3.13(2H, t), 3.20(4H, s), 3.85(6H, s), 3.91(6H, s), 7.14–7.40(5H, m).

Reference Example 87

1-Benzyl-4-[8-(4,5,6,7-tetramethoxy-2-phenylindan-2-yl) octyl]piperazine dihydrochloride The mixture of 2-(8-iodooctyl)-4,5,6,7-tetramethoxy-2-phenylindan (800 mg),1-benzylpiperazine (511 mg) and potassium carbonate (1.00 g) in DMF (8 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (hexane to hexane:ethyl acetate=20:1) and converted into its hydrochloride, which was further recrystallized from ethanol-diisopropylether to yield the entitled compound (804 mg) as crystals.

m.p.: 218–221° C.

Reference Example 88

5,6,7-Trimethoxy-2-[6-(5,6,7-trimethoxy-1-oxo-2,3-dihydro-1H-2-indenyl)hexyl]-1-indanone To a solution of 3-(3,4,5-trimethoxyphenyl)propionic acid (12 g) in THF (200 ml) was dropwise added LDA (1.9 M/THF solution; 60 ml) while temperature of the reaction mixture was kept under –10° C. After being stirred at 0° C. for 3 hr, the reaction mixture was acidified to pH3 with 2N hydrochloric acid and extracted with ethyl acetate. The organic layer was washed with water, dried and concentrated in vacuo. Polyphosphoric acid (100 ml) was added to the residue and the reaction mixture was stirred at 60° C. for 4 hr. After being cooled, the reaction mixture was diluted with water and extracted with ethyl acetate. The organic layer was washed with saturated aqueous sodium bicarbonate and then water, dried and concentrated in vacuo. The residue was purified by alumina column chromatography (ethyl acetate) and then with crystallization from ethyl acetate-hexane to yield the entitled compound (4.5 g). The compound recrystallized from ethanol gave following melting point.

m.p.: 129–130° C.

Reference Example 89

4,5,6-Trimethoxy-2-[6-(4,5,6-trimethoxy-2,3-dihydro-1H-2-indenyl)hexyl]indan

To a solution of 5,6,7-trimethoxy-2-[6-(5,6,7-trimethoxy-1-oxo-2,3-dihydro-1H-2-indenyl)hexyl]-1-indanone in acetic acid (50 ml) were added 10% Pd—C (1 g) and perchloric acid (1 ml), and the reaction mixture was hydrogenated under hydrogen atmosphere (4 to 5 atm) at 50° C. for 6 hr. The catalyst was filtered off and the filtrate was concentrated in vacuo, and the residue was dissolved in ethyl acetate, washed with saturated aqueous sodium bicarbonate, water, dried, concentrated in vacuo. The residue was purified by silica gel column chromatography (ethyl acetate) and then with recrystallization from ethyl acetate-hexane gave the entitled compound (4.5 g) as crystals.

m.p.: 69–70° C.

Reference Example 90

1,6-Bis(4-bromo-5,6,7-trimethoxyindan-2-yl)hexane

To a solution of 4,5,6-trimethoxy-2-[6-(4,5,6-trimethoxy-2,3-dihydro-1H-2-indenyl)hexyl]indan (1.67 g), sodium acetate (1.10 g), and acetic acid (17 ml) was dropwise added bromine (0.260 ml) at room temperature. After the reaction mixture was stirred for 30 min, 5% aqueous sodium sulfite and water was sequentially added to the reaction mixture with cooling with ice, which was then concentrated in vacuo. The residue was diluted with water and extracted with ethyl acetate. The organic layer was washed with water, saturated aqueous sodium bicarbonate, water, saturated aqueous sodium chloride, dried, and concentrated in vacuo. The residue was purified by alumina column chromatography (ethyl acetate) to yield the entitled compound (2.10 g) as an amorphous.

$^1$H-NMR (CDCl$_3$) δ: 1.14–1.64(12H, m), 2.26–2.72(6H, m), 2.94–3.28(4H, m), 3.87(12H, s), 3.88(6H, s).

Reference Example 91

1,6-Bis(4,5,6,7-tetramethoxyindan-2-yl)hexane

A solution of 1,6-bis(4-bromo-5,6,7-trimethoxyindan-2-yl)hexane (2.10 g), copper bromide(I) (230 mg), ethyl acetate (0.625 ml), and sodium methoxide (28% methanol solution; 100 ml) was heated under reflux for 12 hr. Water was added to the reaction mixture, which was made acidic with concentrated hydrochloric acid and extracted with ethyl acetate. The organic layer was washed with water, saturated aqueous sodium chloride, and dried. The solvent was removed in vacuo. The residue was purified by alumina column chromatography (hexane to hexane:ethyl acetate= 8:1) to yield the entitled compound (1.22 g) as crystals.

m.p.: 100–108° C.

Reference Example 92

4,5,6,7-Tetramethoxy-2-[4-[4-(morpholinocarbonyl) phenoxy]butyl]indan

A mixture of 4-[4-(4,5,6,7-tetramethoxyindan-2-yl) butoxy]benzoic acid (3.50 g), morpholine (1.42 ml), 1-ethyl-3-(3-dimethylaminopropyl)carbodiimide hydrochloride (3.12 g), 1-hydroxybenzotriazole monohydrate (2.45 g), and triethylamine (2.30 ml) in THF (70 ml) was stirred at room temperature for 12 hr. The reaction mixture was diluted with water and extracted with ethyl acetate. The organic layer was washed with 1N hydrochloric acid, water, saturated aqueous sodium bicarbonate, water, and saturated aqueous sodium chloride and dried. Removal of the solvent in vacuo gave the entitled compound (4.00 g).

m.p.: 64–72° C.

Reference Example 93

4,5,6,7-Tetramethoxy-2-[4-[4-(morpholinomethyl) phenoxy]butyl]indan hydrochloride To a solution of 4,5,6,7-tetramethoxy-2-[4-[4-(morpholinocarbonyl)phenoxy]butyl]indan (2.26 g) in THF (23 ml) was added lithium aluminum hydride (365 mg) with cooling with ice. The reaction mixture was then heated under reflux for one hr. 1N Aqueous sodium hydroxide was added at room temperature and the reaction mixture was filtered through Celite and the filtrate was concentrated in vacuo. The residue was purified by alumina column chromatography (hexane to hexane:ethyl acetate=10:1) and converted into its hydrochloride, which was further recrystallized from ethanol-diisopropylether to give the entitled compound (1.28 g).

m.p.: 164–166° C.

Reference Example 94
1-[2-(1,2,3,4-Tetramethoxy-6,7,8,9-tetrahydro-5H-benzo[a] cyclohepten-7-yl)ethyl]-1H-benzo[d]imidazole A mixture of 7-(2-iodoethyl)-1,2,3,4-tetramethoxy-6,7,8, 9-tetrahydro-5H-benzo[a]cycloheptene (1.50 g), benzimidazole (443 mg), and sodium carbonate (760 mg) in DMF (15 ml) was stirred at 70° C. for 8 hr. The reaction mixture was diluted with water and extracted with combined solution of ethyl acetate and THF. The organic layer was washed with water and saturated aqueous sodium chloride and dried. The solvent was removed in vacuo and the residue was diluted with diethylether and the resultant crystals were removed by filtration. The filtrate was concentrate in vacuo. The residue was purified by silica gel column chromatography (hexane to hexane:ethyl acetate=1:2) and then with recrystallization from hexane-ethyl acetate to obtain the entitled compound (480 mg).

m.p.: 121–123° C.

Reference Example 95
3-[2-(1,2,3,4-Tetramethoxy-6,7,8,9-tetrahydro-5H-benzo[a] cyclohepten-7-yl)ethoxy]pyridine A mixture of 7-(2-iodoethyl)-1,2,3,4-tetramethoxy-6,7,8, 9-tetrahydro-5H-benzo[a]cycloheptene (1.20 g), 3-hydroxypyridine (816 mg), and potassium carbonate (2.38 g) in DMF (12 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was purified by alumina column chromatography (ethyl acetate) and then with recrystallization from hexane-ethyl acetate to obtain the entitled compound (430 mg).

m.p.: 111–113° C.

Reference Example 96
1-[2-(1,2,3,4-Tetramethoxy-6,7,8,9-tetrahydro-5H-benzo[a] cyclohepten-7-yl)ethyl]-1,2-dihydro-2-pyridinone, and
  2-[2-(1,2,3,4-Tetramethoxy-6,7,8,9-tetrahydro-5H-benzo [a]cyclohepten-7-yl)ethoxy]pyridine A mixture of 7-(2-iodoethyl)-1,2,3,4-tetramethoxy-6,7,8, 9-tetrahydro-5H-benzo[a]cycloheptene (1.50 g), 2-hydroxypyridine (407 mg), and potassium carbonate (987 mg) in DMF (15 ml) was stirred at room temperature for 12 hr. The reaction mixture was diluted with water and extracted with ethyl acetate. The organic layer was washed with water and saturated aqueous sodium chloride and dried. The solvent was removed in vacuo. The residue was diluted with hexane and the resultant crystals were collected by filtration. The crystals were recrystallized from hexane-ethyl acetate to obtain 2-[2-(1,2,3,4-tetramethoxy-6,7,8,9-tetrahydro-5H-benzo[a]cyclohepten-7-yl)ethoxy]pyridine (830 mg).

m.p.: 132–135° C.

The filtrate was concentrated in vacuo and the residue was purified by silica gel column chromatography(hexane to hexane:ethyl acetate=4:1) to obtain 1-[2-(1,2,3,4-tetramethoxy-6,7,8,9-tetrahydro-5H-benzo[a]cyclohepten-7-yl)ethyl]-1,2-dihydro-2-pyridinone (434 mg).

m.p.: 84–87° C.

Reference Example 97
1-[2-(1,2,3,4-Tetramethoxy-6, 7,8,9-tetrahydro-5H-benzo [a]cyclohepten-7-yl)ethyl]-1,2-dihydro-2-quinolinone, and
  2-[2-(1,2,3,4-Tetramethoxy-6,7,8,9-tetrahydro-5H-benzo [a]cyclohepten-7-yl)ethoxy]quinoline A mixture of 7-(2-iodoethyl)-1,2,3,4-tetramethoxy-6,7,8, 9-tetrahydro-5H-benzo[a]cycloheptene (1.50 g), 2-quinolinol (621 mg), and potassium carbonate (987 mg) in DMF (15 ml) was stirred at room temperature for 12 hr. After being stirred at 60° C. for 6 hr, the reaction mixture was diluted with water and extracted with ethyl acetate. The organic layer was washed with water and saturated aqueous sodium chloride and dried. The solvent was removed in vacuo. The residue was diluted with dilsopropylether. The crystals were collected by filtration and recrystallized from hexane-ethyl acetate to obtain 2-[2-(1,2,3,4-tetramethoxy-6, 7,8,9-tetrahydro-5H-benzo[a]cyclohepten-7-yl)ethoxy] quinoline (680 mg).

m.p.: 175–177° C.

The filtrate was concentrated in vacuo and the residue was purified by silica gel column chromatography(hexane to hexane:ethyl acetate=10:1) to obtain 1-[2-(1,2,3,4-tetramethoxy-6,7,8,9-tetrahydro-5H-benzo[a]cyclohepten-7-yl)ethyl]-1,2-dihydro-2-quinolinone (712 mg).

m.p.: 85–92° C.

Reference Example 98
1-[2-(1,2,3,4-Tetramethoxy-6,7,8,9-tetrahydro-5H-benzo[a] cyclohepten-7-yl)ethyl]-1H-benzotriazole To a suspension of sodium hydride (60% oil dispersion, 230 mg) in THF (6 ml) was added a solution of 1,2,3-benzotriazole (680 mg) in THF(6 ml) with cooling with ice. The reaction mixture was warmed to room temperature and stirred at ambient temperature for 30 min. 7-(2-Iodoethyl)-1,2,3,4-tetramethoxy-6,7,8,9-tetrahydro-5H-benzo[a] cycloheptene (1.20 g) was added and the stirring was continued for 12 hr. The reaction mixture was heated under reflux for 6 hr, diluted with water, and extracted with ethyl acetate. The organic layer was washed with water and saturated aqueous sodium chloride and dried. The solvent was removed in vacuo. The residue was purified by alumina column chromatography(hexane to hexane:ethyl acetate= 4:1) and then with recrystallization from hexane-ethyl acetate to obtain the entitled compound (920 mg).

m.p.: 99–101° C.

EXAMPLE 1
Ethyl 8-(2-ethoxycarbonyl-5,6-dimethoxy-4,7-dioxoindan-2-yl)octanoate A water (1 ml) solution of CAN (342 mg, 0.624 mmols) was dropwise added to an acetonitrile (2 ml) solution of ethyl 8-(2-ethoxycarbonyl-4,5,6,7-tetramethoxyindan-2-yl) octanoate (100 mg, 0.208 mmols), with cooling with ice. The reaction mixture was stirred for 15 minutes and water was added thereto, which was then extracted with ethyl acetate. The organic layer was washed with a saturated aqueous sodium chloride solution and then dried. The solvent was evaporated in vacuo, and the resulting crude product was purified by silica gel column chromatography (hexane only to hexane:ethyl acetate=4:1) to obtain the entitled compound (69 mg) as an oil.

$^1$H-NMR(CDCl$_3$) δ: 1.1–1.8 (18H,m), 2.28 (2H,t,J=7.5 Hz), 2.64–2.82 (2H,m), 3.24–3.42 (2H,m), 3.99 (6H,s), 4.04–4.24 (4H,m).

EXAMPLE 2
8-(2-Carboxy-5,6-dimethoxy-4,7-dioxoindan-2-yl)octanoic acid

A water (1 ml) solution of CAN (287 mg, 0.523 mmols) was dropwise added to an acetonitrile (2 ml) solution of 8-(2-carboxy-4,5,6,7-tetramethoxyindan-2-yl)octanoic acid (88.6 mg, 0.209 mmols) with cooling with ice and then stirring was continued for 15 minutes. Water was added to the reaction mixture, which was then extracted with ethyl acetate. The organic layer was washed with a saturated aqueous sodium chloride solution and then dried. The solvent was evaporated in vacuo, and the resulting crude

EXAMPLE 3
8-(2-Ethoxycarbonyl-5,6-dimethoxy-4,7-dioxoindan-2-yl)octanoic acid product was purified by silica gel column chromatography (hexane:ethyl acetate=1:1 to ethyl acetate only) followed by recrystallization from hexane-ethyl acetate to obtain the entitled compound (32 mg) as crystals.

m.p.: 119–123° C.

EXAMPLE 3
8-(2-Ethoxycarbonyl-5,6-dimethoxy-4,7-dioxoindan-2-yl)octanoic acid A water (1 ml) solution of CAN (238 mg, 0.435 mmols) was dropwise added to an acetonitrile (2 ml) solution of 8-(2-ethoxycarbonyl-4,5,6,7-tetramethoxyindan-2-yl)octanoic acid (78.6 mg, 0.174 mmols) with cooling with ice and then stirring was continued for 15 minutes. Water was added to the reaction mixture, which was then extracted with ethyl acetate. The organic layer was washed with a saturated aqueous sodium chloride solution and then dried. The solvent was evaporated in vacuo and the resulting crude product was purified by silica gel column chromatography (hexane:ethyl acetate=4:1 to ethyl acetate only) to obtain the entitled compound (50 mg) as an oil.

$^1$H-NMR (CDCl$_3$) δ: 1.14–1.84 (12H,m), 1.27 (3H,t,J=7.2 Hz), 2.34 (2H,t,J=7.3 Hz), 2.66–2.82 (2H,m), 3.24–3.42 (2H,m), 4.00 (6H,s), 4.17 (2H,q,J=7.2 Hz).

EXAMPLE 4
N-[8-(2-Ethoxycarbonyl-5,6-dimethoxy-4,7-dioxoindan-2-yl)octanoyl]morpholine A water (1.2 ml) solution of CAN (323 mg, 0.590 mmols) was dropwise added to an acetonitrile (2.5 ml) solution of N-[8-(2-ethoxycarbonyl-4,5,6,7-tetramethoxyindan-2-yl)octanoyl]morpholine (123 mg, 0.236 mmols) with cooling with ice and stirring was continued for 15 minutes. Water was added to the reaction mixture, which was then extracted with ethyl acetate. The organic layer was washed with a saturated aqueous sodium chloride solution and then dried. The solvent was evaporated out in vacuo and the resulting crude product was purified by silica gel column chromatography (hexane:ethyl acetate=2:1 to 1:1) to obtain the entitled compound (66.6 mg) as an oil.

$^1$H-NMR (CDCl$_3$) δ: 1.10–1.80 (12H,m), 1.26 (3H,t,J=7.2 Hz), 2.22–2.38 (2H,m), 2.64–2.82 (2H,m), 3.22–3.54 (4H,m), 3.56–3.74 (6H,m), 3.99 (6H,s), 4.17 (2H,q,J=7.2 Hz).

EXAMPLE 5
8-(2-Carbamoyl-5,6-dimethoxy-4,7-dioxoindan-2-yl)octanamide

A water (1.0 ml) solution of CAN (334 mg, 0.610 mmols) was dropwise added to an acetonitrile (2.0 ml) solution of 8-(2-carbamoyl-4,5,6,7-tetramethoxyindan-2-yl)octanamide (103 mg, 0.244 mmols) with cooling with ice and stirring was continued for 15 minutes. Water was added to the reaction mixture, which was then extracted with ethyl acetate. The organic layer was washed with a saturated aqueous sodium chloride solution and then dried. The solvent was evaporated out in vacuo and the resulting crude product was purified by silica gel column chromatography (ethyl acetate) followed by recrystallization from ethyl acetate to obtain the entitled compound (35 mg) as crystals.

m.p.: 140–143° C.

EXAMPLE 6
Ethyl 2-(8-hydroxyoctyl)-5,6-dimethoxy-4,7-dioxo-2-indancarboxylate A water (1.0 ml) solution of CAN (249 mg, 0.455 mmols) was dropwise added to an acetonitrile (2.0 ml) solution of ethyl 2-(8-hydroxyoctyl)-4,5,6,7-tetramethoxyindancarboxylate (80 mg, 0.182 mmols) with cooling with ice and stirring was continued for 15 minutes. Water was added to the reaction mixture, which was then extracted with ethyl acetate. The organic layer was washed with a saturated aqueous sodium chloride solution and then dried. The solvent was evaporated out in vacuo, and the resulting crude product was purified by silica gel column chromatography (hexane:ethyl acetate=4:1 to 2:1) to obtain the entitled compound (44 mg) as an oil.

$^1$H-NMR (CDCl$_3$) δ: 1.10–1.80 (14H,m), 1.26 (3H,t,J=7.2 Hz), 2.64–2.82 (2H,m), 3.24–3.40 (2H,m), 3.56–3.72 (2H,m), 3.99 (6H,s), 4.17 (2H,q,J=7.2 Hz).

EXAMPLE 7
8-(2-Hydroxymethyl-5,6-dimethoxy-4,7-dioxoindan-2-yl)octanol

A water (1.0 ml) solution of CAN (509 mg, 0.928 mmols) was dropwise added to an acetonitrile (4.0 ml) solution of 8-(2-hydroxymethyl-4,5,6,7-tetramethoxyindan-2-yl)octanol (147 mg, 0.371 mmols) with cooling with ice and stirring was continued for 15 minutes. Water was added to the reaction mixture, which was then extracted with ethyl acetate. The organic layer was washed with a saturated aqueous sodium chloride solution, and then dried. The solvent was evaporated in vacuo, and the resulting crude product was purified by silica gel column chromatography (hexane:ethyl acetate=2:1 to 1:2) followed by recrystallization from hexane-ethyl acetate to obtain the entitled compound (35 mg) as crystals.

m.p.: 59–61° C.

EXAMPLE 8
N-Methyl-2-(8-hydroxyoctyl)-5,6-dimethoxy-4,7-dioxo-2-indancarboxamide A water (1.0 ml) solution of CAN (828 mg, 1.51 mmols) was dropwise added to an acetonitrile (5.0 ml) solution of N-methyl-2-(8-hydroxyoctyl)-4,5,6,7-tetramethoxy-2-indancarboxamide (255 mg, 0.602 mmols), with cooling with ice, and stirring was continued for 15 minutes. Water was added to the reaction mixture, which was then extracted with ethyl acetate. The organic layer was washed with a saturated aqueous sodium chloride solution and then dried. The solvent was evaporated in vacuo, and the resulting crude product was purified by silica gel column chromatography (hexane:ethyl acetate=2:1 to 1:2) followed by recrystallization from ethyl acetate to obtain the entitled compound (106 mg) as crystals.

m.p.: 120–123° C.

EXAMPLE 9
Ethyl 8-(5,6-dimethoxy-4,7-dioxoindan-2-yl)octanoate

A water (1.0 ml) solution of CAN (336 mg, 0.613 mmols) was dropwise added to an acetonitrile (2.0 ml) solution of ethyl 8-(4,5,6,7-tetramethoxyindan-2-yl)octanoate (100 mg, 0.245 mmols) with cooling with ice and stirring was continued for 15 minutes. Water was added to the reaction mixture, which was then extracted with ethyl acetate. The organic layer was washed with a saturated aqueous sodium chloride solution, and then dried. The solvent was evaporated in vacuo, and the resulting crude product was purified by silica gel column chromatography (hexane:ethyl acetate=8:1) followed by recrystallization from hexane to obtain the entitled compound (15 mg) as crystals.

m.p.: 39–40° C.

EXAMPLE 10
2-(8-Hydroxyoctyl)-5,6-dimethoxyindan-4,7-dione

A water (1.0 ml) solution of CAN (463 mg, 0.845 mmols) was dropwise added to an acetonitrile (3.0 ml) solution of 8-(4,5,6,7-tetramethoxyindan-2-yl)octanol (138 mg, 0.338 mmols) with cooling with ice and stirring was continued for 15 minutes. Water was added to the reaction mixture, which was then extracted with ethyl acetate. The organic layer was washed with a saturated aqueous sodium chloride solution, and then dried. The solvent was evaporated out in vacuo, and the resulting crude product was purified by silica gel column chromatography (hexane:ethyl acetate=4:1 to 2:1) followed by recrystallization from hexane-diethyl ether to obtain the entitled compound (29.8 mg) as crystals.

m.p.: 56–58° C.

EXAMPLE 11

Ethyl 2-(4-benzyloxyphenyl)-5,6-dimethoxy-4,7-dioxo-2-indancarboxylate

A water (1.0 ml) solution of CAN (976 mg, 1.78 mmols) was dropwise added to an acetonitrile (7.0 ml) solution of ethyl 2-(4-benzyloxyphenyl)-4,5,6,7-tetramethoxy-2-indancarboxylate (350 mg, 0.711 mmols) with cooling with ice and stirring was continued for 15 minutes. Water was added to the reaction mixture, which was then extracted with ethyl acetate. The organic layer was washed with water and a saturated aqueous sodium chloride solution, and then dried. The solvent was evaporated in vacuo, and the resulting crude product was purified by silica gel column chromatography (hexane:ethyl acetate=5:1) followed by recrystallization from hexane-ethyl acetate to obtain the entitled compound (178 mg) as crystals.

m.p.: 94–97° C.

EXAMPLE 12

2-(4-Benzyloxyphenyl)-5,6-dimethoxy-4,7-dioxo-2-indancarboxylic acid

Acetonitrile (6.0 ml) and ethyl acetate (6.0 ml) were added to 2-(4-benzyloxyphenyl)-4,5,6,7-tetramethoxy-2-indancarboxylic acid (288 mg, 0.620 mmols) to make solution.

A water (2.0 ml) solution of CAN (850 mg, 1.55 mmols) was dropwise added to the resulting solution with cooling with ice and stirring was continued for 15 minutes. Water was added to the reaction mixture, which was then extracted with ethyl acetate. The organic layer was washed with water and a saturated aqueous sodium chloride solution, and then dried. The solvent was evaporated in vacuo, and the resulting crude product was purified by silica gel column chromatography (ethyl acetate) followed by recrystallization from hexane-ethyl acetate to obtain the entitled compound (81 mg) as crystals.

m.p.: 170–175° C.

EXAMPLE 13

Ethyl 2-[4-(4-ethoxycarbonyl-1-oxabutyl)phenyl]-5,6-dimethoxy-4,7-dioxo-2-indancarboxylate A water (1.0 ml) solution of CAN (795 mg, 1.45 mmols) was dropwise added to an acetonitrile (6.0 ml) solution of ethyl 2-[4-(4-ethoxycarbonyl-1-oxabutyl)phenyl]-4,5,6,7-tetramethoxy-2-indancarboxylate (300 mg, 0.581 mmols) with cooling with ice and stirring was continued for 15 minutes. Water was added to the reaction mixture, which was then extracted with ethyl acetate. The organic layer was washed with water and a saturated aqueous sodium chloride solution and then dried. The solvent was evaporated in vacuo, and the resulting crude product was purified by silica gel column chromatography (hexane:ethyl acetate=10:1 to 5:1) to obtain the entitled compound (200 mg) as an oil.

$^1$H-NMR (CDCl$_3$) δ: 1.15 (3H,t,J=7.1 Hz), 1.26 (3H,t,J= 7.1 Hz), 2.01–2.20 (2H,m), 2.50 (2H,t,J=7.3 Hz), 3.16 (2H,d,J=16.3 Hz), 3.87 (2H,d,J=16.3 Hz), 3.99 (2H,t,J=6.0 Hz), 4.00 (6H,s), 4.08 (2H,q,J=7.1 Hz), 4.14 (2H,q,J=7.1 Hz), 6.84 (2H,d,J=8.9 Hz), 7.22 (2H,d,J=8.9 Hz).

EXAMPLE 14

2-[4-(4-Carboxy-1-oxabutyl)phenyl)]-5,6-dimethoxy-4,7-dioxo-2-indancarboxylic acid A water (1.0 ml) solution of CAN (663 mg, 1.21 mmols) was dropwise added to a mixed solution in acetonitrile (2.0 ml) and ethyl acetate (2.0 ml) of 2-[4-(4-carboxy-1-oxabutyl)phenyl]-4,5,6,7-tetramethoxy-2-indancarboxylic acid (250 mg, 0.543 mmols) with cooling with ice and stirring was continued for 15 minutes, into which was further dropped a solution of CAN (265 mg, 0.484 mmols) in water (0.5 ml), and stirring was continued for 15 minutes. Water was added to the reaction mixture, which was then extracted with ethyl acetate. The organic layer was washed with water and a saturated aqueous sodium chloride solution, and then dried. The solvent was evaporated out in vacuo, and the resulting crude product was purified by Florisil column chromatography (ethyl acetate alone to ethyl acetate:methanol=1:1) followed by recrystallization from ethyl acetate to obtain the entitled compound (38 mg) as crystals.

m.p.: 173–177° C.

EXAMPLE 15

Ethyl 4-[4-(5,6-dimethoxy-4,7-dioxoindan-2-yl)butoxy]benzoate

A water (1.0 ml) solution of CAN (299 mg, 0.545 mmols) was dropwise added to an acetonitrile (2.0 ml) solution of ethyl 4-[4-(4,5,6,7-tetramethoxyindan-2-yl)butoxy]benzoate (100 mg, 0.218 mmols), with cooling with ice, and stirring was continued for 15 minutes. Water was added to the reaction mixture, which was then extracted with ethyl acetate. The organic layer was washed with water and a saturated aqueous sodium chloride solution, and then dried. The solvent was evaporated out in vacuo, and the resulting crude product was purified by silica gel column chromatography (hexane:ethyl acetate=10:1 to 8:1) followed by recrystallization (from hexane-ethyl acetate) to obtain the entitled compound (45.0 mg) as crystals.

m.p.: 97–99° C.

EXAMPLE 16

4-[4-(5,6-Dimethoxy-4,7-dioxoindan-2-yl)butoxy]phenylmethanol

A water (1.0 ml) solution of CAN (1.24 g, 2.27 mmols) was dropwise added to an acetonitrile (8.0 ml) solution of 4-[4-(4,5,6,7-tetramethoxyindan-2-yl)butoxy]phenylmethanol (370 mg, 0.888 mmols), with cooling with ice, and stirring was continued for 15 minutes. Water was added to the reaction mixture, which was then extracted with ethyl acetate. The organic layer was washed with water and a saturated aqueous sodium chloride solution, and then dried. The solvent was evaporated out in vacuo, and the resulting crude product was purified by silica gel column chromatography (hexane:ethyl acetate=10:1 to 2:1) followed by recrystallization (from hexane-ethyl acetate) to obtain the entitled compound (150 mg) as crystals.

m.p.: 72–75° C.

EXAMPLE 17

4-[4-(5,6-dimethoxy-4,7-dioxoindan-2-yl)butoxy]benzoic acid

A water (2.0 ml) solution of CAN (1.27 g, 2.32 mmols) was dropwise added to an acetonitrile (8.0 ml) solution of 4-[4-(4,5,6,7-tetramethoxyindan-2-yl)butoxy]benzoic acid (400 mg, 0.929 mmols), with cooling with ice, and stirring was continued for 15 minutes. Water was added to the reaction mixture, which was then extracted with ethyl acetate. The organic layer was washed with water and a saturated aqueous sodium chloride solution, and then dried. The solvent was evaporated out in vacuo, and the resulting crude product was purified by silica gel column chromatography (ethyl acetate) followed by recrystallization (from hexane-ethyl acetate) to obtain the entitled compound (200 mg) as crystals.

m.p.: 149–153° C.

EXAMPLE 18

N,N-Dimethyl-4-[4-(5,6-dimethoxy-4,7-dioxoindan-2-yl) butoxy]benzamide

A water (1.0 ml) solution of CAN (1.07 g, 1.96 mmols) was dropwise added to an acetonitrile (8.0 ml) solution of N,N-dimethyl-4-[4-(4,5,6,7-tetramethoxyindan-2-yl) butoxy]benzamide (358 mg, 0.782 mmols), with cooling with ice, and stirred for 15 minutes. Water was added to the reaction mixture, which was then extracted with ethyl acetate. The organic layer was washed with water and a saturated aqueous sodium chloride solution, and then dried. The solvent was evaporated out in vacuo, and the resulting crude product was purified by silica gel column chromatography (hexane:ethyl acetate=4:1 to 1:2) followed by recrystallization (from diisopropyl ether-ethyl acetate) to obtain the entitled compound (153 mg) as crystals.

m.p.: 80–83° C.

EXAMPLE 19

2-(8-Acetoxyoctyl)-5,6-dimethoxyindan-4,7-dione

To a solution of 8-(4,5,6,7-tetramethoxyindan-2-yl)octyl acetate (1.25 g) in acetonitrile (13 ml) was dropwise added a solution of CAN (4.19 g) in water (13 ml) with cooling with ice. After the reaction mixture was stirred for 15 min, water was added to the reaction mixture, which was extracted with ethyl acetate. The organic layer was washed with water and saturated aqueous sodium chloride, and dried. The solvent was removed in vacuo. The residue was purified by silica gel column chromatography (hexane to hexane:ethyl acetate=10:1) and then with recrystallization from hexane-diethyl ether to yield the entitled compound (700 mg) as crystals.

m.p.: 47–48° C.

EXAMPLE 20

8-(5,6-Dimethoxy-4,7-dioxoindan-2-yl)octyl N-ethylcarbamate

To a solution of 8-(4,5,6,7-tetramethoxyindan-2-yl)octyl N-ethylcarbamate (1.22 g) in acetonitrile (12 ml) was dropwise added a solution of CAN (3.83 g) in water (12 ml) with cooling with ice. After the reaction mixture was stirred for 15 min, water was added to the reaction mixture, which was extracted with ethyl acetate. The organic layer was washed with water and saturated aqueous sodium chloride and dried. The solvent was removed in vacuo. The residue was purified by silica gel column chromatography (hexane to hexane:ethyl acetate=4:1) and then with recrystallization from hexane-ethyl acetate to yield the entitled compound (630 mg) as crystals.

m.p.: 85–86° C.

EXAMPLE 21

N-[8-(5,6-Dimethoxy-4,7-dioxoindan-2-yl)octyl]-N,N-dimethyl amine hydrochloride

To a mixture of N-[8-(4,5,6,7-tetramethoxyindan-2-yl) octyl]-N,N-dimethylamine (620 mg), 2,6-pyridinedicarboxylic acid (660 mg), acetonitrile (6 ml), and water (3 ml) was dropwise added a solution of CAN (2.17 g) in acetonitrile (6 ml) and water (3 ml) with cooling with ice. After the reaction mixture was stirred for 15 min, CAN (866 mg) in water (1.0 ml) was dropwise added with cooling with ice. After the reaction mixture was stirred further 15 min, saturated aqueous sodium bicarbonate was added to the reaction mixture, which was extracted with ethyl acetate. The organic layer was washed with saturated aqueous sodium bicarbonate, water, and saturated aqueous sodium chloride and dried. The solvent was removed in vacuo. The residue was purified by alumina column chromatography (ethyl acetate) and converted into its hydrochloride, which was further recrystallized from ethanol-diisopropylether to yield the entitled compound (330 mg) as crystals.

m.p.: 139–141° C. (decomposed).

EXAMPLE 22

5,6-Dimethoxy-2-[8-(4-phenylpiperidino)octyl]indan-4,7-dione hydrochloride

To a mixture of 1-[8-(4,5,6,7-tetramethoxy-2-yl)octyl]-4-phenylpiperidine (760 mg), 2,6-pyridinedicarboxylic acid (697 mg), acetonitrile (7.6 ml), and water (7.6 ml) was dropwise added a solution of CAN (2.29 g) in acetonitrile (3.8 ml) and water (3.8 ml) with cooling with ice. After the reaction mixture was stirred for 15 min, CAN (762 mg) in water (2.0 ml) was dropwise added with cooling with ice and stirring was continued for additional 15 min. Saturated aqueous sodium bicarbonate was added to the reaction mixture, which was extracted with ethyl acetate. The organic layer was washed with saturated aqueous sodium bicarbonate, water, and saturated aqueous sodium chloride, and dried. The solvent was removed in vacuo. The residue was recrystallized from hexane-ethyl acetate and converted into its hydrochloride, which was further recrystallized from ethanol-diisopropylether to yield the entitled compound (500 mg) as crystals.

m.p.: 162–164° C. (decomposed).

EXAMPLE 23

N-[8-(5,6-Dimethoxy-4,7-dioxoindan-2-yl)octyl] phthalimide

To a mixture of N-[8-(4,5,6,7-tetramethoxyindan-2-yl) octyl]phthalimide (470 mg), 2,6-pyridinedicarboxylic acid (475 mg), acetonitrile (10 ml), and water (5 ml) was dropwise added a solution of CAN (1.56 g) in acetonitrile (1.5 ml) and water (1.5 ml) with cooling with ice. After the reaction mixture was stirred for 15 min, a solution of CAN (520 mg) in water (2.0 ml) was dropwise added with cooling with ice and stirring was continued for additional 15 min. The reaction mixture was diluted with ethyl acetate. The organic layer was washed with water and saturated aqueous sodium chloride, and dried. The solvent was removed in vacuo. The residue was purified by silica gel column chromatography (hexane to hexane:ethyl acetate=5:1) and then with recrystallization from hexane-ethyl acetate to yield the entitled compound (336 mg) as crystals.

m.p.: 91–93° C.

EXAMPLE 24

N-[8-(5,6-Dimethoxy-4,7-dioxoindan-2-yl)octyl]acetamide

To a mixture of N-[8-(4,5,6,7-tetramethoxyindan-2-yl) octyl]acetamide (700 mg), 2,6-pyridinedicarboxylic acid (857 mg), acetonitrile (7.0 ml), ethyl acetate (7.0 ml), and water (7.0 ml) was dropwise added a solution of CAN (3.75 g) in acetonitrile (3.5 ml) and water (3.5 ml) with cooling with ice. After being stirred for 15 min, the reaction mixture was diluted with ethyl acetate. The organic layer was washed with water and saturated aqueous sodium chloride, and dried. The solvent was removed in vacuo. The residue was purified by silica gel column chromatography (ethyl acetate) and then with recrystallization from hexane-ethyl acetate) to yield the entitled compound (495 mg) as crystals.

m.p.: 93–96° C.

EXAMPLE 25

5,6-Dimethoxy-2-[8-[4-(2-pyridyl)piperazin-1-yl]octyl] indan-4,7-dione

To a mixture of 1-[8-(4,5,6,7-tetramethoxylndan-2-yl) octyl]-4-(2-pyridyl)piperazine (1.07 g), 2,6-pyridinedicarboxylic acid (1.05 g), THF (20 ml), and water (10 ml) was dropwise added a solution of CAN (4.55 g) in water (10 ml) with cooling with ice. After the reaction mixture was stirred for 15 min, saturated aqueous sodium bicarbonate was added to the reaction mixture, which was extracted with ethyl acetate. The organic layer was washed with saturated aqueous sodium bicarbonate, water and saturated aqueous sodium chloride, and dried. The solvent was removed in vacuo. The residue was purified by alumina column chromatography (hexane to hexane:ethyl acetate= 5:1), and then with recrystallization from hexane-ethyl acetate to yield the entitled compound (220 mg) as crystals.

m.p.: 80–84° C.

EXAMPLE 26

5,6-Dimethoxy-2-[8-(4-piperidinopiperidino)octyl]indan-4,7-dione dihydrochloride To a mixture of 1-[8-(4,5,6,7-tetramethoxyindan-2-yl) octyl]-4-piperidinopiperidine (802 mg), 2,6-pyridinedicarboxylic acid (777 mg), THF (16 ml), and water (8 ml) was added a solution of CAN (3.37 g) in water (8 ml) with cooling with ice. After the reaction mixture was stirred for 15 min, saturated aqueous sodium bicarbonate was added to the reaction mixture, which was extracted with ethyl acetate. The organic layer was washed with saturated aqueous sodium bicarbonate, saturated aqueous sodium chloride, and dried. The solvent was removed in vacuo. The residue was purified by alumina column chromatography (ethyl acetate) and converted into its hydrochloride, which was further recrystallized from methanol to yield the entitled compound (570 mg) as crystals.

m.p.: 220° C. (decomposed).

EXAMPLE 27

5,6-Dimethoxy-2-[8-(4-diphenylmethylpiperadin-1-yl) octyl]indan-4,7-dione

To a mixture of 1-[8-(4,5,6,7-tetramethoxyindan-2-yl) octyl]-4-diphenylmethylpiperazine (1.00 g), 2,6-pyridinedicarboxylic acid (832 mg), THF (20 ml) and water (10 ml) was dropwise added a solution of CAN (3.61 g) in water (10 ml) with cooling with ice. After the reaction mixture was stirred for 15 min, saturated aqueous sodium bicarbonate was added to the reaction mixture, which was extracted with ethyl acetate. The organic layer was washed with saturated aqueous sodium bicarbonate and saturated aqueous sodium chloride and dried. The solvent was removed in vacuo. The residue was purified by alumina column chromatography (hexane to hexane:ethyl acetate= 5:1) and then with recrystallization from hexane-ethyl acetate to yield the entitled compound (370 mg) as crystals.

m.p.: 112–114° C.

EXAMPLE 28

5,6-Dimethoxy-2-(8-morpholinooctyl)indan-4,7-dione hydrochloride

To a mixture of 4-[8-(4,5,6,7-tetramethoxyindan-2-yl) octyl]morpholine (489 mg), 2,6-pyridinedicarboxylic acid (561 mg), THF (10 ml), and water (5 ml) was dropwise added a solution of CAN (2.46 g) in water (5 ml) with cooling with ice. After the reaction mixture was stirred for 15 min, saturated aqueous sodium bicarbonate was added to the reaction mixture, which was extracted with ethyl acetate. The organic layer was washed with water and saturated aqueous sodium chloride and dried. The solvent was removed in vacuo. The residue was purified by alumina column chromatography (ethyl acetate) and converted into its hydrochloride, which was further recrystallized from ethanol-diisopropylether to yield the entitled compound (360 mg) as crystals.

m.p.: 142–147° C. (decomposed).

EXAMPLE 29

2-[8-(4-Benzylpiperazin-1-yl)octyl]-5,6-dimethoxyindan-4,7-dione

To a mixture of 4-benzyl-1-[8-(4,5,6,7-tetramethoxyindan-2-yl)octyl]piperazine (676 mg), 2,6-pyridinedicarboxylic acid (647 mg), THF (14 ml), and water (7 ml) was dropwise added a solution of CAN (2.83 g) in water (7 ml) with cooling with ice. After the reaction mixture was stirred for 15 min, saturated aqueous sodium bicarbonate was added to the reaction mixture, which was extracted with ethyl acetate. The organic layer was washed with saturated aqueous sodium bicarbonate, water, and saturated aqueous sodium chloride and dried. The solvent was removed in vacuo. The residue was recrystallized from hexane-ethyl acetate to yield the entitled compound (380 mg) as crystals.

m.p.: 80–81° C.

EXAMPLE 30

2-[8-(4-Chlorophenoxy)octyl]-5,6-dimethoxyindan-4,7-dione

To a mixture of 2-[8-(4-chlorophenoxy)octyl]-4,5,6,7-tetramethoxyindan (676 mg), 2,6-pyridinedicarboxylic acid (712 mg), THF (14 ml), and water (7 ml) was dropwise added a solution of CAN (3.11 g) in water (7 ml) with cooling with ice. After the reaction mixture was stirred for 15 min, water was added to the reaction mixture, which was extracted with ethyl acetate. The organic layer was washed with water and saturated aqueous sodium chloride and dried. The solvent was removed in vacuo. The residue was purified by silica gel column chromatography (hexane to hexane:ethyl acetate=10:1) and then with recrystallization from hexane-diethyl ether to yield the entitled compound (320 mg) as crystals.

m.p.: 64–66° C.

EXAMPLE 31

4-[3-(5,6-Dimethoxy-4,7-dioxoindan- 2-yl)propoxy] benzoic acid

To a mixture of 4-[3-(4,5,6,7-tetramethoxyindan-2-yl) propoxy]benzoic acid (1.20 g), 2,6-pyridinedicarboxylic acid (1.44 g), THF (24 ml), and water (12 ml) was dropwise added a solution of CAN (6.30 g) in water (12 ml) with cooling with ice. After the reaction mixture was stirred for 15 min, water was added to the reaction mixture, which was extracted with ethyl acetate. The organic layer was washed with water and saturated aqueous sodium chloride, and dried. The solvent was removed in vacuo. The residue was purified by silica gel column chromatography (ethyl acetate) and then with recrystallization from ethyl acetate to yield the entitled compound (868 mg) as crystals.

m.p.: 171–174° C.

EXAMPLE 32

N,N-Dimethyl-4-[3-(5,6-dimethoxy-4,7-dioxoindan-2-yl) propoxy]benzamide

To a mixture of N, N-dimethyl-4-[3-(4,5,6,7-tetramethoxyindan-2-yl)propoxy]benzamide (700 mg), 2,6- pyridinedicarboxylic acid (792 mg), THF (14 ml), and water (7 ml) was dropwise added a solution of CAN (3.44 g) in water (7 ml) with cooling with ice. After the reaction mixture was stirred for 15 min, water was added to the reaction mixture, which was extracted with ethyl acetate. The organic layer was washed with water and saturated aqueous sodium chloride, and dried. The solvent was removed in vacuo. The residue was purified by silica gel column chromatography (ethyl acetate) and then with recrystallization from hexane-ethyl acetate to yield the entitled compound (438 mg) as crystals.

m.p.: 100–102° C.

EXAMPLE 33
5,6-Dimethoxy-2-[3-(4-dimethylaminomethylphenoxy) propyl]indan-4,7-dione hydrochloride To a mixture of 4,5,6,7-tetramethoxy-2-[3-(4-dimethylaminomethylphenoxy)propyl]indan (948 mg), 2,6-pyridinedicarboxylic acid (1.02 g), THF (19 ml), and water (9.5 ml) was dropwise added a solution of CAN (4.42 g) in water (9.5 ml) with cooling with ice. After the reaction mixture was stirred for 15 min, saturated aqueous sodium bicarbonate was added to the reaction mixture, which was extracted with ethyl acetate. The organic layer was washed with saturated aqueous sodium bicarbonate and saturated aqueous sodium chloride and dried. The solvent was removed in vacuo. The residue was purified by alumina column chromatography (ethyl acetate) and converted into its hydrochloride, which was further recrystallized from ethanol-diisopropylether to yield the entitled compound (770 mg) as crystals.

m.p.: 170° C. (decomposed).

EXAMPLE 34
5,6-Dimethoxy-2-[3-[4-[(4-piperidinopiperidino)carbonyl] phenoxy]propyl]indan-4,7-dione hydrochloride To a mixture of 4,5,6,7-tetramethoxy-2-[3-[4-[(4-piperidinopiperidino)carbonyl]phenoxy]propyl]indan (1.00 g), 2,6-pyridinedicarboxylic acid (887 mg), THF (20 ml), and water (10 ml) was dropwise added a solution of CAN (3.85 g) in water (10 ml) with cooling with ice. After the reaction mixture was stirred for 15 min, saturated aqueous sodium bicarbonate was added to the reaction mixture, which was extracted with ethyl acetate. The organic layer was washed with saturated aqueous sodium bicarbonate and saturated aqueous sodium chloride and dried. The solvent was removed in vacuo. The residue was purified by alumina column chromatography (ethyl acetate) and converted into its hydrochloride, which was further recrystallized from ethanol-diisopropylether to yield the entitled compound (560 mg) as crystals.

m.p.: 176–182° C. (decomposed).

EXAMPLE 35
5,6-Dimethoxy-2-[3-[4-[(4-piperidinopiperidino)methyl] phenoxy]propyl]indan-4,7-dione dihydrochloride To a mixture of 4,5,6,7-tetramethoxy-2-[3-[4-[(4-piperidinopiperidino)methyl]phenoxy]propyl]indan (849 mg), 2,6-pyridinedicarboxylic acid (772 mg), THF (16 ml), and water (8 ml) was dropwise added a solution of CAN (3.35 g) in water (8 ml) with cooling with ice. After the reaction mixture was stirred for 15 min, saturated aqueous sodium bicarbonate was added to the reaction mixture, which was extracted with ethyl acetate. The organic layer was washed with saturated aqueous sodium bicarbonate and saturated aqueous sodium chloride and dried. The solvent was removed in vacuo. The residue was purified by alumina column chromatography (ethyl acetate) and converted into its ahydrochloride, which was further recrystallized from methanol to yield the entitled compound (530 mg) as crystals.

m.p.: 220° C. (decomposed).

EXAMPLE 36
5,6-Dimethoxy-2-[4-[4-[(4-methylpiperizin-1-yl)carbonyl] phenoxy]butyl]indan-4,7-dione A mixture of 4-[4-(5,6-dimethoxy-4,7-dioxoindan-2-yl) butoxy]benzoic acid (500 mg), 1-methylpiperazine (250 mg), 1-ethyl-3-(3-dimethylaminopropyl)carbodiimide hydrochloride (479 mg), 1-hydroxybenzotriazole monohydrate (383 mg), triethylamine (0.697 ml), and THF (20 ml) was stirred at room temperature for 10 hr. The reaction mixture was diluted with water and extracted with ethyl acetate. The organic layer was washed with water and saturated aqueous sodium chloride and dried. The solvent was removed in vacuo. The residue was purified by alumina column chromatography (ethyl acetate) and then with recrystallization from ethyl acetate-diisopropylether to yield the entitled compound (297 mg) as crystals.

m.p.: 97–100° C.

EXAMPLE 37
5,6-Dimethoxy-2-[4-[4-[(4-phenylpiperadin-1-yl)carbonyl] phenoxy]butyl]indan-4,7-dione A mixture of 4-[4-(5,6-dimethoxy-4,7-dioxoindan-2-yl) butoxy]benzoic acid (500 mg), 1-phenylpiperazine (406 mg), 1-ethyl-3-(3-dimethylaminopropyl)carbodiimide hydrochloride (479 mg), 1-hydroxybenzotriazole monohydrate (383 mg), triethylamine (0.697 ml) in THF (20 ml) was stirred at room temperature for 6 hr. The reaction mixture was diluted with water and extracted with combined solvent of THF and ethyl acetate. The organic layer was washed with water and saturated aqueous sodium chloride and dried. The solvent was removed in vacuo. The residue was recrystallized from THF-diisopropylether to yield the entitled compound (400 mg) as crystals.

m.p.: 154–159° C.

EXAMPLE 38
5,6-Dimethoxy-2-[4-[4-[(4-phenylpiperidino)carbonyl] phenoxy]butyl]indan-4,7-dione To a solution of 4-[4-(5,6-dimethoxy-4,7-dioxoindan-2-yl)butoxy]benzoic acid (626 mg), 4-phenylpiperidinehydrochloride (617 mg), 1-ethyl-3-(3-dimethylaminopropyl)carbodiimide hydrochloride (598 mg), 1-hydroxybenzotriazole monohydrate (478 mg), triethylamine (1.30 ml), and THF (12 ml) was stirred at room temperature for 6 hr. The reaction mixture was diluted with water and extracted with ethyl acetate. The organic layer was washed with water, 1N hydrochloric acid, water, saturated aqueous sodium bicarbonate, water, and saturated aqueous sodium chloride and dried. The solvent was removed in vacuo. The residue was recrystallized from ethyl acetate-diethyl ether to yield the entitled compound (482 mg) as crystals.

m.p.: 90–94° C.

EXAMPLE 39
2-[8-(4-Benzylpiperazin-1-yl)octyl]-5,6-dimethoxy-2-phenylindan-4,7-dione To a mixture of 4-benzyl-1-[8-(4,5,6,7-tetramethoxy-2-phenylindan-2-yl)octyl]piperazine (713 mg), 2,6-pyridinedicarboxylic acid (597 mg), THF (14 ml), and water (7 ml) was dropwise added a solution of CAN (2.59 g) in water (7 ml) with cooling with ice. After the reaction mixture was stirred for 15 min, saturated aqueous sodium bicarbonate was added to the reaction mixture, which was extracted with ethyl acetate. The organic layer was washed with saturated aqueous sodium bicarbonate and saturated aqueous sodium chloride and dried. The solvent was removed in vacuo. The residue was purified by alumina column chromatography (hexane to hexane:ethyl acetate 8:1) and then with recrystallization from hexane-diethyl ether to yield the entitled compound (310 mg) as crystals.

m.p.: 78–80° C.

EXAMPLE 40

2-(8-Hydroxyoctyl)-5,6-dimethoxy-2-phenylindan-4,7-dione

To a solution of 8-(4,5,6,7-tetramethoxy-2-phenylindan-2-yl)octanol (1.00 g), 2,6-pyridinedicarboxylic acid (1.13 g), THF (20 ml), and water (10 ml) was dropwise added a solution of CAN (4.92 g) in water (10 ml) with cooling with ice. After the reaction mixture was stirred for 15 min, water was added to the reaction mixture, which was extracted with ethyl acetate. The organic layer was washed with water, and saturated aqueous sodium chloride and dried. The solvent was removed in vacuo. The residue was purified by silica gel column chromatography (hexane to hexane:ethyl acetate= 4:1) to yield the entitled compound (542 mg) as an oil.

$^1$H-NMR (CDCl$_3$) δ: 0.80–1.78(14H, m), 2.96–3.24(4H, m), 3.60(2H, t), 4.01(6H, s), 7.14–7.40(5H, m)

EXAMPLE 41

8-(5,6-Dimethoxy-2-phenyl-4,7-dioxoindan- 2-yl)octanoic acid

To a mixture of 8-(4,5,6,7-tetramethoxy-2-phenylindan-2-yl)octanoic acid (465 mg), 2,6-pyridinedicarboxylic acid (511 mg), THF (10 ml), and water (5 ml) was dropwise added a solution of CAN (2.22 g) in water (5 ml) with cooling with ice. After the reaction mixture was stirred for 15 min, water was added to the reaction mixture, which was extracted with ethyl acetate. The organic layer was washed with water and saturated aqueous sodium chloride and dried. The solvent was removed in vacuo. The residue was purified by silica gel column chromatography (hexane to hexane-:ethyl acetate=2:1) and then with recrystallization from hexane-diethyl ether to yield the entitled compound (220 mg) as crystals.

m.p.: 63–66° C.

EXAMPLE 42

1,6-Bis(5,6-dimethoxy-4,7-dioxoinadan-2-yl)hexane

To a mixture of 1,6-bis(4,5,6,7-tetramethoxyindan-2-yl) hexane (1.07 g), 2,6-pyridinedicarboxylic acid (1.92 g), THF (40 ml), and water (10 ml) was dropwise added a solution of CAN (8.44 g) in water (10 ml) with cooling with ice. After the reaction mixture was stirred for 15 min, water was added to the reaction mixture, which was extracted with ethyl acetate. The organic layer was washed with water and saturated aqueous sodium chloride and dried. The solvent was removed in vacuo. The residue was purified by alumina column chromatography (ethyl acetate) and then with recrystallization from hexane-ethyl acetate to yield the entitled compound (430 mg) as crystals.

m.p.: 144–147° C.

EXAMPLE 43

5,6-Dimethoxy-2-[4-[4-(morpholinocarbonyl)phenoxy] butyl]indan-4,7-dione

To a mixture of 4,5,6,7-tetramethoxy-2-[4-[4-(morpholinocarbonyl)phenoxy]butyl]indan (1.50 g), pyridine-2,6-dicarboxylic acid (1.60 g), THF (30 ml), and water (15 ml) was added an water (15 ml) solution of CAN (7.02 g) with cooling with ice. After being stirred for 15 min, the reaction mixture was diluted with water and extracted with ethyl acetate. The organic layer was washed with water and saturated aqueous sodium chloride and dried. The solvent was removed in vacuo. The residue was recrystallized from ethyl acetate to obtain the entitled compound (965 mg).

m.p.: 128–131° C.

EXAMPLE 44

5,6-Dimethoxy-2-[4-[4-(morpholinomethyl)phenoxy]butyl] indan-4,7-dione hydrochloride To a mixture of 4,5,6,7-tetramethoxy-2-[4-[4-(morpholinomethyl)phenoxy]butyl]indan (1.04 g), pyridine-2,6-dicarboxylic acid (1.08 g), THF (22 ml), and water (11 ml) was added an water (11 ml) solution of CAN (4.71 g) with cooling with ice. After being stirred for 15 min, saturated aqueous sodium bicarbonate was added and the reaction mixture was extracted with ethyl acetate. The organic layer was washed with saturated aqueous sodium bicarbonate, water and saturated aqueous sodium chloride and dried. The solvent was removed in vacuo. The residue was purified by alumina column chromatography (ethyl acetate) and converted into its hydrochloride, which was further recrystallized from ethanol-diisopropylether to obtain the entitled compound (730 mg).

m.p.: 160–164° C. (decomposed)

EXAMPLE 45

Ethyl 2-(2,3-dimethoxy-1,4-dioxo-4,5,6,7,8,9-hexahydro-1H-benzo[a]cyclohepten-7-yl)acetate To a mixture of 2-(1,2,3,4-tetramethoxy-6,7,8,9-tetrahydro-5H-benzo[a]cyclohepten-7-yl)ethyl acetate (800 mg), 2,6-pyridinedicarboxylic acid (1.14 g), THF (16 ml), and water (8 ml) was dropwise added a solution of CAN (4.98 g) in water (8 ml) with cooling with ice. After the reaction mixture was stirred for 15 min, water was added to the reaction mixture, which was extracted with ethyl acetate. The organic layer was washed with water and saturated aqueous sodium chloride and dried. The solvent was removed in vacuo. The residue was purified by silica gel column chromatography (hexane to hexane:ethyl acetate= 4:1) to yield the entitled compound (604 mg) as an oil.

$^1$H-NMR (CDCl$_3$) δ: 0.86–1.20(2H, m), 1.26(3H, t), 1.80–1.98(2H, m), 2.08–2.34(5H, m), 3.10–3.28(2H, m), 3.99(6H, s), 4.14(2H, q).

EXAMPLE 46

7-(2-Hydroxyethyl)-2,3-dimethoxy-4,5,6,7,8,9-hexahydro-1H-benzo[a]cycloheptene-1,4-dione To a mixture of 2-(1,2,3,4-tetramethoxy-6,7,8,9-tetrahydro-5H-benzo[a]cyclohepten-7-yl)ethanol (800 mg), 2,6-pyridinedicarboxylic acid (1.29 g), THF (16 ml), and water (8 ml) was dropwise added a solution of CAN (5.65 g) in water (8 ml) with cooling with ice. After the reaction mixture was stirred for 15 min, water was added to the reaction mixture, which was extracted with ethyl acetate. The organic layer was washed with water and saturated aqueous sodium chloride and dried. The solvent was removed in vacuo. The residue was purified by silica gel column chromatography (hexane to hexane:ethyl acetate= 2:1) and then with recrystallization from hexane-ethyl acetate to yield the entitled compound (479 mg) as crystals.

m.p.: 63–64° C.

EXAMPLE 47

2-(2,3-Dimethoxy-1,4-dioxo-4,5,6,7,8,9-hexahydro-1H-benzo[a]cyclohepten-7-yl)acetic acid To a mixture of 2-(1,2,3,4-tetramethoxy-6,7,8,9-tetrahydro-5H-benzo[a]cyclohepten-7-yl)acetic acid (800 mg), 2,6-pyridinedicarboxylic acid (1.24 g), THF (16 ml), and water (8 ml) was dropwise added a solution of CAN (5.42 g) in water (8 ml) with cooling with ice. After the reaction mixture was stirred for 15 min, water was added to the reaction mixture, which was extracted with ethyl acetate. The organic layer was washed with, 1N hydrochloric acid, water, and saturated aqueous sodium chloride, and dried. The solvent was removed in vacuo. The residue was recrystallized from ethyl acetate to yield the entitled compound (450 mg) as crystals.

m.p.: 130–132° C.

EXAMPLE 48

Ethyl 4-[2-(2,3-dimethoxy-1,4-dioxo-4,5,6,7,8,9-hexahydro-5H-benzo[a]cyclohepten-7-yl)ethoxy]benzoate To a mixture of ethyl 4-[2-(1,2,3,4-tetramethoxy-6,7,8,9-tetrahydro-5H-benzo[a]cyclohepten-7-yl)ethoxy]benzoate (650 mg), 2,6-pyridinedicarboxylic acid (712 mg), THF (28 ml), and water (7 ml) was dropwise added a solution of CAN (3.09 g) in water (7 ml) with cooling with ice. After the reaction mixture was stirred 45 min, the reaction mixture was allowed to warm to room temperature, stirred for additional 15 min, diluted with water, and extracted with ethyl acetate. The organic layer was washed with water and saturated aqueous sodium chloride and dried. The solvent was removed in vacuo. The residue was purified by silica gel column chromatography (hexane to hexane:ethyl acetate= 2:1) and then with recrystallization from hexane-ethyl acetate to yield the entitled compound (430 mg) as crystals.

m.p.: 104–106° C.

EXAMPLE 49

7-[2-[4-(Hydroxymethyl)phenoxy]ethyl]-2,3-dimethoxy-4,5,6,7,8,9-hexahydro-1H-benzo[a]cycloheptene-1,4-dione To a mixture of 4-[2-(1,2,3,4-tetramethoxy-6,7,8,9-tetrahydro-5H-benzo[a]cyclohepten-7-yl)ethoxy]phenylmethanol (261 mg), 2,6-pyridinedicarboxylic acid (314 mg), THF (6 ml), and water (3 ml) was dropwise added a solution of CAN (1.38 g) in water (3 ml) with cooling with ice. After the reaction mixture was stirred for 15 min, water was added to the reaction mixture, which was then extracted with ethyl acetate. The organic layer was washed with water and saturated aqueous sodium chloride and dried. The solvent was removed in vacuo The residue was purified by silica gel column chromatography (hexane to hexane:ethyl acetate=2:1) and then with recrystallization from hexane-ethyl acetate to yield the entitled compound (106 mg) as crystals.

m.p.: 57–59° C.

EXAMPLE 50

4-[2-(2,3-Dimethoxy-1,4-dioxo-4,5,6,7,8,9-hexahydro-1H-benzo[a]cyclohepten-7-yl)ethoxy]benzoic acid To a mixture of 4-[2-(1,2,3,4-tetramethoxy-6,7,8,9-tetrahydro-5H-benzo[a]cyclohepten-7-yl)ethoxy]benzoic acid (1.00 g), 2,6-pyridinedicarboxylic acid (1.16 g), THF (40 ml), and water (10 ml) was dropwise added a solution of CAN (5.09 g) in water (10 ml) with cooling with ice. After the reaction mixture was stirred for 15 min, water was added to the reaction mixture, which was extracted with combined solvent of ethyl acetate and THF. The organic layer was washed with water, and saturated aqueous sodium chloride, and dried. The solvent was removed in vacuo. The residue was recrystallized from THF-ethyl acetate to yield the entitled compound (400 mg) as crystals.

m.p.: 190–195° C.

EXAMPLE 51

7-[2-(4-Chlorophenoxy)ethyl]-2,3-dimethoxy-4,5,6,7,8,9-hexahydro-1H-benzo[a]cycloheptene-1,4-dione To a mixture of 7-[2-(4-chlorophenoxy)ethyl]-1,2,3,4-tetramethoxy-6,7,8,9-tetrahydro-5H-benzo[a]cycloheptene (1.38 g), 2,6-pyridinedicarboxylic acid (1.64 g), THF (52 ml), and water (13 ml) was dropwise added a solution of CAN (7.18 g) in water (13 ml) with cooling with ice. After the reaction mixture was stirred for 15 min, water was added to the reaction mixture, which was extracted with ethyl acetate. The organic layer was washed with water and saturated aqueous sodium chloride and dried. The solvent was removed in vacuo. The residue was purified by alumina column chromatography(ethyl acetate) and then with recrystallization from hexane-ethyl acetate to yield the entitled compound (1.02 g) as crystals.

m.p.: 117–119° C.

EXAMPLE 52

2,3-Dimethoxy-7-[2-(4-phenylphenoxy)ethyl]-4,5,6,7,8,9-hexahydro-1H-benzo[a]cycloheptene-1,4-dione To a mixture of 7-[2-(4-phenylphenoxy)ethyl]-1,2,3,4-tetramethoxy-6,7,8,9-tetrahydro-5H-benzo[a]cycloheptene (1.53 g), 2,6-pyridinedicarboxylic acid (1.66 g), THF (60 ml), and water (15 ml) was dropwise added a solution of CAN (7.24 g) in water (15 ml) with cooling with ice. After the reaction mixture was stirred for 15 min, water was added to the reaction mixture, which was extracted with ethyl acetate. The organic layer was washed with water and saturated aqueous sodium chloride, and dried. The solvent was removed in vacuo. The residue was purified by alumina column chromatography (ethyl acetate) and then with recrystallization from hexane-ethyl acetate to yield the entitled compound (550 mg) as crystals.

m.p.: 109–112° C.

EXAMPLE 53

7-[2-(1H-Benzo[d]imidazol-1-yl)ethyl]-2,3-dimethoxy-4,5,6,7,8,9-hexahydro-1H-benzo[a]cycloheptene-1,4-dione To a mixture of 1-[2-(1,2,3,4-tetramethoxy-6,7,8,9-tetrahydro-5H-benzo[a]cyclohepten-7-yl)ethyl]-1H-benzo[d]imidazole (380 mg), pyridine-2,6-dicarboxylic acid (465 mg), THF (8 ml), and water (4 ml) was added an water (4 ml) solution of CAN (2.03 g) with cooling with ice. After being stirred for 15 min, the reaction mixture was diluted with saturated aqueous sodium bicarbonate and extracted with ethyl acetate. The organic layer was washed with saturated aqueous sodium bicarbonate, water, and saturated aqueous sodium chloride and dried. The solvent was removed in vacuo. The residue was recrystallized from ethyl acetate to obtain the entitled compound (240 mg).

m.p.: 159–163° C.

EXAMPLE 54

2,3-Dimethoxy-7-[2-(3-pyridyloxy)ethyl]-4,5,6,7,8,9-hexahydro-1H-benzo[a]cycloheptene-1,4-dione To a mixture of 3-[2-(1,2,3,4-tetramethoxy-6,7,8,9-tetrahydro-5H-benzo[a]cyclohepten-7-yl)ethoxy]pyridine (470 mg), pyridine-2,6-dicarboxylic acid (607 g), THF (10 ml), and water (5 ml) was added an water (5 ml) solution of CAN (2.65 g) with cooling with ice. After being stirred for 15 min, the reaction mixture was diluted with saturated aqueous sodium bicarbonate and extracted with ethyl acetate. The organic layer was washed with saturated aqueous sodium bicarbonate, water, and saturated aqueous sodium chloride and dried. The solvent was removed in vacuo. The residue was purified by alumina column chromatography (ethyl acetate) and then with recrystallization from hexane-ethyl acetate to obtain the entitled compound (310 mg).

m.p.: 80–82° C.

EXAMPLE 55

2,3-Dimethoxy-7-[2-(2-oxo-1,2-dihydro-1-pyridyl)ethyl]-4,5,6,7,8,9-hexahydro-1H-benzo[a]cycloheptene-1,4-dione To a mixture of 1-[2-(1,2,3,4-tetramethoxy-6,7,8,9-tetrahydro-5H-benzo[a]cyclohepten-7-yl)ethyl]-1,2-dihydro-2-pyridinone (334 mg), pyridine-2,6-dicarboxylic acid (433 mg), THF (8 ml), and water (4 ml) was added an water (4 ml) solution of CAN (1.89 g) with cooling with ice. After being stirred for 15 min, the reaction mixture was diluted with saturated aqueous sodium bicarbonate and extracted with ethyl acetate. The organic layer was washed with water and saturated aqueous sodium chloride and dried. The solvent was removed in vacuo. The residue was recrystallized from diisopropylether to obtain the entitled compound (195 mg).

m.p.: 85–89° C.

EXAMPLE 56

2,3-Dimethoxy-7-[2-(2-pyridyloxy)ethyl]-4,5,6,7,8,9-hexahydro-1H-benzo[a]cycloheptene-1,4-dione To a mixture of 2-[2-(1,2,3,4-tetramethoxy-6,7,8,9-tetrahydro-5H-benzo[a]cyclohepten-7-yl)ethoxy]pyridine (700 mg), pyridine-2,6-dicarboxylic acid (907 mg), THF (14 ml), and water (7 ml) was added an water (7 ml) solution of CAN (3.97 g) with cooling with ice. After being stirred for 15 min, the reaction mixture was diluted with saturated aqueous sodium bicarbonate and extracted with ethyl acetate. The organic layer was washed with water and saturated aqueous sodium chloride and dried. The solvent was removed in vacuo. The residue was purified by silica gel column chromatography (hexane to hexane:ethyl acetate=1:2) to obtain the entitled compound (490 mg) as an oil.

$^1$H-NMR (CDCl$_3$) δ: 0.92–1.20(2H, m), 1.50–2.34(7H, m), 3.07–3.27(2H, m), 3.85–4.05(2H, m), 3.99(6H, s), 6.11–6.22(1H, m), 6.52–6.61(1H, m), 7.18–7.39(2H, m).

EXAMPLE 57

2,3-Dimethoxy-7-[2-(2-oxo-1,2-dihydro-1-quinolyl)ethyl]-4,5,6,7,8,9-hexahydro-1H-benzo[a]cycloheptene-1,4-dione To a mixture of 1-[2-(1,2,3,4-tetramethoxy-6,7,8,9-tetrahydro-5H-benzo[a]cyclohepten-7-yl)ethyl]-1,2-dihydro-2-quinolinone (612 mg), pyridine-2,6-dicarboxylic acid (702 mg), THF (12 ml), and, water (6 ml) was added an water (6 ml) solution of CAN (3.07 g) with cooling with ice. After being stirred for 15 min, the reaction mixture was diluted with water and extracted with ethyl acetate. The organic layer was washed with water and saturated aqueous sodium chloride and dried. The solvent was removed in vacuo. The residue was purified by silica gel column chromatography(hexane to hexane:ethyl acetate=8:1) and then with recrystallization from hexane-ethyl acetate to obtain the entitled compound (310 mg).

m.p.: 88–90° C.

EXAMPLE 58

2,3-Dimethoxy-7-[2-(2-quinolyloxy)ethyl]-4,5,6,7,8,9-hexahydro-1H-benzo[a]cycloheptene-1,4-dione To a mixture of 2-[2-(1,2,3,4-tetramethoxy-6,7,8,9-tetrahydro-5H-benzo[a]cyclohepten-7-yl)ethoxy]quinoline (580 mg), pyridine-2,6-dicarboxylic acid (667 mg), THF (18 ml), and water (6 ml) was added an water (6 ml) solution of CAN (2.92 g) with cooling with ice. After being stirred for 15 min, the reaction mixture was diluted with saturated aqueous sodium bicarbonate and extracted with ethyl acetate. The organic layer was washed with water and saturated aqueous sodium chloride and dried. The solvent was removed in vacuo and the residue was recrystallized from ethyl acetate to obtain the entitled compound (350 mg).

m.p.: 134–136° C.

EXAMPLE 59

7-[2-(1H-Benzotriazol-1-yl)ethyl-2,3-dimethoxy-4,5,6,7,8,9-hexahydro-1H-benzo[a]cycloheptene-1,4-dione To a mixture of 1-[2-(1,2,3,4-tetramethoxy-6,7,8,9-tetrahydro-5H-benzo[a]cyclohepten-7-yl)ethyl]-1H-benzotriazole (800 mg), pyridine-2,6-dicarboxylic acid (973 mg), THF (16 ml), and water (8 ml) was added an water (8 ml) solution of CAN (4.25 g) with cooling with ice. After being stirred for 15 min, 10% aqueous potassium carbonate was added and the reaction mixture was extracted with ethyl acetate. The organic layer was washed with water and saturated aqueous sodium chloride and dried. The solvent was removed in vacuo. The residue was purified by alumina column chromatography (ethyl acetate) and then with recrystallization from hexane-ethyl acetate to obtain the entitled compound (580 mg).

m.p.: 91–93° C.

EXAMPLE 60

4-[2-(2,3-Dimethoxy-1,4-dioxo-4,5,6,7,8,9-hexahydro-1H-benzo[a]cyclohepten-7-yl)ethoxy]-1-benzenecarbonitrile To a solution of 7-(2-hydroxyethyl)-2,3-dimethoxy-4,5,6,7,8,9-hexahydro-1H-benzo[a]cycloheptene-1,4-dione (103 mg), p-cyanophenol (127 mg), triphenylphosphine (126 mg) in THF (2 ml) was added a solution of diethyl azodicarboxylate (90 mg) in THF (1 ml) at room temperature. The reaction mixture was stirred at room temperature for 2 hr and then concentrated in vacuo. The residue was purified by alumina column chromatography (ethyl acetate:hexane=1:4) and then with recrystallization from ethyl acetate-hexane to obtain the entitled compound (118 mg).

m.p.: 105–107° C.

EXAMPLE 61

2,3-Dimethoxy-7-[2-(4-methoxyphenoxy)ethyl]-4,5,6,7,8,9-hexahydro-1H-benzo[a]cycloheptene-1,4-dione To a solution of 7-(2-hydroxyethyl)-2,3-dimethoxy-4,5,6,7,8,9-hexahydro-1H-benzo[a]cycloheptene-1,4-dione (56 mg), p-methoxyphenol (78 mg), and triphenylphosphine (69 mg) in THF (1 ml) was added a solution of diethyl azodicarboxylate (45, mg) in THF (1 ml) at room temperature. The reaction mixture was stirred at room temperature for 2 hr and then concentrated in vacuo. The residue was purified by alumina column chromatography (ethyl acetate:hexane=1:4) and then recrystallized from ethyl acetate-hexane to obtain the entitled compound (68 mg).

m.p.: 76–77° C.

EXAMPLE 62

2,3-Dimethoxy-7-[2-(4-fluorophenoxy)ethyl]-4,5,6,7,8,9-hexahydro-1H-benzo[a]cycloheptene-1,4-dione To a solution of 7-(2-hydroxyethyl)- 2,3-dimethoxy-4,5,6,7,8,9-hexahydro-1H-benzo[a]cycloheptene-1,4-dione (102 mg), p-fluorophenol (129 mg) and triphenylphosphine (132 mg) in THF (2 ml) was added a solution of diethyl azodicarboxylate (81 mg) in THF (1 ml) at room temperature. The reaction mixture was stirred at room temperature for 2 hr and then concentrated in vacuo. The residue was purified by alumina column chromatography (ethyl acetate:hexane=1:10) and then with recrystallization from dIisopropylether to obtain the entitled compound (99 mg).

m.p.: 91–93° C.

EXAMPLE 63

2,3-Dimethoxy-7-[2-(4-methylphenoxy)ethyl]-4,5,6,7,8,9-hexahydro-1H-benzo[a]cycloheptene-1,4-dione To a solution of 7-(2-hydroxyethyl)-2,3-dimethoxy-4,5,6,7,8,9-hexahydro-1H-benzo[a]cycloheptene-1,4-dione (103 mg), p-cresol (118 mg) and triphenylphosphine (121 mg) in THF (2 ml) was added a solution of diethyl azodicarboxylate (87 mg) in THF (1 ml) at room temperature. The reaction mixture was stirred at room temperature for 2 hr and then concentrated in vacuo. The residue was purified by alumina column chromatography (ethyl acetate:hexane=1:10) and then with recrystallization from duisopropylether-hexane to obtain the entitled compound (80 mg).

m.p.: 56–57° C.

EXAMPLE 64

2,3-Dimethoxy-7-[2-(3,5-dimethoxyphenoxy)ethyl]-4,5,6,7,8,9-hexahydro-1H-benzo[a]cycloheptene-1,4-dione To a solution of 7-(2-hydroxyethyl)-2,3-dimethoxy-4,5,6,7,8,9-hexahydro-1H-benzo[a]cycloheptene-1,4-dione (103 mg), 3,5-dimethoxyphenol (168 mg) and triphenylphosphine (125 mg) in THF (2 ml) was added a solution of diethyl azodicarboxylate (81 mg) in THF (1 ml) at room temperature. The reaction mixture was stirred at room temperature for 2 hr and then concentrated in vacuo. The residue was purified by alumina column chromatography (ethyl acetate:hexane=1:4) and then with recrystallization from ethyl acetate-hexane to obtain the entitled compound (108 mg).

m.p.: 63–65° C.

EXAMPLE 65

7-[2-(4-Acetoamidophenoxy)ethyl]-2,3-dimethoxy-4,5,6,7,8,9-hexahydro-1H-benzo[a]cycloheptene-1,4-dione To a solution of 7-(2-hydroxyethyl)-2,3-dimethoxy-4,5,6,7,8,9-hexahydro-1H-benzo[a]cycloheptene-1,4-dione (101 mg), p-hydroxyacetanilide (166 mg), and triphenylphosphine (126 mg) in THF (2 ml) was added a solution of diethyl azodicarboxylate (81 mg) in THF (1 ml) at room temperature. The reaction mixture was stirred at room temperature for 80 min and concentrated. The residue was purified successively by silica gel column chromatography (eluent:ethyl acetate/hexane=1/1) and by alumina column chromatography (eluent:ethyl acetate/hexane=1/1) and then with recrystallization from ethyl acetate-hexane to obtain the entitled compound (93 mg).

m.p.: 151–154° C.

EXAMPLE 66

2,3-Dimethoxy-7-[2-(3,4-methylenedioxyphenoxy)ethyl]-4,5,6,7,8,9-hexahydro-1H-benzo[a]cycloheptene-1,4-dione To a solution of 7-(2-hydroxyethyl)-2,3-dimethoxy-4,5,6,7,8,9-tetrahydro-1H-benzo[a]cycloheptene-1,4-dione (102 mg), sesamol (153 mg), and triphenylphosphine (122 mg) in THF (2 ml) was added a solution of diethyl azodicarboxylate (87 mg) in THF (1 ml) at room temperature. The reaction mixture was stirred at room temperature for 1 hr and concentrated. The residue was purified by alumina column chromatography (eluent:ethyl acetate/hexane=1/4) and then with recrystallization from diethyl ether-hexane to obtain the entitled compound (104 mg).

m.p.: 75–78° C.

EXAMPLE 67

2,3-Dimethoxy-7-(2-phenoxyethyl)-4,5,6,7,8,9-hexahydro-1H-benzo[a]cycloheptene-1,4-dione To a solution of 7-(2-hydroxyethyl)-2,3-dimethoxy-4,5,6,7,8,9-hexahydro-1H-benzo[a]cycloheptene-1,4-dione (100 mg), phenol (109 mg), and triphenylphosphine (127 mg) in THF (2 ml) was added a solution of diethyl azodicarboxylate (82 mg) in THF (1 ml) at room temperature. The reaction mixture was stirred at room temperature for 140 min and concentrated. The residue was purified by alumina column chromatography (eluent:ethyl acetate/hexane=1/10) and then with recrystallization from ethyl acetate-hexane to obtain the entitled compound (78 mg).

m.p.: 71–72° C.

EXAMPLE 68

2,3-Dimethoxy-7-[2-(3,4,5-trimethoxyphenoxy)ethyl]-4,5,6,7,8,9-hexahydro-1H-benzo[a]cycloheptene-1,4-dione To a solution of 7-(2-hydroxyethyl)-2,3-dimethoxy-4,5,6,7,8,9-hexahydro-1H-benzo[a]cycloheptene-1,4-dione (165 mg), 3,4,5-trimethoxyphenol (335 mg), and triphenylphosphine (201 mg) in THF (3 ml) was added a solution of diethyl azodicarboxylate (148 mg) in THF (1 ml) at room temperature. The reaction mixture was stirred at room temperature for 25 min and concentrated. The residue was purified by alumina column chromatography (eluent: ethyl acetate/hexane=1/4) and with recrystallization from ethyl acetate-hexane to obtain the entitled compound (210 mg).

m.p.: 91–93° C.

$^1$H-NMR (CDCl$_3$) δ: 0.94–1.18 (2H, m), 1.72 (2H, q), 1.86–2.03 (3H, m), 2.22 (2H, dd), 3.19 (2H, dd), 3.79 (3H, s), 3.85 (6H, s), 3.96 (2H, t), 4.00 (6H, m), 6.14 (2H, s).

The Chemical structural formulae of the compounds obtained in Examples 1 to 68 are shown in Tables 1 to 5.

TABLE 1

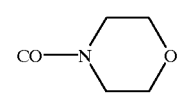

| Ex. No. | $R_a$ | $X_a$ | $Y_b$ |
|---|---|---|---|
| 1 | COOEt | $(CH_2)_7$ | COOEt |
| 2 | COOH | $(CH_2)_7$ | COOH |
| 3 | COOEt | $(CH_2)_7$ | COOH |
| 4 | COOEt | $(CH_2)_7$ | CO—N(morpholine) |

TABLE 1-continued

| Ex. No. | $R_a$ | $X_a$ | $Y_b$ |
| --- | --- | --- | --- |
| 5 | $CONH_2$ | $(CH_2)_7$ | $CONH_2$ |
| 6 | COOEt | $(CH_2)_8$ | OH |
| 7 | $CH_2OH$ | $(CH_2)_8$ | OH |
| 8 | CONHMe | $(CH_2)_8$ | OH |
| 9 | H | $(CH_2)_7$ | COOEt |
| 10 | H | $(CH_2)_8$ | OH |
| 11 | COOEt | —C$_6$H$_4$—O—CH$_2$— | phenyl |
| 12 | COOH | —C$_6$H$_4$—O—CH$_2$— | phenyl |
| 13 | COOEt | —C$_6$H$_4$—O—$(CH_2)_3$— | COOEt |
| 14 | COOH | —C$_6$H$_4$—O—$(CH_2)_3$— | COOH |
| 15 | H | —$(CH_2)_4$—O—C$_6$H$_4$— | COOEt |
| 16 | H | —$(CH_2)_4$—O—C$_6$H$_4$—CH$_2$— | OH |
| 17 | H | —$(CH_2)_4$—O—C$_6$H$_4$— | COOH |
| 18 | H | —$(CH_2)_4$—O—C$_6$H$_4$— | $CONMe_2$ |

TABLE 2
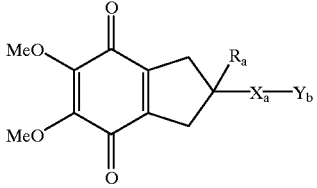
| Ex. No. | Ra | Xa | Yb |
|---|---|---|---|
| 19 | H | (CH₂)₈ | OCOMe |
| 20 | H | (CH₂)₈ | OCONHEt |
| 21 | H | (CH₂)₈ | NMe₂.HCl |
| 22 | H | (CH₂)₈ | 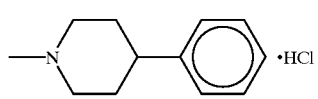 ·HCl |
| 23 | H | (CH₂)₈ | 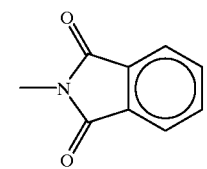 |
| 24 | H | (CH₂)₈ | NHCOMe |
| 25 | H | (CH₂)₈ | 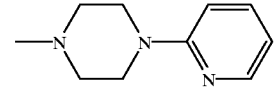 |
| 26 | H | (CH₂)₈ | 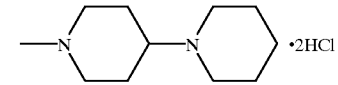 ·2HCl |
| 27 | H | (CH₂)₈ | 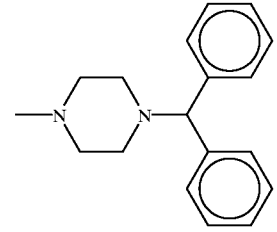 |
| 28 | H | (CH₂)₈ | 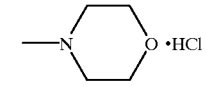 ·HCl |
| 29 | H | (CH₂)₈ | 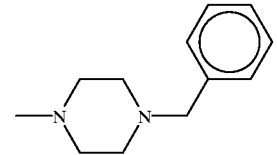 |
| 30 | H | (CH₂)₈ | 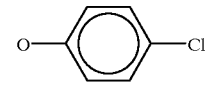 |

TABLE 2-continued

Structure: 4,7-dioxo-5,6-dimethoxy-indane with substituent at 2-position: $R_a$ and $X_a-Y_b$

| Ex. No. | $R_a$ | $X_a$ | $Y_b$ |
|---------|-------|-------|-------|
| 31 | H | —(CH₂)₃—O—C₆H₄— | COOH |
| 32 | H | —(CH₂)₃—O—C₆H₄— | CONMe₂ |

TABLE 3

Structure: 4,7-dioxo-5,6-dimethoxy-indane with $R_a$ and $X_a-Y_b$ at 2-position

| Ex. No. | $R_a$ | $X_a$ | $Y_b$ |
|---------|-------|-------|-------|
| 33 | H | —(CH₂)₃—O—C₆H₄—CH₂— | NMe₂·HCl |
| 34 | H | —(CH₂)₃—O—C₆H₄—CH₂— | —CO—N(piperidinyl)-4-piperidinyl·HCl |
| 35 | H | —(CH₂)₃—O—C₆H₄—CH₂— | —N(piperidinyl)-4-piperidinyl·2HCl |
| 36 | H | —(CH₂)₄—O—C₆H₄— | —CO—N(piperazinyl)-N'-Me |
| 37 | H | —(CH₂)₄—O—C₆H₄— | —CO—N(piperazinyl)-N'-Ph |
| 38 | H | —(CH₂)₄—O—C₆H₄— | —CO—N(4-phenylpiperidinyl) |
| 39 | Ph | (CH₂)₈ | —N(piperazinyl)-N'-CH₂-Ph |

TABLE 3-continued
| Ex. No. | $R_a$ | $X_a$ | $Y_b$ |
|---|---|---|---|
| 40 | 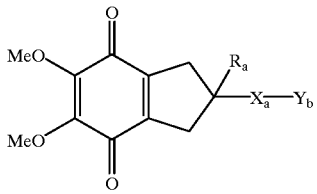 | $(CH_2)_8$ | OH |
| 41 |  | $(CH_2)_7$ | COOH |
| 42 | H | $(CH_2)_6$ | 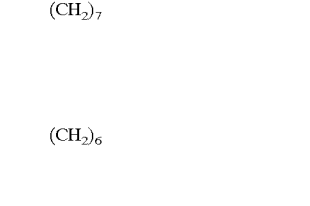 |
| 43 | H | —$(CH_2)_4$—O—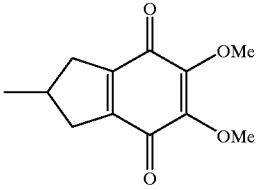— | CO—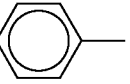 |
| 44 | H | —$(CH_2)_3$—O—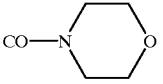—$CH_2$— | 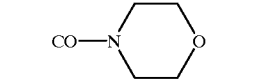·HCl |
TABLE 4
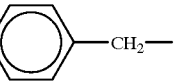
| Ex. No. | $R_a$ | $X_a$ | $Y_b$ |
|---|---|---|---|
| 45 | H | $CH_2$ | COOEt |
| 46 | H | $(CH_2)_2$ | OH |
| 47 | H | $CH_2$ | COOH |
| 48 | H | —$(CH_2)_2$—O—— | COOEt |
| 49 | H | —$(CH_2)_2$—O——$CH_2$— | OH |

TABLE 4-continued

[Structure: 6,7,8,9-tetrahydro-5H-benzocycloheptene-5,9-dione core with 2,3-dimethoxy substituents on the quinone ring, and $R_a$, $X_a$—$Y_b$ substituents at the 7-position]

| Ex. No. | $R_a$ | $X_a$ | $Y_b$ |
|---|---|---|---|
| 50 | H | —(CH₂)₂—O—C₆H₄— | COOH |
| 51 | H | (CH₂)₂ | —O—C₆H₄—Cl (4-chlorophenoxy) |
| 52 | H | —(CH₂)₂—O—C₆H₄— | phenyl |
| 53 | H | (CH₂)₂ | 1-methylbenzimidazol-2-yl |
| 54 | H | (CH₂)₂ | —O-(3-pyridyl) |
| 55 | H | (CH₂)₂ | 1-methyl-2-pyridon-1-yl |
| 56 | H | (CH₂)₂ | —O-(2-pyridyl) |
| 57 | H | (CH₂)₂ | 1-methyl-2-quinolon-1-yl |

TABLE 5

Common structure: 2,3-dimethoxy-benzoquinone fused cycloheptane ring bearing substituent $R_a$ and $X_a$–$Y_b$ at the 7-position.

| Ex. No. | $R_a$ | $X_a$ | $Y_b$ |
|---|---|---|---|
| 58 | H | $(CH_2)_2$ | O-(quinolin-2-yl) |
| 59 | H | $(CH_2)_2$ | 1H-benzotriazol-1-yl |
| 60 | H | $(CH_2)_2$ | O-(4-cyanophenyl) |
| 61 | H | $(CH_2)_2$ | O-(4-methoxyphenyl) |
| 62 | H | $(CH_2)_2$ | O-(4-fluorophenyl) |
| 63 | H | $(CH_2)_2$ | O-(4-methylphenyl) |
| 64 | H | $(CH_2)_2$ | O-(2,5-dimethoxyphenyl) |
| 65 | H | $(CH_2)_2$ | O-(4-acetamidophenyl) |
| 66 | H | $(CH_2)_2$ | O-(1,3-benzodioxol-5-yl) |
| 67 | H | $(CH_2)_2$ | O-phenyl |

TABLE 5-continued

| Ex. No. | $R_a$ | $X_a$ | $Y_b$ |
|---|---|---|---|
| 68 | H | $(CH_2)_2$ | O-(3,4,5-trimethoxyphenyl) |

| | | |
|---|---|---|
| (1) | Compound obtained in Example 10 | 50 mg |
| (2) | Lactose | 34 mg |
| (3) | Corn starch | 10.6 mg |
| (4) | Corn starch (paste) | 5 mg |
| (5) | Magnesium stearate | 0.4 mg |
| (6) | Carboxymethyl cellulose calcium | 20 mg |
| | Total | 120 mg |

The above components (1) to (6) were mixed in an ordinary manner, and tabletted into tablets using a tabletting machine.

Experimental Example 1

Methods

JC1:Wistar rats (male, 12-week old) were used as test animals. The rats were sacrificed by decapitation, and the brain was quickly removed and homogenized with 10 ml of 10 mM Tris-HCl buffer (pH 7.4) containing 150 mM KCl. The resulting homogenate was centrifuged at 2,200 rpm, at 4° C., for 10 minutes, and the supernatant was used in the test. 250 µl of the supernatant was put into a 96-well plate, to which was added a test compound and incubated at 37° C. for 30 minutes.

The concentration of glutamic acid and succinic acid, if added prior to the incubation, was 5.0 mM and 2.5 mM, respectively.

To determine the amount of the peroxylipid formed, used was a thiobarblturic acid (TBA) method. Briefly, 50 µl of 35% perchloric acid was added to the incubated mixture, which was then centrifuged at 2,000 rpm, at 4° C., for 10 minutes. The resulting supernatant was transferred into a different 96-well plate in an amount of 200 µl/well. 100 µl/well of TBA (5 mg/ml TBA in 50% acetic acid) was added thereto, and reacted at 80° C. for 1 hour. Then, the reaction mixture was cooled to room temperature, and its absorbance at 532 nm was measured.

On the other hand, a calibration curve was prepared using tetraethoxypropane which is a substrate for TBA. In the same manner, the peroxylipid concentration in a sample that had been incubated for 30 minutes in the absence of the test compound, and also the peroxylipid concentration in a sample to which had been added 35% perchloric acid prior to the incubation (in the absence of the test compound) were also obtained. The inhibition percentage was calculating according to the following equation. The 50% inhibitory concentration ($IC_{50}$) was obtained, using a log-probit method.

Inhibition Percentage (%)=[(C-A)/(C-B)]×100
where;
A: Peroxylipid concentration in the sample to which was added the test compound;
B: Peroxylipid concentration in the sample to which was added 35% perchloric acid prior to the incubation;
C: Peroxylipid concentration in the sample to which was not added the test compound.

(Results)

The results obtained are shown in Table 6.

TABLE 6

| Test | Peroxylipid Formation Inhibiting Effect (IC$_{50}$; $\mu$M) | |
|---|---|---|
| Compound (Ex. No.) | Brain Homogenate Only | Glutamic Acid and Succinic Acid Added |
| Ex. 9 | 2.3 | 0.94 |
| Ex. 10 | 1.1 | 0.17 |

These results verify that compound (I) of the present invention is effective in inhibiting the formation of peroxylipid in brain homogenates.

In addition, the results further verify that compound (I) of the present invention is greatly effective in inhibiting the formation of peroxylipid in brain homogenates to which were added both glutamic acid and succinic acid, substrates for the complex I and II in the mitochondrial electron-transfer system, respectively.

From those results, it is understood that compound (I) of the present invention protectively acts on the mitochondrial function in mammals, while normalizing the energy production function in mitochondria with strongly inhibiting the peroxylipid formation to be caused by the dysfunction of the electron-transfer system in mammals.

Accordingly, compound (I) promotes the efficient electron transfer via the complex II in mitochondria to increase the energy production in mammals, thereby normalizing the function of the kinetic system and that of the central system in mammals.

INDUSTRIAL APPLICABILITY

As having an excellent mitochondrial function activating effect and an excellent antioxidative effect, compound (I) of the present invention is usable in clinical medicines for preventing and/or treating various diseases such as neurodegenerative disorders (e.g., Parkinson's disease, Alzheimer's disease, amyotrophic lateral sclerosis, Huntington's disease, etc.), other central nervous system disorders (e.g., cerebrovascular dementia, schizophrenia, depression, etc.), mitochondrial disease [e.g., CPEO (chronic progressive external ophthalmoplegia), Kearns-Sayre syndrome, MERRF (myoclonus epilepsy with ragged-red fibers), MELAS (mitochondrial myopathy, encephalopathy lactic acidosis and stroke-like episodes), Leigh disease, Alpers disease, Leber disease, Pearson disease etc.], cardiovascular system disorders (e.g., cardiomyopathy such as congestive cardiomyopathy, etc., arteriosclerosis, myocardial infarction, peripheral vascular disease, angina pectoris, congestive heart failure, hypertension, cardiogenic shock, acute or chronic renal failure, etc.), insulin-independent diabetes mellitus, paropsis, senile hypacusis, hepatic disease, cancer, and so forth.

In addition, compound (I) of the present invention has excellent physical properties of high stability, crystallinity, etc.

What is claimed is:
1. A compound of the formula:

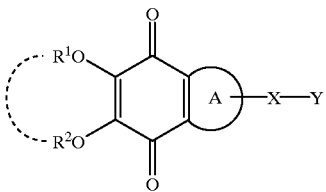

wherein $R^1$ and $R^2$ each represents a lower alkyl, or wherein $R^1$ and $R^2$ may be bonded together to form a ring;

X represents a spacer of which the number of atoms constituting the principle chain is 1 to 15;

Y represents an acyl, a hydroxy which may be substituted, an amino which may be substituted or an aromatic group which may be substituted; and ring A represents a 5- to 8-membered ring which may be further substituted apart from the group of the formula —X—Y wherein each symbol is as defined above, or a salt thereof, wherein the compound is not 4-acetoxy-6,7-dimethoxy-2,2-dimethylchroman-5,8-quinone, and is not

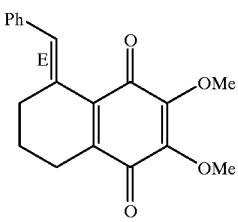

or

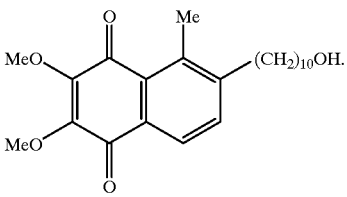

2. A compound of claim 1, wherein $R^1$ and $R^2$ each is a $C_{1-6}$ alkyl, or $R^1$ and $R^2$ form a 5- to 7-membered ring of the formula:

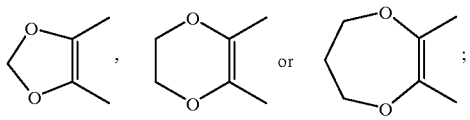

X is (1) a $C_{1-15}$ alkylene, $C_{2-15}$ alkenylene or $C_{2-15}$ alkynylene group, each of which group may be substituted by 1 to 3 substituents selected from the group consisting of oxo and optionally halogenated $C_{1-6}$ alkyl, or (2) a group of the formula:

—(CH$_2$)m—X$^1$—, —(CH$_2$)m—X$^2$—X$^1$—, —X$^1$—X$^2$—(CH$_2$)n-, —X$^2$—X$^1$—(CH$_2$)n-, —(CH$_2$)m—X$^1$—(CH$_2$)n-, —(CH$_2$)m—X$^2$—(CH$_2$)n-, —(CH$_2$)m—X$^1$—X$^2$—(CH$_2$)n-, —(CH$_2$)m—X$^2$—X$^1$—(CH$_2$)n- or —X$^2$—X$^1$—X$^2$—(CH$_2$)n— wherein $X^1$ is a (i) divalent $C_{5-8}$ monocyclic non-aromatic hydrocarbon group, (ii) divalent $C_{6-14}$ aromatic hydrocarbon group or (iii) divalent 5- to 14-membered heterocyclic group containing 1 to 4 hetero atoms selected from the group consisting of nitrogen, sulfur and oxygen atoms in addition to carbon atoms, each of which group may be substituted by 1 to 3 substituents selected from the group consisting of oxo and optionally halogenated $C_{1-6}$ alkyl; $X^2$ is O, S, SO or $SO_2$; m and n each is an integer of 0 to 10; and m+n is an integer of 1 to 13;

Y is (1) an acyl of the formula: —CO—$R^3$, —CO—$OR^3$, —CO—$NR^3R^4$, —CS—$NHR^3$, —$SO_2$—$R^{3a}$ or —SO—$R^{3a}$ wherein $R^3$ is (a) hydrogen, (b) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo, or (c) a 5- to 14-membered heterocyclic group containing 1 to 4 hetero atoms selected from the group consisting of nitrogen, sulfur and oxygen atoms in addition to carbon atoms, which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted by 1 or 2 substituents selected from the group consisting of (xiii-1) a $C_{1-6}$ alkyl, (xiii-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xiii-3) a $C_{6-10}$ aryl-carbonyl, (xiv) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xvi) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvii) sulfo, (xviii) $C_{6-10}$ aryl, (xix) $C_{6-10}$ aryloxy and (xx) oxo, $R^{3a}$ is (a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo, or (b) a 5- to 14-membered heterocyclic group containing 1 to 4 hetero atoms selected from the group consisting of nitrogen, sulfur and oxygen atoms in addition to carbon atoms, which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted by 1 or 2 substituents selected from the group consisting of (xiii-1) a $C_{1-6}$ alkyl, (xiii-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xiii-3) a $C_{6-10}$ aryl-carbonyl, (xiv) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xvi) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvii) sulfo, (xviii) $C_{6-10}$ aryl, (xix) $C_{6-10}$ aryloxy and (xx) oxo, $R^4$ is hydrogen or a $C_{1-6}$ alkyl; or $R^3$ and $R^4$ may, together with the adjacent nitrogen atom, form a 5- to 7-membered nitrogen-containing heterocyclic ring which may be substituted by 1 to 3 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted by 1 or 2 substituents selected from the group consisting of (xiii-1) a $C_{1-6}$ alkyl, (xiii-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xiii-3) a $C_{6-10}$ aryl-carbonyl, (xiv) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xvi) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvii) sulfo, (xviii) $C_{6-10}$ aryl, (xix) $C_{6-10}$ aryloxy and (xx) oxo, (2) a hydroxy which may be substituted by (a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carbomido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo, (b) an acyl of the formula: —CO—$R^3$, —CO—$OR^3$, —CO—$NR^3R^4$, —CS—$NHR^3$, —$SO_2$—$R^{3a}$ or —SO—$R^{3a}$ wherein each symbol is as defined above, or (c) a 5- to 10-membered aromatic heterocyclic group, (3) an amino which may be substituted by 1 or 2 substituents selected from the group consisting of (a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo, and (b) an acyl of the formula: —CO—$R^3$, —CO—$OR^3$, —CO—$NR^3R^4$, —CS—$NHR^3$, —$SO_2$—$R^{3a}$ or —SO—$R^{3a}$ wherein each symbol is as defined above, (4) a 5- to 7-membered saturated cyclic amino which may be substituted by 1 or 2 substituents selected from the group consisting of (i) a $C_{1-6}$ alkyl, (ii) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (iii) a $C_{6-10}$ aryl-carbonyl, or (5) an aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted by 1 or 2 substituents selected from the group consisting of (xiii-1) a $C_{1-6}$ alkyl, (xiii-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xiii-3) a $C_{6-10}$ aryl-carbonyl, (xiv) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xvi) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvii) sulfo, (xviii) $C_{6-10}$ aryl, (xix) $C_{6-10}$ aryloxy and (xx) oxo; and ring A is a 5- to 8-membered carbocyclic or heterocyclic ring optionally containing 1 to 3 hetero atoms selected from the group consisting of nitrogen, sulfur and oxygen atoms in addition to carbon atoms, which ring may contain a double bond apart from the double bond condensed with a quinone ring, and may be further substituted by 1 to 3 substituents selected from the group consisting of (1) carboxy,
(2) $C_{1-6}$ alkoxy-carbonyl,
(3) carbamoyl,
(4) mono- or di-$C_{1-6}$ alkylamino-carbonyl,
(5) optionally hydroxylated $C_{1-6}$ alkyl,
(6) oxo and
(7) $C_{6-14}$ aryl which may be substituted by 1 to 5 substituents selected from the group consisting of (i) halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ aryl-carboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy and nicotinoyloxy, (17') sulfo, (18') $C_{6-10}$ aryl, (19') $C_{6-10}$ aryloxy and (20') oxo.

3. A compound of claim 1, wherein $R^1$ and $R^2$ each is $C_{1-6}$ alkyl.

4. A compound of claim 1, wherein X is a spacer of which the number of atoms constituting the principal chain is 2 to 15.

5. A compound of claim 1, wherein X is (1) a $C_{1-15}$ alkylene which may be substituted by 1 to 3 substituents selected from the group consisting of an oxo and an optionally halogenated $C_{1-6}$ alkyl or (2) a group of the formula: —$(CH_2)$m—$X^1$—, —$(CH_2)$m—$X^2$—$X^1$—, —$X^1$—$X^2$—$(CH_2)$n-, —$X^2$—$X^1$—$(CH_2)$n-, —$(CH_2)$m—$X^1$—$(CH_2)$n-, —$(CH_2)$m—$X^2$—$(CH_2)$n-, —$(CH_2)$m—$X^1$—$X^2$—$(CH_2)$n-, —$(CH_2)$m—$X^2$—$X^1$—$(CH_2)$n- or —$X^2$—$X^1$—$X^2$—$(CH_2)$n- wherein $X^1$ is (i) a divalent $C_{5-8}$ monocyclic non-aromatic hydrocarbon group, (ii) a divalent $C_{6-14}$ aromatic hydrocarbon group or (iii) a divalent 5- to 14-membered heterocyclic group containing 1 to 4 hetero atoms selected from the group consisting of nitrogen, sulfur and oxygen atoms in addition to carbon atoms, each of which group may be substituted by 1 to 3 substituents selected from the group consisting of an oxo and an optionally halogenated $C_{1-6}$ alkyl; $X^2$ is O, S, SO or $SO_2$; m and n each is an integer of 0 to 10; and m+n is an integer of 1 to 13, each of which group may be substituted by 1 to 3 substituents selected from the group consisting of oxo and optionally halogenated $C_{1-6}$ alkyl.

6. A compound of claim 5, wherein $X^1$ is a divalent $C_{6-14}$ aromatic hydrocarbon group, $X^2$ is O, m is an integer of 0 to 10, n is an integer of 1 to 5, and m+n is an integer of 2 to 10.

7. A compound of claim 1, wherein Y is a hydroxy which may be substituted.

8. A compound of claim 1, wherein ring A is a ring of the formula:

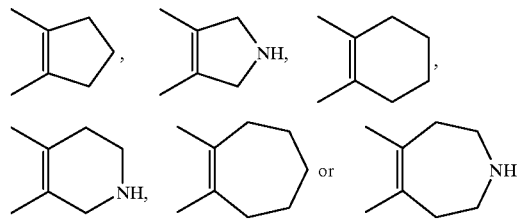

which may be further substituted apart from the group of the formula: —X—Y.

9. A compound of claim 1, wherein $R^1$ and $R^2$ each is $C_{1-6}$ alkyl;

X is (1) a $C_{2-8}$ alkylene or (2) a group of the formula: —$(CH_2)$m—$X^1$—, —$(CH_2)$m—$X^2$—$X^1$—, —$X^1$—$X^2$—$(CH_2)$n-, —$X^2$—$X^1$—$(CH_2)$n-, —$(CH_2)$m—$X^1$—$(CH_2)$n-, —$(CH_2)$m—$X^2$—$(CH_2)$n-, —$(CH_2)$m—$X^1$—$X^2$—$(CH_2)$n-, —$(CH_2)$m—$X^2$—$X^1$—$(CH_2)$n- or —$X^2$—$X^1$—$X^2$—$(CH_2)$n- wherein $X^1$ is a divalent $C_{6-14}$ aromatic hydrocarbon group, $X^2$ is O, m is integer of 0 to 10, n is integer of 1 to 5, and m+n is an integer of 2 to 10;

Y is a hydroxy which may be substituted; and ring A is a ring of the formula:

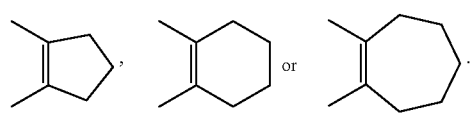

10. A compound of claim 9, wherein Y is a hydroxy substituted by a phenyl which may be substituted by 1 to 3 substituents selected from the group consisting of (i)

halogen, (ii) $C_{1-3}$ alkylenedioxy, (iii) nitro, (iv) cyano, (v) optionally halogenated $C_{1-6}$ alkyl, (vi) optionally halogenated $C_{3-6}$ cycloalkyl, (vii) optionally halogenated $C_{1-6}$ alkoxy, (viii) optionally halogenated $C_{1-6}$ alkylthio, (ix) hydroxy, (x) amino, (xi) mono-$C_{1-6}$ alkylamino, (xii) di-$C_{1-6}$ alkylamino, (xiii) acyl selected from the group consisting of formyl, carboxy, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (xiv) acylamino selected from the group consisting of formylamino, $C_{1-6}$ alkyl-carboxamido, $C_{6-10}$ arylcarboxamido, $C_{1-6}$ alkoxy-carboxamido and $C_{1-6}$ alkylsulfonylamino, (xv) acyloxy selected from the group consisting of $C_{1-6}$ alkyl-carbonyloxy, $C_{6-10}$ arylcarbonyloxy, $C_{1-6}$ alkoxy-carbonyloxy, mono-$C_{1-6}$ alkylcarbamoyloxy, di-$C_{1-6}$ alkyl-carbamoyloxy, $C_{6-10}$ arylcarbamoyloxy and nicotinoyloxy, (xvi) 5- to 7-membered saturated cyclic amino which may be substituted by 1 or 2 substituents selected from the group consisting of (xvi-1) a $C_{1-6}$ alkyl, (xvi-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ arylcarbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxycarbonyloxy, mono-$C_{1-6}$ alkyl-carbamoyloxy and di-$C_{1-6}$ alkyl-carbamoyloxy, and (xvi-3) a $C_{6-10}$ aryl-carbonyl, (xvii) sulfo and (xviii) aromatic group selected from a $C_{6-14}$ aryl, $C_{6-10}$ quinonyl and 5- to 14-membered aromatic heterocyclic group containing 1 to 4 hetero atoms selected from the group consisting of nitrogen, sulfur and oxygen atoms in addition to carbon atoms, each of which group may be substituted by 1 to 5 substituents selected from the group consisting of (1') halogen, (2') $C_{1-3}$ alkylenedioxy, (3') nitro, (4') cyano, (5') optionally halogenated $C_{1-6}$ alkyl, (6') optionally halogenated $C_{3-6}$ cycloalkyl, (7') optionally halogenated $C_{1-6}$ alkoxy, (8') optionally halogenated $C_{1-6}$ alkylthio, (9') hydroxy, (10') amino, (11') mono-$C_{1-6}$ alkylamino, (12') di-$C_{1-6}$ alkylamino, (13') 5- to 7-membered saturated cyclic amino which may be substituted by 1 or 2 substituents selected from the group consisting of (13'-1) a $C_{1-6}$ alkyl, (13'-2) a $C_{6-14}$ aryl, $C_{7-16}$ aralkyl, 5- to 7-membered saturated cyclic amino or 5- or 6-membered aromatic heterocyclic group, each of which group may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkylthio, hydroxy, amino, mono-$C_{1-6}$ alkylamino, di-$C_{1-6}$ alkylamino, $C_{6-10}$ aryl, carboxy, formyl, $C_{1-6}$ alkyl-carbonyl, $C_{1-6}$ alkoxy-carbonyl, $C_{6-10}$ aryl-carbonyl, carbamoyl, mono-$C_{1-6}$ alkyl-carbamoyl, di-$C_{1-6}$ alkyl-carbamoyl, $C_{1-6}$ alkylsulfonyl, formylamino, $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, and (13'-3) a $C_{6-10}$ aryl-carbonyl, (14') acyl selected from the group consisting of formyl, carboxy, $C_{1-6}$ alkyl-carbonyl, $C_{1-6}$ alkoxy-carbonyl, $C_{6-10}$ arylcarbonyl, $C_{6-10}$ aryloxy-carbonyl, $C_{7-16}$ aralkyloxycarbonyl, 5- or 6-membered heterocyclic carbonyl, carbamoyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl and $C_{6-10}$ arylsulfonyl, (15') acylamino selected from the group consisting of formylamino, $C_{1-6}$ alkyl-carboxamido, $C_{6-10}$ arylcarboxamido, $C_{1-6}$ alkoxy-carboxamido and $C_{1-6}$ alkylsulfonylamino, (16') acyloxy selected from the group consisting of $C_{1-6}$ alkyl-carbonyloxy, $C_{6-10}$ arylcarbonyloxy, $C_{1-6}$ alkoxy-carbonyloxy, mono-$C_{1-6}$ alkylcarbamoyloxy, di-$C_{1-6}$ alkyl-carbamoyloxy, $C_{6-10}$ arylcarbamoyloxy and nicotinoyloxy, (17') sulfo, (18') $C_{6-10}$ aryl, (19') $C_{6-10}$ aryloxy and (20') oxo.

11. A compound of claim 1, wherein $R^1$ and $R^2$ each is $C_{1-6}$ alkyl;

X is (1) $C_{1-8}$ alkylene or (2) a group of the formula: —$(CH_2)m'$—$X^{2'}$—$X^{1'}$—, —$X^{1'}$—$X^{2'}$—$(CH_2)n'$— or —$(CH_2)m'$—$X^{2'}$—$X^{1'}$—$(CH_2)n'$— wherein $X^1$ is a 1,4-phenylene, $X^2$ is O, m' is an integer of 1 to 4, and n' is 1 or 2;

Y is (1) a carboxy, (2) a carbonyl substituted by (i) a $C_{1-6}$ alkoxy, (ii) an amino, (iii) a mono- or di-$C_{1-6}$ alkylamino or (iv) a 6-membered saturated cyclic amino which may be substituted by a $C_{1-6}$ alkyl, a phenyl or a piperidino, (3) a hydroxy which may be substituted by (i) a phenyl which may be substituted by 1 to 3 substituents selected from the group consisting of halogen, $C_{1-3}$ alkylenedioxy, cyano, $C_{1-6}$ alkyl, $C_{1-6}$ alkoxy and mono-$C_{1-6}$ alkyl-carbamoyl, (ii) a $C_{1-6}$ alkyl-carbonyl, (iii) a mono- or di-$C_{1-6}$ alkyl-carbamoyl, (iv) a pyridyl or (v) quinolyl, (4) an amino substituted by 1 or 2 substituents selected from the group consisting of $C_{1-6}$ alkyl and $C_{1-6}$ alkyl-carbonyl, (5) a 6-membered saturated cyclic amino which may be substituted by (i) a phenyl, (ii) a benzyl which may be substituted by a phenyl, (iii) a piperidino or (iv) a pyridyl, (6) a phenyl, (7) a $C_{6-10}$ quinonyl substituted by 1 or 2 $C_{1-6}$ alkoxy, (8) a phthalimido, (9) a pyridyl which may be substituted by an oxo, (10) a quinolyl which may be substituted by an oxo, (11) benzotriazolyl or (12) a benzimidazolyl; and ring A is a ring of the formula:

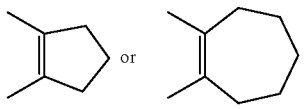

which may be further substituted by a carboxy, $C_{1-6}$ alkoxycarbonyl, carbamoyl, mono- or di-$C_{1-6}$ alkyl-carbamoyl, hydroxy-$C_{1-6}$ alkyl or phenyl.

12. A compound of claim 1, which is a compound of the formula:

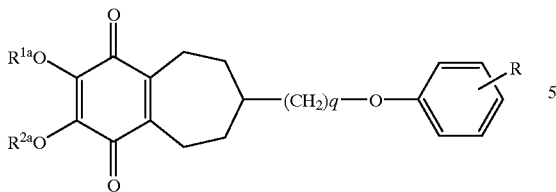

wherein $R^{1a}$ and $R^{2a}$ each is $C_{1-3}$ alkyl; q is an integer of 1 to 4; and R is 1 to 3 substituents selected from the group consisting of halogen, $C_{1-3}$ alkylenedioxy, cyano, optionally halogenated $C_{1-6}$ alkyl, optionally halogenated $C_{1-6}$ alkoxy, $C_{1-6}$ alkoxy-carbonyl, formylamino, $C_{1-6}$ alkyl-carboxamido, $C_{6-10}$ aryl-carboxamido, $C_{1-6}$ alkoxy-carboxamido and $C_{1-6}$ alkylsulfonylamino, or a salt thereof.

13. A compound of claim 1, which is 2-[8-(4-chlorophenoxy)octyl]-5,6-dimethoxyindan-4,7-dione, ethyl 4-[2-(2,3-dimethoxy-1,4-dioxo-4,5,6,7,8,9-hexahydro-1H-benzo[a]cyclohepten-7-yl)ethoxy]benzoate, or 7-[2-(4-chlorophenoxy)ethyl]-2,3-dimethoxy-4,5,6,7,8,9-hexahydro-1H-benzo[a]cycloheptene-1,4-dione.

14. A process for producing a compound of claim 1 which comprises subjecting a compound of the formula:

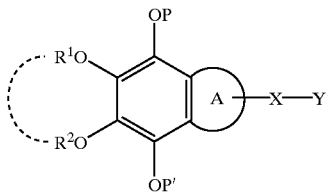

wherein P and P' each represents a protective group and the other symbols are as defined in claim 1, or a salt thereof, quinone production reaction.

15. A pharmaceutical composition which comprises a compound of the formula:

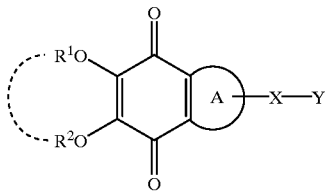

wherein $R^1$ and $R^2$ each represents a lower alkyl, or wherein $R^1$ and $R^2$ may be bonded together to form a ring;

X represents a spacer of which the number of atoms constituting the principle chain is 1 to 15;

Y represents an acyl, a hydroxy which may be substituted, an amino which may be substituted or an aromatic group which may be substituted; and ring A represents a 5- to 8-membered ring which may be further substituted apart from the group of the formula —X—Y wherein each symbol is as defined above, or a salt thereof, together with a pharmaceutically acceptable carrier.

16. A composition of claim 15 which is for preventing or treating disease related to mitochondrial dysfunction.

17. A composition of claim 16, wherein the disease is Parkinson's disease, Alzheimer's disease, amyotrophic lateral sclerosis or Huntington's disease.

18. A method for preventing or treating disease related to mitochondrial dysfunction in a mammal, which comprises administering to said mammal an effective amount of a compound of claim 1 or pharmaceutically acceptable salt thereof with a pharmaceutically acceptable excipient, carrier or diluent.

19. A compound of the formula:

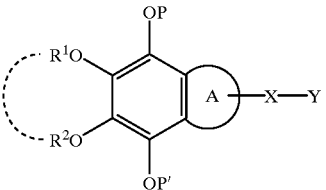

wherein $R^1$ and $R^2$ each represents a lower alkyl, or $R^1$ and $R^2$ may be bonded together to form a ring;

X represents a spacer of which the number of atoms constituting the principal chain is 1 to 15;

Y represents an acyl, a hydroxy which may be substituted, an amino which may be substituted or an aromatic group which may be substituted;

ring A represents a 5- to 8-membered ring which may be further substituted apart from the group of the formula: —X—Y wherein each symbol is as defined above; and P and P' each represents a protective group, or a salt thereof.

20. A pharmaceutical composition for activating a mitochondrial function which comprises a compound of claim 1, if necessary together with a pharmaceutically acceptable carrier.

* * * * *